(12) United States Patent
Cabrera et al.

(10) Patent No.: US 11,849,936 B2
(45) Date of Patent: *Dec. 26, 2023

(54) ENDOSCOPIC STITCHING DEVICES

(71) Applicant: Covidien LP, Mansfield, MA (US)

(72) Inventors: Ramiro Cabrera, Cheshire, CT (US); Thomas Wingardner, North Haven, CT (US); David N. Fowler, Cheshire, CT (US); Brian J. Creston, Madison, CT (US); Dmitri Menn, Marblehead, MA (US); Paul D. Richard, Shelton, CT (US); Gene Stellon, Burlington, CT (US)

(73) Assignee: Covidien LP, Mansfield, MA (US)

( * ) Notice: Subject to any disclaimer, the term of this patent is extended or adjusted under 35 U.S.C. 154(b) by 365 days.

This patent is subject to a terminal disclaimer.

(21) Appl. No.: 17/177,563

(22) Filed: Feb. 17, 2021

(65) Prior Publication Data

US 2021/0169468 A1    Jun. 10, 2021

Related U.S. Application Data

(63) Continuation of application No. 16/211,398, filed on Dec. 6, 2018, now Pat. No. 10,945,722, which is a
(Continued)

(51) Int. Cl.
*A61B 17/04* (2006.01)
*A61B 17/062* (2006.01)
(Continued)

(52) U.S. Cl.
CPC ...... *A61B 17/0469* (2013.01); *A61B 1/00087* (2013.01); *A61B 17/00234* (2013.01);
(Continued)

(58) Field of Classification Search
CPC ............ A61B 1/0055; A61B 2017/003; A61B 17/00234; A61B 2017/00314;
(Continued)

(56) References Cited

U.S. PATENT DOCUMENTS

| 1,822,330 A | 9/1931 | Ainslie |
|---|---|---|
| 2,327,353 A | 8/1943 | Karle |

(Continued)

FOREIGN PATENT DOCUMENTS

| DE | 4423881 C1 | 10/1995 |
|---|---|---|
| EP | 0592244 A2 | 4/1994 |

(Continued)

OTHER PUBLICATIONS

International Search Report for PCT/US2007/021506 dated Apr. 16, 2008 (2 pgs.).

(Continued)

*Primary Examiner* — Katherine M Shi
(74) *Attorney, Agent, or Firm* — CARTER, DELUCA & FARRELL LLP

(57) ABSTRACT

The present disclosure relates to devices, systems and methods for endoscopic suturing or stitching through an access tube or the like. An endoscopic stitching device is provided and includes a handle assembly; an elongate shaft supported by and extending from the handle assembly; and an end effector supported on a distal end of the elongate shaft. The end effector includes a neck assembly configured and adapted for articulation in one direction between a substantially linear configuration and an off-axis configuration, and a pair of juxtaposed jaws pivotally associated with one another. Each jaw defines a suture needle receiving recess formed in a tissue contacting surface thereof.

19 Claims, 53 Drawing Sheets

Related U.S. Application Data continuation of application No. 15/372,616, filed on Dec. 8, 2016, now Pat. No. 10,413,289, which is a continuation of application No. 12/896,364, filed on Oct. 1, 2010, now abandoned, which is a continuation-in-part of application No. 12/482,049, filed on Jun. 10, 2009, now Pat. No. 8,628,545.

(60) Provisional application No. 61/304,825, filed on Feb. 16, 2010, provisional application No. 61/249,063, filed on Oct. 6, 2009, provisional application No. 61/061,136, filed on Jun. 13, 2008.

(51) Int. Cl.
*A61B 1/00* (2006.01)
*A61B 34/00* (2016.01)
*A61B 17/00* (2006.01)
*A61B 17/06* (2006.01)
*A61B 1/005* (2006.01)
*A61B 17/29* (2006.01)

(52) U.S. Cl.
CPC ...... *A61B 17/0491* (2013.01); *A61B 17/0625* (2013.01); *A61B 17/06166* (2013.01); *A61B 34/71* (2016.02); *A61B 1/0055* (2013.01); *A61B 17/062* (2013.01); *A61B 2017/003* (2013.01); *A61B 2017/00367* (2013.01); *A61B 2017/0608* (2013.01); *A61B 2017/0609* (2013.01); *A61B 2017/06047* (2013.01); *A61B 2017/06176* (2013.01); *A61B 2017/2905* (2013.01); *A61B 2017/2912* (2013.01); *A61B 2017/2929* (2013.01)

(58) Field of Classification Search
CPC .... A61B 2017/2905; A61B 2017/2912; A61B 34/71; A61B 17/0469; A61B 17/062; A61B 17/29; A61B 18/1445; A61B 18/1492; A61B 1/0057; A61B 2034/715; A61M 25/0147; A61M 25/0144
See application file for complete search history.

(56) References Cited

U.S. PATENT DOCUMENTS

| | | |
|---|---|---|
| 3,073,311 A | 1/1963 | Tibbs et al. |
| 3,123,077 A | 3/1964 | Alcamo |
| 4,236,470 A | 12/1980 | Stenson |
| 4,686,963 A | 8/1987 | Cohen et al. |
| 4,890,615 A | 1/1990 | Caspari et al. |
| 4,923,461 A | 5/1990 | Caspari et al. |
| 4,934,340 A | 6/1990 | Ebling et al. |
| 4,935,026 A | 6/1990 | McFadden |
| 4,935,027 A | 6/1990 | Yoon |
| 4,957,498 A | 9/1990 | Caspari et al. |
| 5,037,433 A | 8/1991 | Wilk et al. |
| 5,042,707 A | 8/1991 | Taheri |
| 5,080,663 A | 1/1992 | Mills et al. |
| 5,100,421 A | 3/1992 | Christoudias |
| 5,100,430 A | 3/1992 | Avellanet et al. |
| 5,106,381 A | 4/1992 | Chikama |
| 5,209,747 A | 5/1993 | Knoepfler |
| 5,224,948 A | 7/1993 | Abe et al. |
| 5,254,088 A | 10/1993 | Undquist et al. |
| 5,271,543 A | 12/1993 | Grant et al. |
| 5,282,806 A | 2/1994 | Haber et al. |
| 5,300,082 A | 4/1994 | Sharpe et al. |
| 5,308,353 A | 5/1994 | Beurrier |
| 5,314,446 A | 5/1994 | Hunter et al. |
| 5,330,502 A | 7/1994 | Hassler et al. |
| 5,336,229 A | 8/1994 | Noda |
| 5,350,391 A | 9/1994 | Iacovelli |
| 5,358,479 A | 10/1994 | Wilson |
| 5,358,498 A | 10/1994 | Shave |
| 5,363,861 A * | 11/1994 | Edwards ......... A61M 25/0144 604/95.04 |
| 5,374,277 A | 12/1994 | Hassler |
| 5,381,943 A | 1/1995 | Allen et al. |
| 5,387,221 A | 2/1995 | Bisgaard |
| 5,389,103 A | 2/1995 | Melzer et al. |
| 5,391,176 A | 2/1995 | de la Torre |
| 5,403,342 A | 4/1995 | Tovey et al. |
| 5,405,352 A | 4/1995 | Weston |
| 5,409,498 A | 4/1995 | Braddock et al. |
| 5,439,478 A | 8/1995 | Palmer |
| 5,448,989 A | 9/1995 | Heckele |
| 5,454,823 A | 10/1995 | Richardson et al. |
| 5,454,827 A | 10/1995 | Aust et al. |
| 5,465,894 A | 11/1995 | Clark et al. |
| 5,472,446 A | 12/1995 | de la Torre |
| 5,478,344 A | 12/1995 | Stone et al. |
| 5,480,406 A | 1/1996 | Nolan et al. |
| 5,487,757 A | 1/1996 | Truckai et al. |
| 5,496,334 A | 3/1996 | Klundt et al. |
| 5,527,323 A | 6/1996 | Jervis et al. |
| 5,540,375 A | 7/1996 | Bolanos et al. |
| 5,540,703 A | 7/1996 | Barker, Jr. et al. |
| 5,540,706 A | 7/1996 | Aust et al. |
| 5,549,617 A | 8/1996 | Green et al. |
| 5,549,637 A | 8/1996 | Crainich |
| 5,562,686 A | 10/1996 | Sauer et al. |
| 5,564,615 A | 10/1996 | Bishop et al. |
| 5,571,090 A | 11/1996 | Sherts |
| 5,573,286 A | 11/1996 | Rogozinski |
| 5,575,799 A | 11/1996 | Bolanos et al. |
| 5,582,617 A | 12/1996 | Klieman et al. |
| 5,588,581 A | 12/1996 | Conlon et al. |
| 5,591,181 A | 1/1997 | Stone et al. |
| 5,601,224 A | 2/1997 | Bishop et al. |
| 5,607,095 A | 3/1997 | Smith et al. |
| 5,620,415 A | 4/1997 | Lucey et al. |
| 5,628,756 A | 5/1997 | Barker, Jr. et al. |
| 5,630,825 A | 5/1997 | de la Torre et al. |
| 5,632,751 A | 5/1997 | Piraka |
| 5,634,584 A | 6/1997 | Okorocha et al. |
| 5,643,293 A | 7/1997 | Kogasaka et al. |
| 5,643,294 A | 7/1997 | Tovey et al. |
| 5,656,011 A * | 8/1997 | Uihlein ............. A61M 25/0138 600/150 |
| 5,662,662 A | 9/1997 | Bishop et al. |
| 5,662,666 A | 9/1997 | Onuki et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,690,653 A | 11/1997 | Richardson et al. |
| 5,702,408 A | 12/1997 | Wales et al. |
| 5,715,942 A | 2/1998 | Li et al. |
| 5,728,107 A | 3/1998 | Zlock et al. |
| 5,728,109 A | 3/1998 | Schulze et al. |
| 5,728,113 A | 3/1998 | Sherts |
| 5,730,747 A | 3/1998 | Ek et al. |
| 5,746,751 A | 5/1998 | Sherts |
| 5,749,828 A | 5/1998 | Solomon et al. |
| 5,749,898 A | 5/1998 | Schulze et al. |
| 5,752,973 A | 5/1998 | Kieturakis |
| 5,755,729 A | 5/1998 | de la Torre et al. |
| 5,759,188 A | 6/1998 | Yoon |
| 5,766,196 A | 6/1998 | Griffiths |
| 5,772,578 A | 6/1998 | Heimberger et al. |
| 5,779,646 A | 7/1998 | Koblish et al. |
| 5,782,828 A | 7/1998 | Chen et al. |
| 5,792,153 A | 8/1998 | Swain et al. |
| 5,792,165 A | 8/1998 | Klieman et al. |
| 5,797,537 A | 8/1998 | Oberlin et al. |
| 5,797,842 A | 8/1998 | Pumares et al. |
| 5,797,927 A | 8/1998 | Yoon |
| 5,797,928 A | 8/1998 | Kogasaka |
| 5,807,241 A | 9/1998 | Heimberger |
| 5,814,054 A | 9/1998 | Kortenbach et al. |
| 5,814,069 A | 9/1998 | Schulze et al. |
| 5,817,119 A | 10/1998 | Klieman et al. |

(56) References Cited

U.S. PATENT DOCUMENTS

| | | |
|---|---|---|
| 5,827,323 A | 10/1998 | Klieman et al. |
| 5,855,560 A | 1/1999 | Idaomi et al. |
| 5,865,836 A | 2/1999 | Miller |
| 5,871,488 A | 2/1999 | Tovey et al. |
| 5,876,412 A | 3/1999 | Piraka |
| 5,893,592 A | 4/1999 | Schulze et al. |
| 5,897,563 A | 4/1999 | Yoon et al. |
| 5,906,630 A | 5/1999 | Anderhub et al. |
| 5,908,428 A | 6/1999 | Scirica et al. |
| 5,911,727 A | 6/1999 | Taylor |
| 5,928,136 A | 7/1999 | Barry |
| 5,931,855 A | 8/1999 | Buncke |
| 5,938,668 A | 8/1999 | Scirica et al. |
| 5,941,430 A | 8/1999 | Kuwabara |
| 5,947,982 A | 9/1999 | Duran |
| 5,951,575 A | 9/1999 | Bolduc et al. |
| 5,954,731 A | 9/1999 | Yoon |
| 5,954,733 A | 9/1999 | Yoon |
| 5,957,937 A | 9/1999 | Yoon |
| 5,980,538 A | 11/1999 | Fuchs et al. |
| 5,984,932 A | 11/1999 | Yoon |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,017,358 A | 1/2000 | Yoon et al. |
| 6,027,522 A | 2/2000 | Palmer |
| 6,051,006 A | 4/2000 | Shluzas et al. |
| 6,071,289 A | 6/2000 | Stefanchik et al. |
| 6,077,287 A | 6/2000 | Taylor et al. |
| 6,080,180 A | 6/2000 | Yoon et al. |
| 6,086,601 A | 7/2000 | Yoon |
| 6,119,913 A | 9/2000 | Adams et al. |
| 6,126,665 A | 10/2000 | Yoon |
| 6,126,666 A | 10/2000 | Trapp et al. |
| 6,139,563 A | 10/2000 | Cosgrove, III et al. |
| 6,143,005 A | 11/2000 | Yoon et al. |
| 6,171,316 B1 | 1/2001 | Kovac et al. |
| 6,206,893 B1 | 3/2001 | Klein et al. |
| 6,214,028 B1 | 4/2001 | Yoon et al. |
| 6,223,100 B1 | 4/2001 | Green |
| 6,224,614 B1 | 5/2001 | Yoon |
| 6,261,307 B1 | 7/2001 | Yoon et al. |
| 6,277,132 B1 | 8/2001 | Brhel |
| 6,319,262 B1 | 11/2001 | Bates et al. |
| 6,332,889 B1 | 12/2001 | Sancoff et al. |
| 6,346,111 B1 | 2/2002 | Gordon et al. |
| 6,358,259 B1 | 3/2002 | Swain et al. |
| 6,494,888 B1 | 12/2002 | Laufer et al. |
| 6,506,196 B1 | 1/2003 | Laufer |
| 6,517,539 B1 | 2/2003 | Smith et al. |
| 6,533,796 B1 | 3/2003 | Sauer et al. |
| 6,544,215 B1 | 4/2003 | Bencini et al. |
| 6,569,105 B1 | 5/2003 | Kortenbach et al. |
| 6,582,450 B2 | 6/2003 | Ouchi |
| 6,585,717 B1 | 7/2003 | Wittenberger et al. |
| 6,596,015 B1 | 7/2003 | Pitt et al. |
| 6,599,310 B2 | 7/2003 | Leung et al. |
| 6,638,287 B2 | 10/2003 | Danitz et al. |
| 6,663,639 B1 | 12/2003 | Laufer et al. |
| 6,663,641 B1 | 12/2003 | Kovac et al. |
| 6,666,854 B1 | 12/2003 | Lange |
| 6,676,676 B2 | 1/2004 | Danitz et al. |
| 6,695,774 B2 | 2/2004 | Hale et al. |
| 6,702,780 B1 | 3/2004 | Gilboa et al. |
| 6,719,764 B1 | 4/2004 | Gellman et al. |
| 6,719,765 B2 | 4/2004 | Bonutti |
| 6,743,239 B1 | 6/2004 | Kuehn et al. |
| 6,743,240 B2 | 6/2004 | Smith et al. |
| 6,755,843 B2 | 6/2004 | Chung et al. |
| 6,773,441 B1 | 8/2004 | Laufer et al. |
| 6,786,913 B1 | 9/2004 | Sancoff et al. |
| 6,821,285 B2 | 11/2004 | Laufer et al. |
| 6,835,200 B2 | 12/2004 | Laufer et al. |
| 6,889,116 B2 | 5/2005 | Jinno |
| 6,936,054 B2 | 8/2005 | Chu |
| 6,936,061 B2 | 8/2005 | Sasaki |
| 6,955,643 B2 | 10/2005 | Gellman et al. |
| 6,972,017 B2 | 12/2005 | Smith et al. |
| 6,981,628 B2 | 1/2006 | Wales |
| 6,991,635 B2 | 1/2006 | Takamoto et al. |
| 6,997,931 B2 | 2/2006 | Sauer et al. |
| 7,011,668 B2 | 3/2006 | Sancoff et al. |
| 7,037,315 B2 | 5/2006 | Sancoff et al. |
| 7,037,324 B2 | 5/2006 | Martinek |
| 7,041,111 B2 | 5/2006 | Chu |
| 7,052,489 B2 | 5/2006 | Griego et al. |
| RE39,152 E | 6/2006 | Aust et al. |
| 7,063,710 B2 | 6/2006 | Takamoto et al. |
| 7,063,715 B2 | 6/2006 | Onuki et al. |
| 7,107,124 B2 | 9/2006 | Green |
| 7,153,314 B2 | 12/2006 | Laufer et al. |
| 7,191,900 B2 | 3/2007 | Opie et al. |
| 7,192,437 B2 | 3/2007 | Shalaby |
| 7,211,093 B2 | 5/2007 | Sauer et al. |
| 7,218,972 B2 | 5/2007 | Rodriguez |
| 7,232,448 B2 | 6/2007 | Battles et al. |
| 7,244,260 B2 | 7/2007 | Koseki |
| 7,248,944 B2 | 7/2007 | Green |
| 7,303,106 B2 | 12/2007 | Milliman et al. |
| 7,468,068 B2 | 12/2008 | Kolster |
| 7,553,275 B2 | 6/2009 | Padget et al. |
| 7,601,164 B2 | 10/2009 | Wu |
| 7,645,284 B2 | 1/2010 | Burbank et al. |
| 7,666,194 B2 | 2/2010 | Field et al. |
| 7,691,112 B2 | 4/2010 | Chanduszko et al. |
| 7,704,261 B2 | 4/2010 | Sakamoto et al. |
| 7,708,747 B2 | 5/2010 | Bjerken |
| 7,722,630 B1 | 5/2010 | Stone et al. |
| 7,731,726 B2 | 6/2010 | Belhe et al. |
| 7,736,372 B2 | 6/2010 | Reydel et al. |
| 7,758,597 B1 | 7/2010 | Tran et al. |
| 7,758,598 B2 | 7/2010 | Conlon et al. |
| 7,766,925 B2 | 8/2010 | Stokes et al. |
| 7,771,438 B2 | 8/2010 | Dreyfuss et al. |
| 7,776,059 B2 | 8/2010 | Craig |
| 7,776,066 B2 | 8/2010 | Onuki et al. |
| 7,780,701 B1 | 8/2010 | Meridew et al. |
| 7,784,612 B2 | 8/2010 | Kanda et al. |
| 7,798,325 B2 | 9/2010 | Wizemann et al. |
| 7,814,630 B2 | 10/2010 | Price et al. |
| 7,815,654 B2 | 10/2010 | Chu |
| 7,815,659 B2 | 10/2010 | Conlon et al. |
| 7,828,812 B2 | 11/2010 | Stokes et al. |
| 7,833,235 B2 | 11/2010 | Chu |
| 7,833,237 B2 | 11/2010 | Sauer |
| 7,837,696 B2 | 11/2010 | Modesitt et al. |
| 7,842,047 B2 | 11/2010 | Modesitt et al. |
| 7,842,048 B2 | 11/2010 | Ma |
| 7,846,170 B2 | 12/2010 | Modesitt et al. |
| 7,850,701 B2 | 12/2010 | Modesitt et al. |
| 7,883,517 B2 | 2/2011 | Pantages et al. |
| 7,883,519 B2 | 2/2011 | Oren et al. |
| 7,887,554 B2 | 2/2011 | Stokes et al. |
| 7,935,128 B2 | 5/2011 | Rioux et al. |
| 7,947,052 B2 | 5/2011 | Baxter, III et al. |
| 7,947,053 B2 | 5/2011 | McKay et al. |
| 7,951,157 B2 | 5/2011 | Gambale |
| 7,955,298 B2 | 6/2011 | Carroll et al. |
| 7,967,832 B2 | 6/2011 | Chu |
| 7,967,842 B2 | 6/2011 | Bakos |
| 7,972,323 B1 | 7/2011 | Bencini et al. |
| 7,972,344 B2 | 7/2011 | Murray et al. |
| 7,976,552 B2 | 7/2011 | Suzuki |
| 8,518,052 B2 | 8/2013 | Burgermeister et al. |
| 8,628,545 B2 | 1/2014 | Cabrera et al. |
| 8,708,954 B2 * | 4/2014 | Webler ............... A61P 9/10 604/95.04 |
| 8,801,735 B2 | 8/2014 | Shelton, IV et al. |
| 9,010,605 B2 | 4/2015 | Olson et al. |
| 10,080,566 B2 | 9/2018 | Milliman |
| 10,945,722 B2 | 3/2021 | Cabrera et al. |
| 2002/0010480 A1 | 1/2002 | Sancoff et al. |
| 2002/0065526 A1 | 5/2002 | Oren et al. |

(56) References Cited

U.S. PATENT DOCUMENTS

| | | |
|---|---|---|
| 2002/0068868 A1 | 6/2002 | Thompson et al. |
| 2002/0072702 A1 | 6/2002 | Quay |
| 2002/0128666 A1 | 9/2002 | Sancoff et al. |
| 2002/0165461 A1 | 11/2002 | Hayzelden et al. |
| 2002/0173800 A1 | 11/2002 | Dreyfuss et al. |
| 2002/0198542 A1 | 12/2002 | Yamamoto et al. |
| 2003/0009195 A1 | 1/2003 | Field et al. |
| 2003/0014077 A1 | 1/2003 | Leung et al. |
| 2003/0045891 A1 | 3/2003 | Yamamoto et al. |
| 2003/0105475 A1 | 6/2003 | Sancoff et al. |
| 2003/0105476 A1 | 6/2003 | Sancoff et al. |
| 2003/0114832 A1 | 6/2003 | Kohler et al. |
| 2003/0114863 A1 | 6/2003 | Field et al. |
| 2003/0116670 A1 | 6/2003 | Gentry |
| 2003/0171761 A1 | 9/2003 | Sancoff et al. |
| 2003/0233104 A1 | 12/2003 | Gellman et al. |
| 2004/0010245 A1 | 1/2004 | Cerier et al. |
| 2004/0060409 A1 | 4/2004 | Leung et al. |
| 2004/0060410 A1 | 4/2004 | Leung et al. |
| 2004/0068272 A1 | 4/2004 | Sauer et al. |
| 2004/0087976 A1 | 5/2004 | DeVries et al. |
| 2004/0092967 A1 | 5/2004 | Sancoff et al. |
| 2004/0181243 A1 | 9/2004 | Chu et al. |
| 2004/0193186 A1 | 9/2004 | Kortenbach et al. |
| 2004/0199179 A1* | 10/2004 | Elliott ............... A61B 18/1477 606/127 |
| 2004/0199184 A1 | 10/2004 | Topper et al. |
| 2005/0043747 A1 | 2/2005 | Field et al. |
| 2005/0085832 A1 | 4/2005 | Sancoff et al. |
| 2005/0096694 A1 | 5/2005 | Lee |
| 2005/0126876 A1 | 6/2005 | Simmons |
| 2005/0165419 A1 | 7/2005 | Sauer et al. |
| 2005/0256533 A1 | 11/2005 | Roth et al. |
| 2006/0025817 A1 | 2/2006 | Ortiz et al. |
| 2006/0036232 A1 | 2/2006 | Primavera et al. |
| 2006/0069396 A1 | 3/2006 | Meade et al. |
| 2006/0111209 A1 | 5/2006 | Hinman et al. |
| 2006/0111732 A1 | 5/2006 | Gibbens et al. |
| 2006/0184106 A1 | 8/2006 | McDaniel et al. |
| 2006/0235304 A1 | 10/2006 | Harhen et al. |
| 2006/0253126 A1 | 11/2006 | Bjerken et al. |
| 2006/0282093 A1 | 12/2006 | Shelton et al. |
| 2007/0005110 A1 | 1/2007 | Collier et al. |
| 2007/0239022 A1* | 10/2007 | Harhen ................. A61B 8/12 600/459 |
| 2008/0091169 A1 | 4/2008 | Heideman et al. |
| 2008/0188868 A1 | 8/2008 | Weitzner et al. |
| 2008/0221392 A1 | 9/2008 | Jorgensen |
| 2008/0249364 A1 | 10/2008 | Korner |
| 2008/0255421 A1 | 10/2008 | Hegeman et al. |
| 2008/0300462 A1 | 12/2008 | Intoccia et al. |
| 2010/0076433 A1* | 3/2010 | Taylor ............... A61B 18/1445 606/170 |
| 2014/0326777 A1 | 11/2014 | Zingman |
| 2019/0343517 A1 | 11/2019 | Zemlok et al. |
| 2019/0380714 A1 | 12/2019 | Chen et al. |
| 2020/0015820 A1 | 1/2020 | Contini et al. |

FOREIGN PATENT DOCUMENTS

| | | |
|---|---|---|
| EP | 0647431 A2 | 4/1995 |
| EP | 1481628 A1 | 12/2004 |
| EP | 1915957 A2 | 4/2008 |
| EP | 1915966 A1 | 4/2008 |
| EP | 2044890 A1 | 4/2009 |
| WO | 9811814 A2 | 3/1998 |
| WO | 9811829 A1 | 3/1998 |
| WO | 9853745 A1 | 12/1998 |
| WO | 9915090 A1 | 4/1999 |
| WO | 9918859 A1 | 4/1999 |
| WO | 0067834 A1 | 11/2000 |
| WO | 0174254 A1 | 10/2001 |
| WO | 0234147 A1 | 5/2002 |
| WO | 03017850 A2 | 3/2003 |
| WO | 03028541 A2 | 4/2003 |
| WO | 2006061868 A1 | 6/2006 |
| WO | 2008042423 A2 | 4/2008 |
| WO | 2008045333 A2 | 4/2008 |
| WO | 2008045348 A2 | 4/2008 |
| WO | 2008045394 A2 | 4/2008 |
| WO | 2009132284 A2 | 10/2009 |

OTHER PUBLICATIONS

European Search Report for EP 07839357.6 date of completion Oct. 31, 2012 (10 pgs.).

European Search Report for EP12169361.8 dated Aug. 6, 2012.

European Search Report for EP 09251544.4-1659 date of completion is Feb. 21, 2013 (18 pages).

Canadian Office Action dated Oct. 27, 2015 in corresponding Canadian Patent Application No. 2,668,518.

European Search Report from EP 07 83 9340 dated Dec. 2, 2013 (8 pages).

European Search Report for EP 22 25 0290 dated Sep. 11, 2014.

Extended European Search Report for EP 07 83 9323 dated Sep. 4, 2014.

European Search Report for EP 11 25 0257 dated Jun. 15, 2011.

Canadian Office Action dated Oct. 27, 2015 in corresponding Canadian Patent Application No. 2,668,618.

* cited by examiner

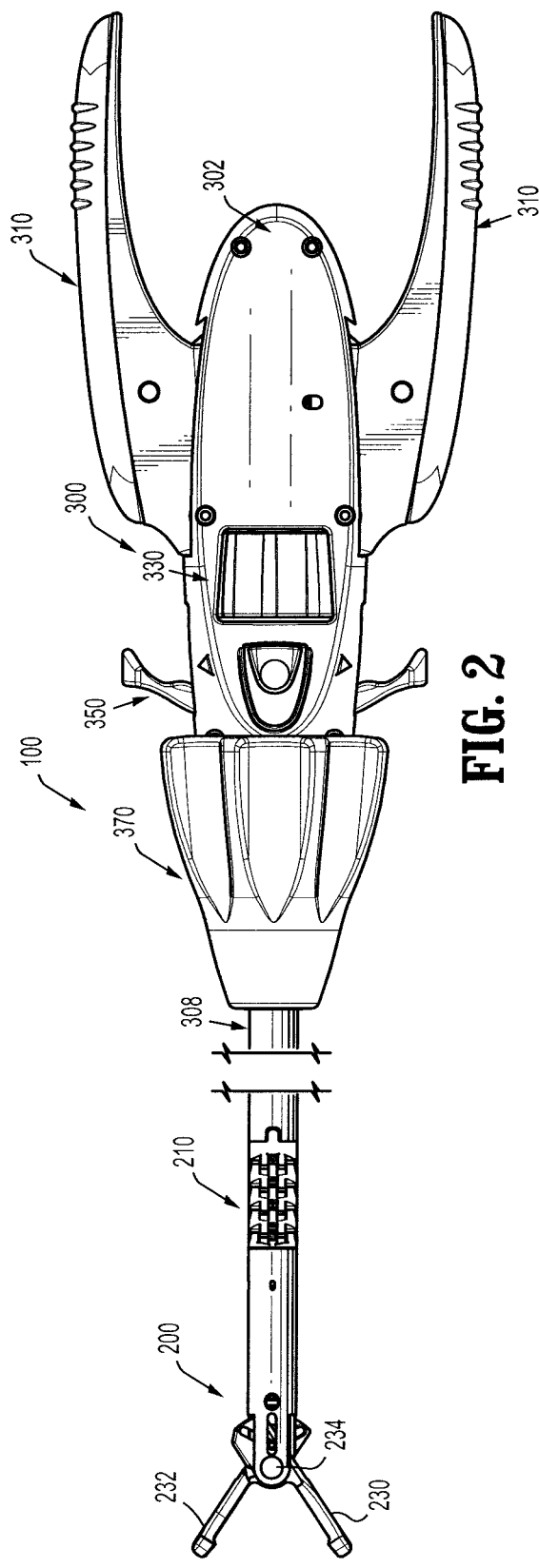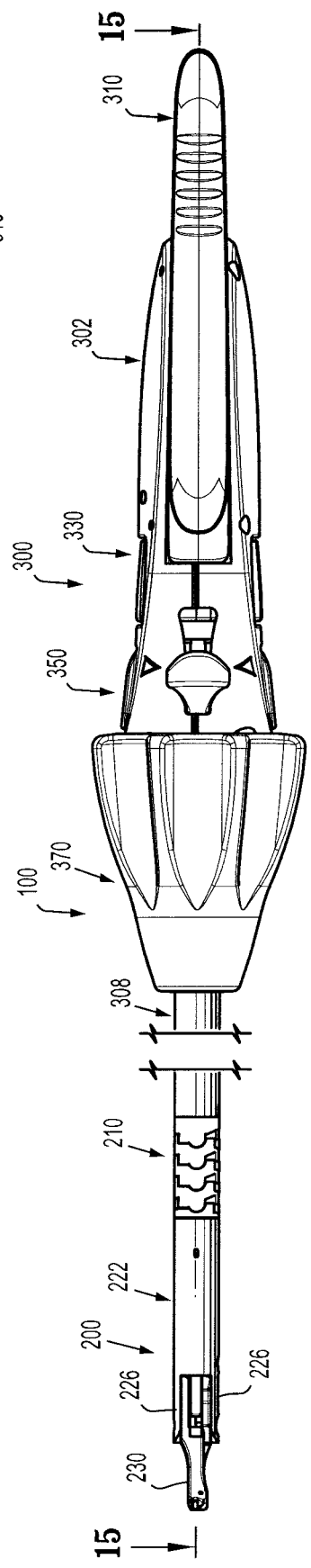

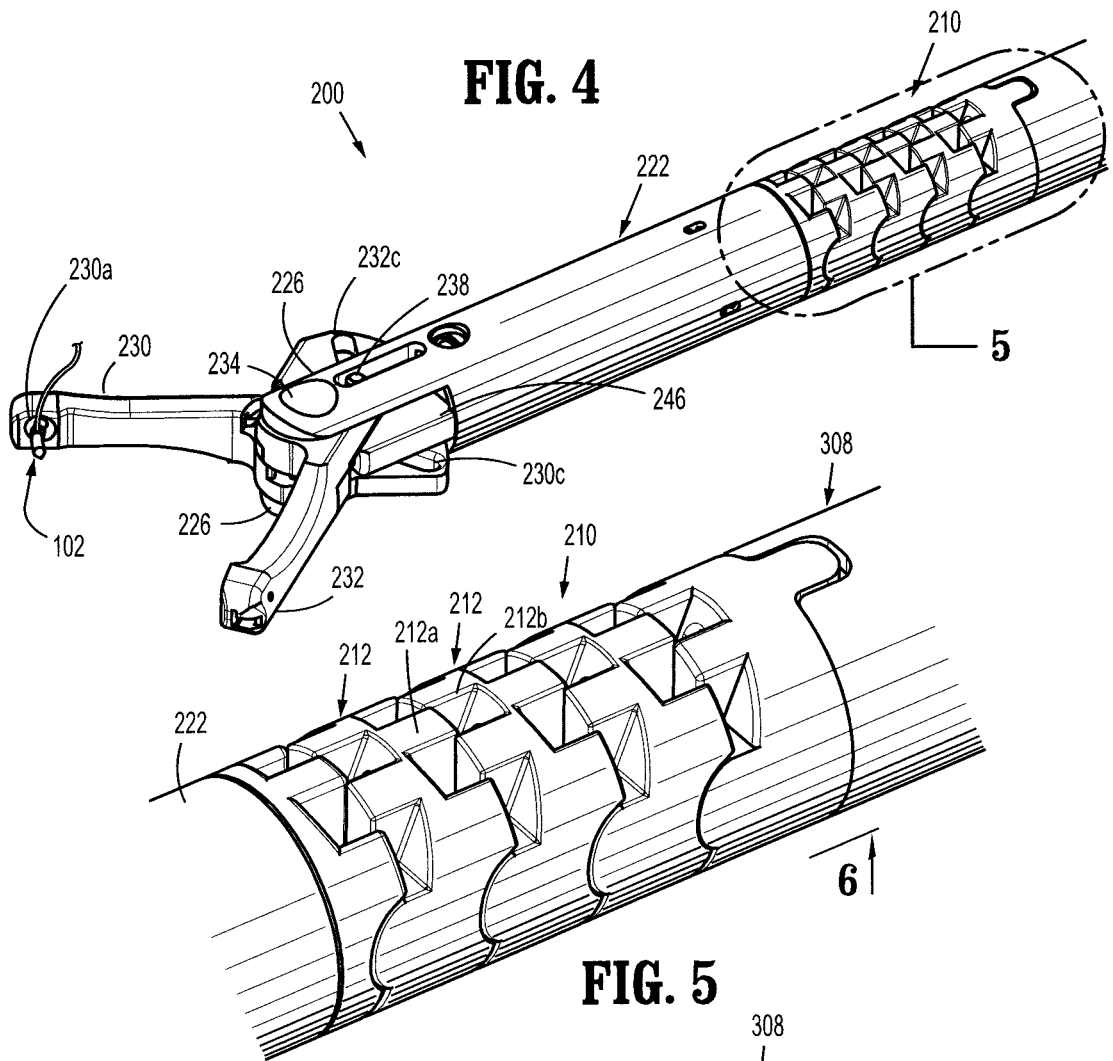
FIG. 4
FIG. 5
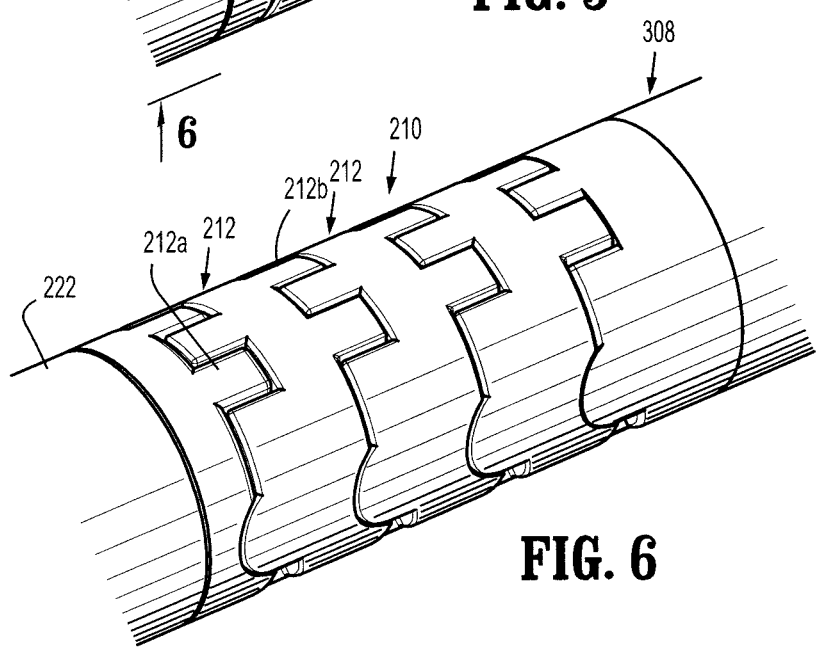
FIG. 6

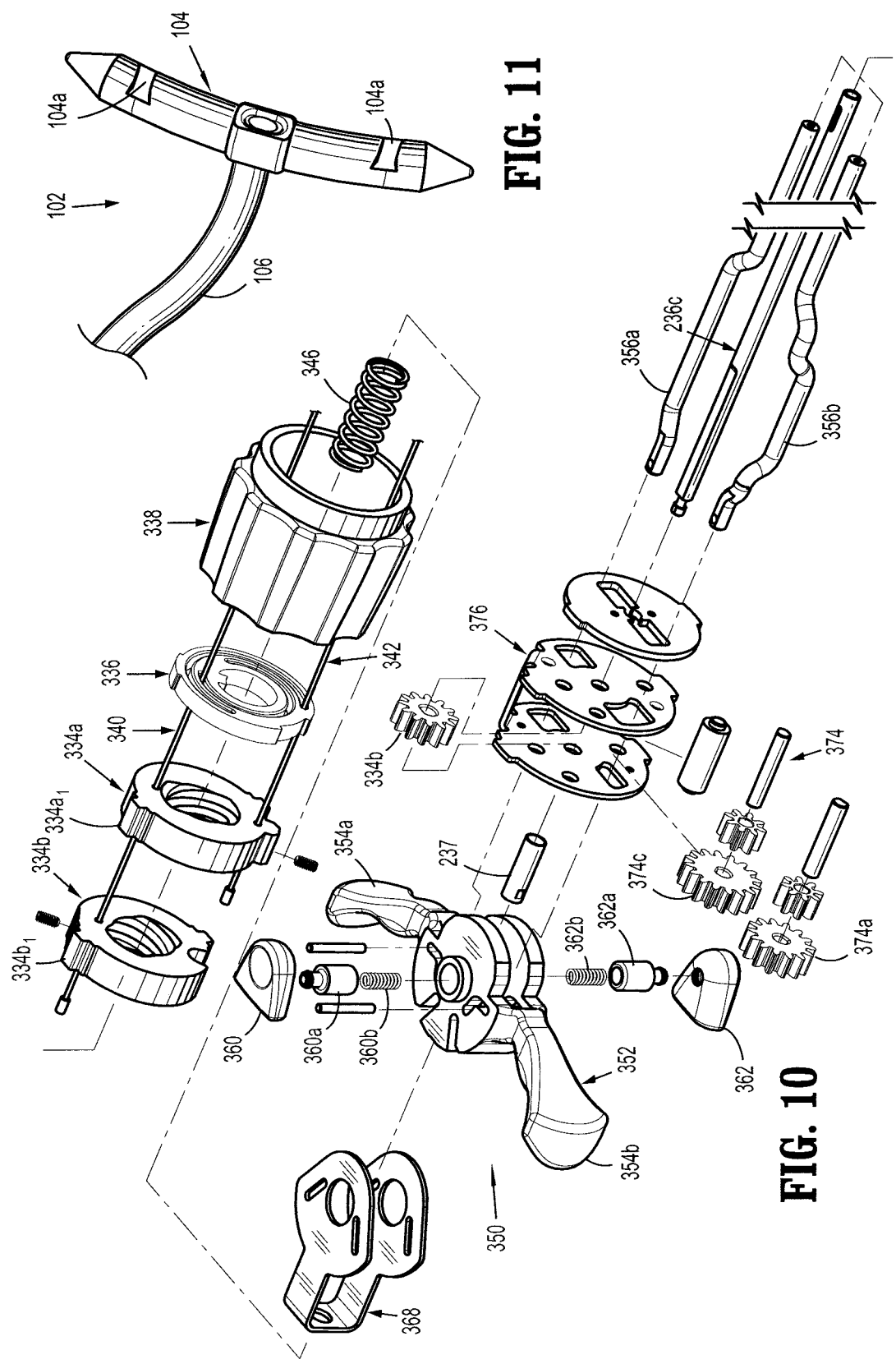

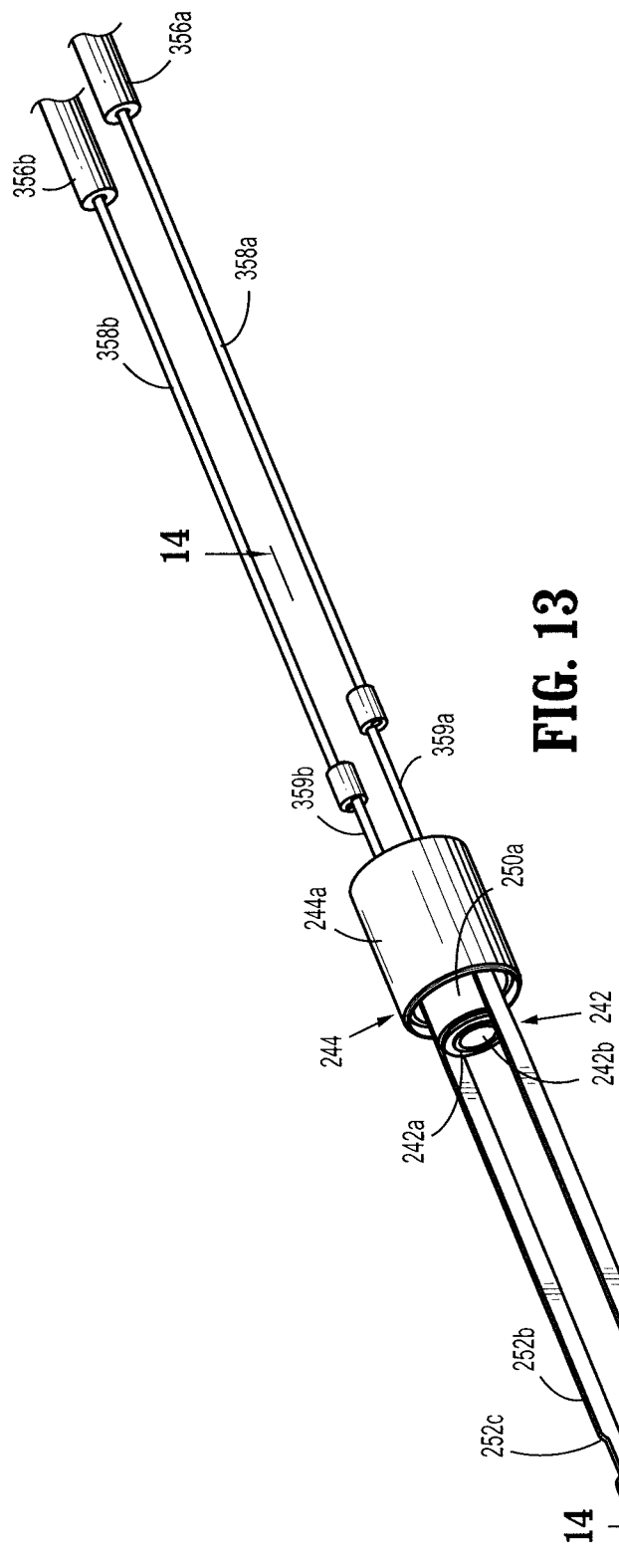
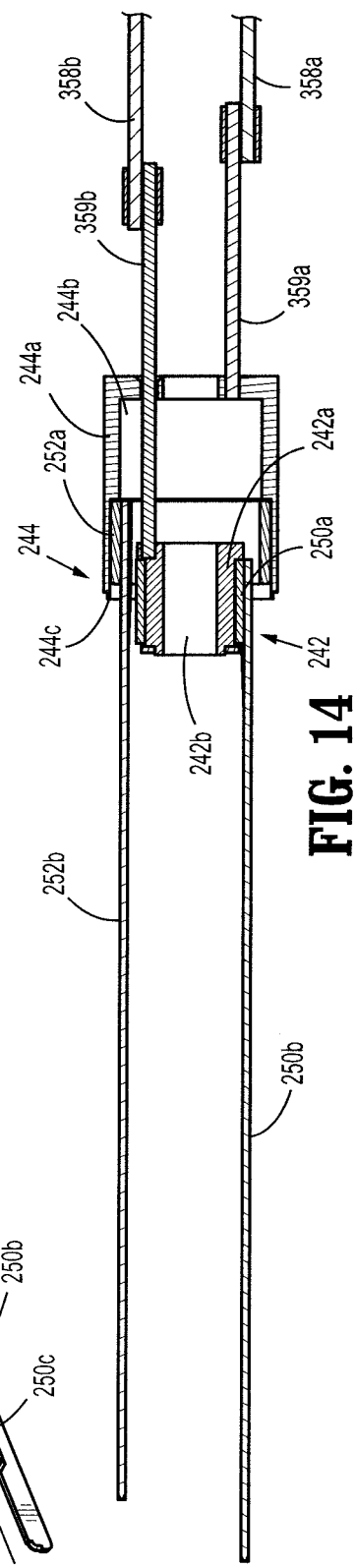
FIG. 13
FIG. 14

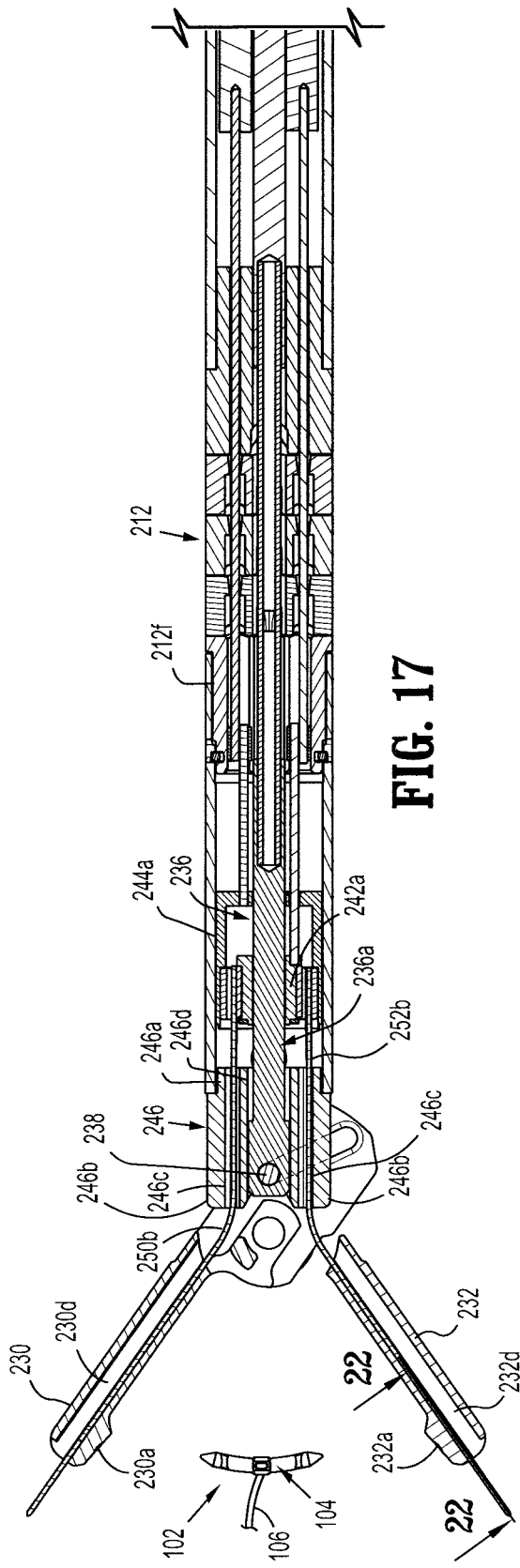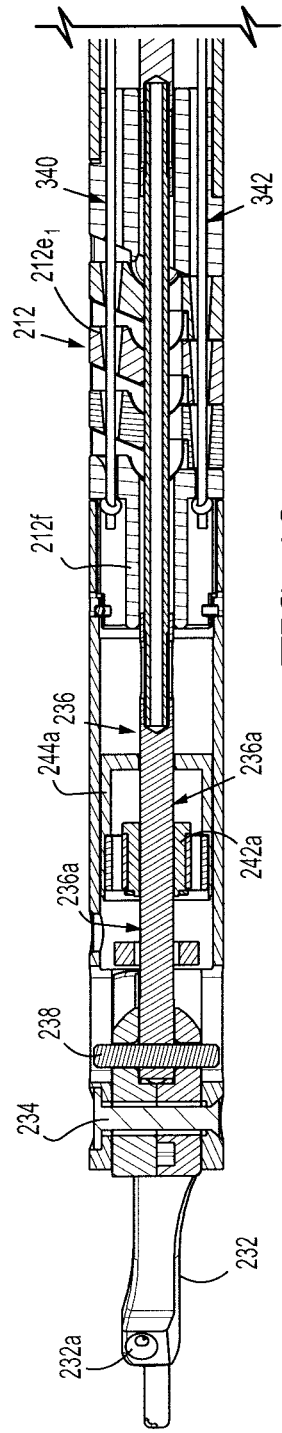

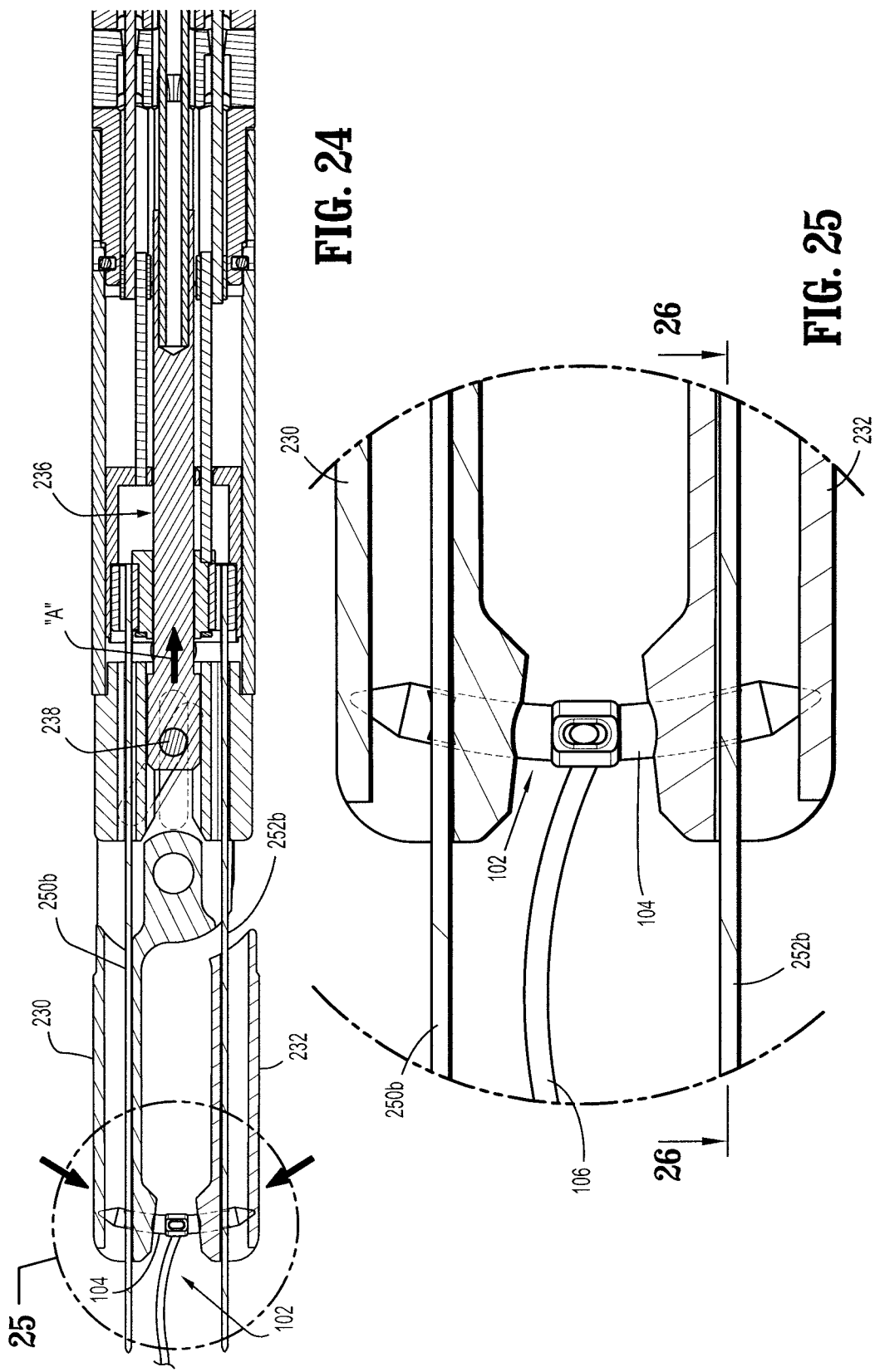

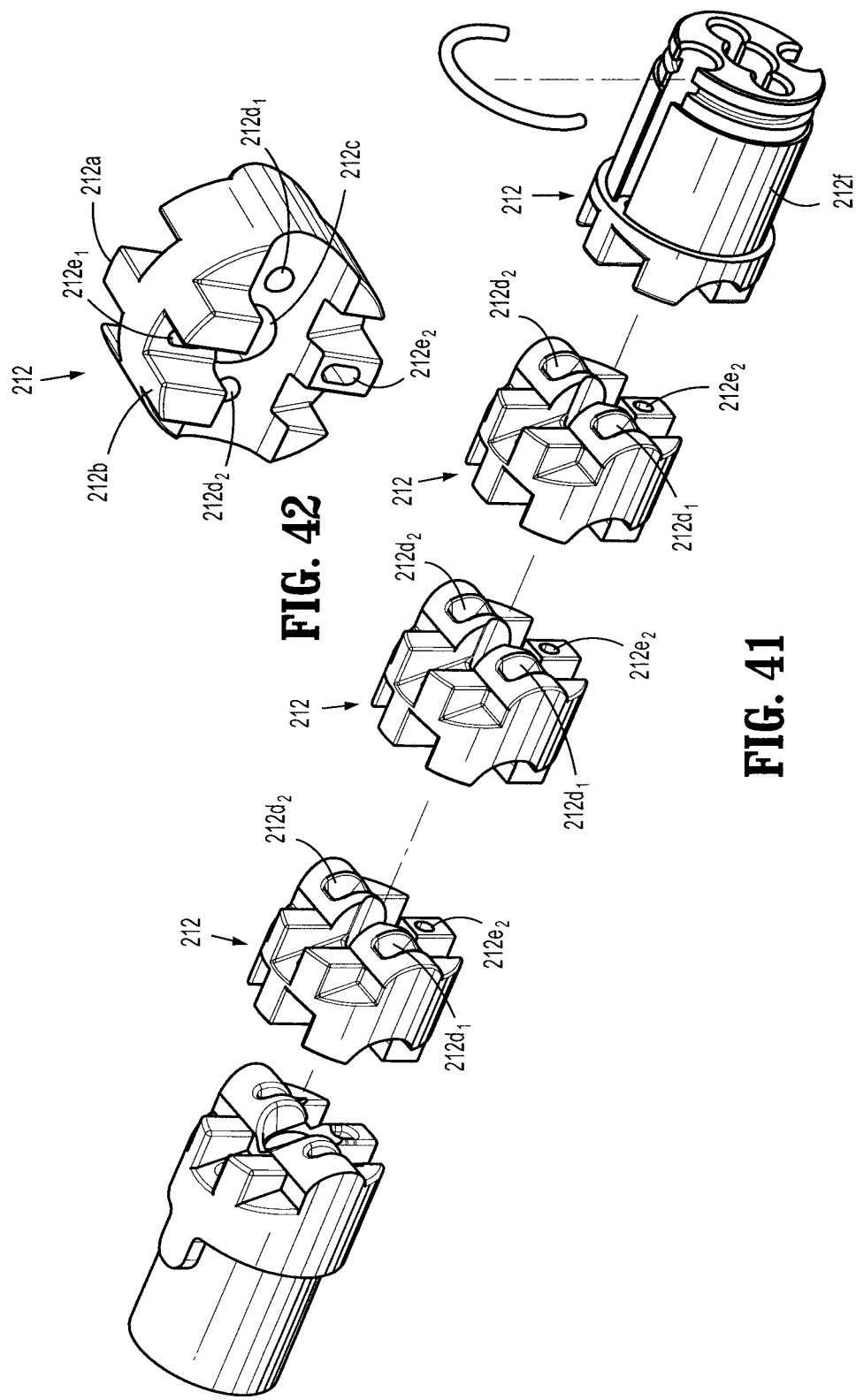

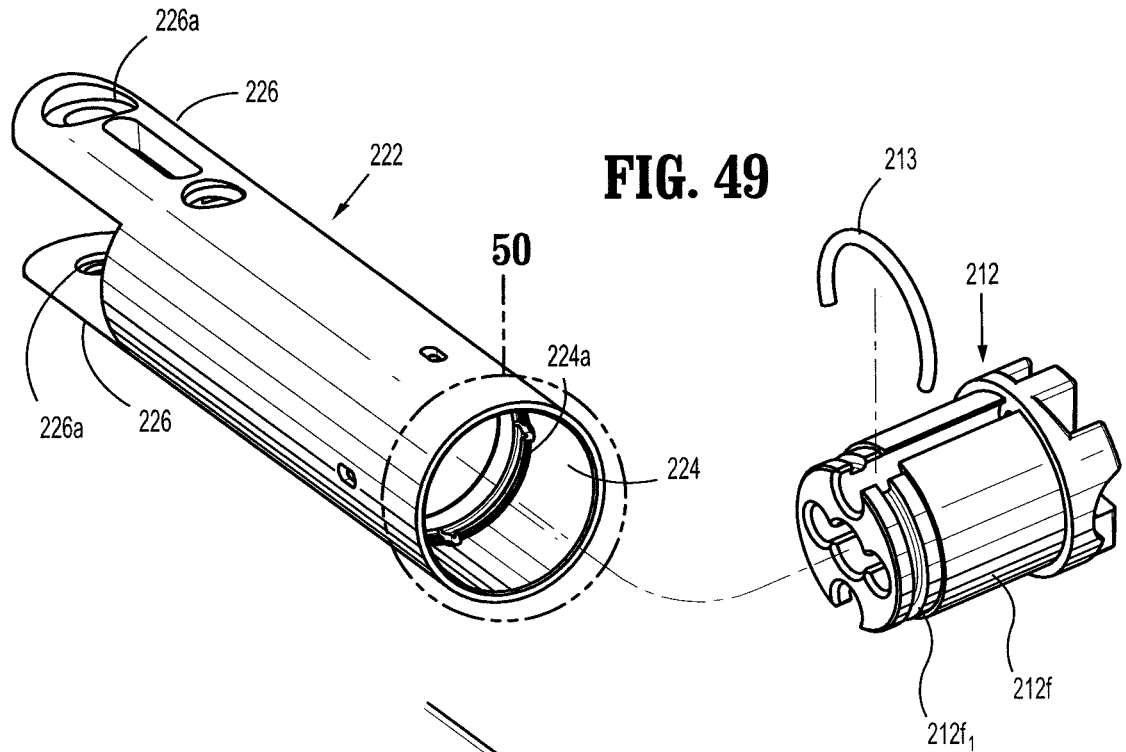
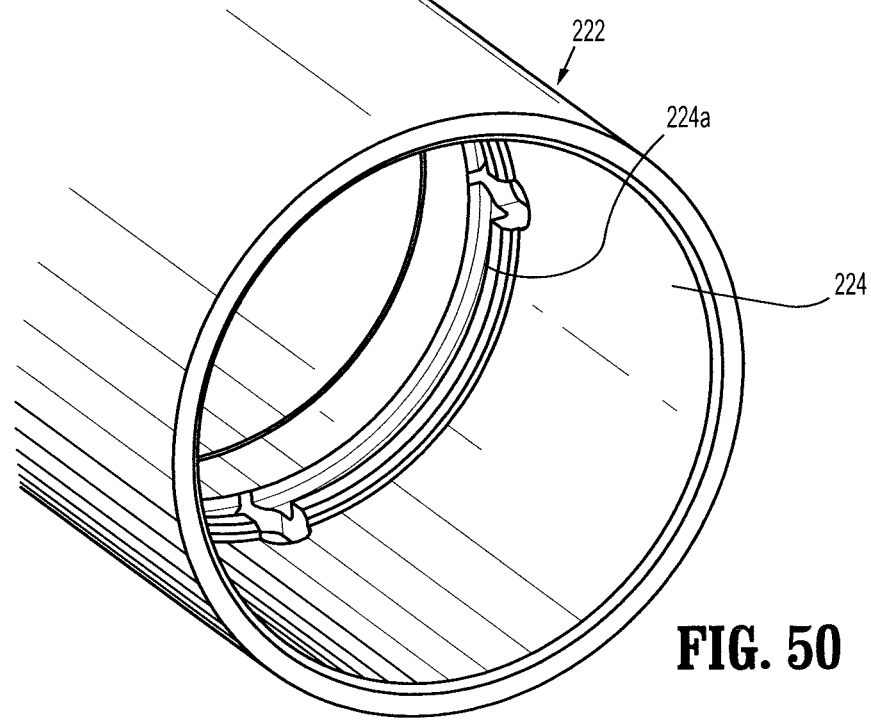

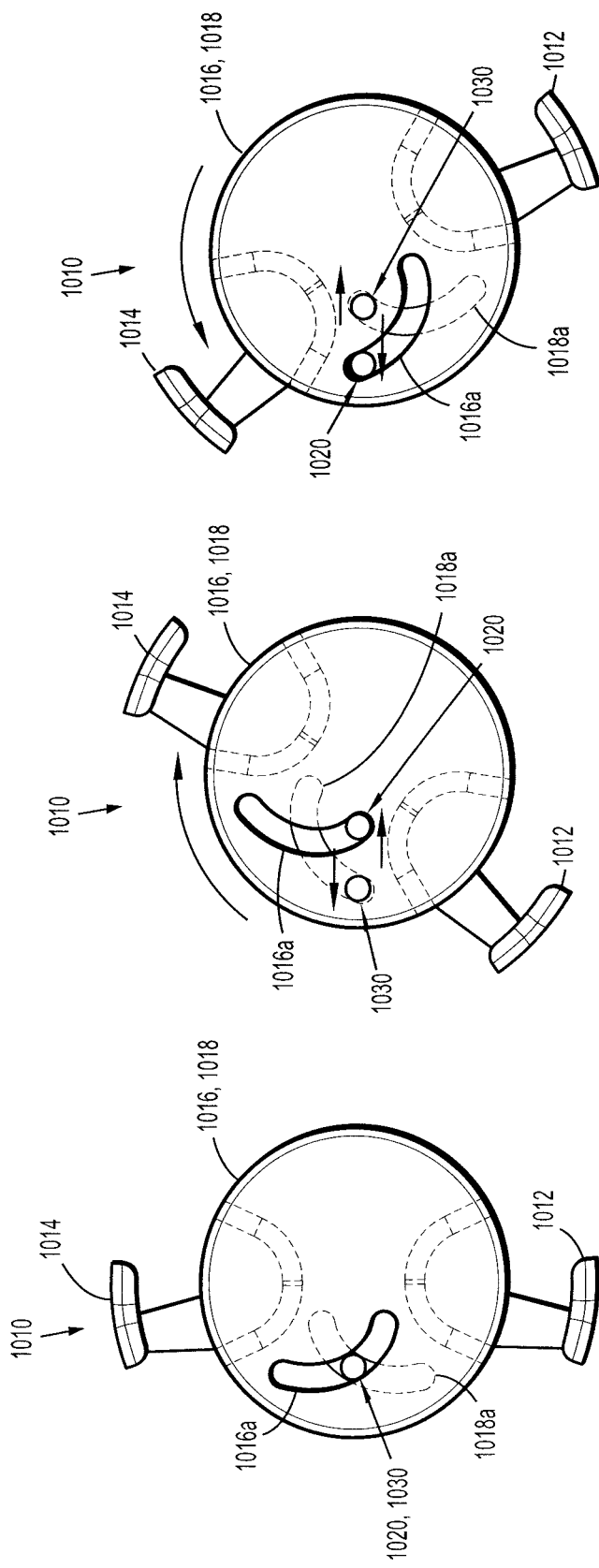

ENDOSCOPIC STITCHING DEVICES

CROSS-REFERENCE TO RELATED APPLICATIONS

The present application is a Continuation Application of U.S. patent application Ser. No. 16/211,398, filed Dec. 6, 2018, which is a Continuation Application of U.S. patent application Ser. No. 15/372,616, filed Dec. 8, 2016, now U.S. Pat. No. 10,413,289, which is a Continuation Application of U.S. patent application Ser. No. 12/896,364, filed on Oct. 1, 2010, now abandoned, which claims the benefit of and priority to each of U.S. Provisional Application Ser. No. 61/304,825, filed on Feb. 16, 2010, and U.S. Provisional Application Ser. No. 61/249,063, filed on Oct. 6, 2009, the entire contents of each of which are incorporated herein by reference.

U.S. patent application Ser. No. 12/896,364 is also a Continuation-in-Part Application of U.S. patent application Ser. No. 12/482,049, filed Jun. 10, 2009, now U.S. Pat. No. 8,628,545, which claims the benefit of and priority to U.S. Provisional Application Ser. No. 61/061,136, filed Jun. 13, 2008, the entire contents of each of which are incorporated herein by reference.

BACKGROUND

Technical Field

The present disclosure relates to devices, systems and methods for endoscopic suturing or stitching and, more particularly, to devices, systems and methods for endoscopic suturing and/or stitching through an access tube or the like.

Background

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and, therefore, the hospital and medical costs can be reduced as well.

One of the truly great advances in recent years to reduce the invasiveness of surgical procedures is endoscopic surgery. Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss. Heat and water loss are greatly reduced as a result of the smaller incisions.

In many surgical procedures, including those involved in endoscopic surgery, it is often necessary to suture bodily organs or tissue. The latter is especially challenging during endoscopic surgery because of the small openings through which the suturing of bodily organs or tissues must be accomplished.

In the past, suturing of bodily organs or tissue through endoscopic surgery was achieved through the use of a sharp metal suture needle which had attached at one of its ends a length of suture material. The surgeon would cause the suture needle to penetrate and pass through bodily tissue, pulling the suture material through the bodily tissue. Once the suture material was pulled through the bodily tissue, the surgeon proceeded to tie a knot in the suture material. The knotting of the suture material allowed the surgeon to adjust the tension on the suture material to accommodate the particular tissue being sutured and control approximation, occlusion, attachment or other conditions of the tissue. The ability to control tension is extremely important to the surgeon regardless of the type of surgical procedure being performed.

However, during endoscopic surgery, knotting of the suture material is time consuming and burdensome due to the difficult maneuvers and manipulation which are required through the small endoscopic openings.

Many attempts have been made to provide devices to overcome the disadvantages of conventional suturing. Such prior art devices have essentially been staples, clips, clamps or other fasteners. However, none of these above listed devices overcome the disadvantages associated with suturing bodily tissue during endoscopic surgery.

Accordingly, there is a need for improvements in suturing devices which overcome the shortcomings and drawbacks of prior art apparatus.

SUMMARY

An endoscopic stitching device consistent with the present invention comprises a handle assembly; an elongate shaft supported by and extending from the handle assembly; and an end effector supported on a distal end of the elongate shaft, the end effector including a neck assembly configured and adapted for articulation in one direction between a substantially linear configuration and an off-axis configuration, and a pair of juxtaposed jaws pivotally associated with one another, wherein each jaw defines a suture needle receiving recess formed in a tissue contacting surface thereof.

In one embodiment, the jaws that are rotatably supported on the end effector for selective rotation about a longitudinal axis thereof when the end effector is in the substantially linear configuration and in the articulated configuration. In another embodiment, the handle assembly supports a rotation assembly configured to transmit an actuation from the handle assembly through the elongate shaft to effectuate rotation of the jaws. The rotation assembly may include a knob rotatably supported on a housing of the handle assembly and operatively connected to a center drive rod assembly, wherein the center drive rod assembly includes a distal end extending through the elongate shaft and connected to the jaws. In some embodiments, at least a portion of the center drive rod assembly is flexible. In an embodiment, the endoscopic stitching device includes a center drive rod assembly translatably supported therein, the center drive rod assembly including a proximal end operatively connected to at least one handle of the handle assembly and a distal end extending through the elongate shaft and operatively connected to the jaws, wherein axial translation of the center drive rod assembly results in opening and closing of the jaws. In an embodiment, the axial rotation of the center drive rod assembly results in rotation of the jaws about a longitudinal axis thereof. In one embodiment, the endoscopic stitching device includes a rotation assembly supported on a housing of the handle assembly and operatively connected to the center drive rod assembly, wherein actuation of the rotation assembly results in concomitant rotation of the center drive rod assembly and the jaws. In an embodiment, at least a portion of a length of the center drive rod assembly is flexible, wherein the flexible portion of the center drive rod assembly will flex upon an articulation of the end effector and enable rotation of the jaws when the end effector is in an articulated condition.

In an embodiment, the end effector further includes a pair of axially translatable needle engaging blades slidably supported, one each, in a respective jaw, each blade having a first position wherein a portion of the blade engages a suture needle when a suture needle is present in suture needle receiving recess formed in the tissue contacting surface of the jaw, and a second position wherein the blade does not engage the suture needle. In accordance with an embodiment, a proximal end of each blade is rotatably supported on a respective barrel of a concentric barrel pair, wherein the blades rotate about the barrels upon a rotation of the jaws.

In some embodiments, a suture needle is loadable into the suture needle receiving recess defined in the jaw when the respective blade is in the second position. In one embodiment, the device includes a loading/unloading assembly supported on the handle assembly and connected to each blade, wherein the loading/unloading assembly is movable between a first position in which the blades are in the first position and a second position in which the blades are in the second position. The loading/unloading assembly may be actuatable in a first direction to move a first blade to the first position and a second blade to the second position, and a second direction to move the first blade in the second direction and the second blade in the first direction.

An endoscopic stitching device of the present invention may also include an articulation assembly supported on the handle assembly and actuatable to articulate the end effector, wherein actuation of the articulation assembly results in articulation of the end effector between the linear configuration and the off-axis configuration. In one embodiment, the articulation assembly includes an articulation cam supported on a housing of the handle assembly and includes first and second cam disks having opposing respective first and second camming channels defined therein, a first pin operably associated with the first camming channel and a first slider configured to longitudinally translate with respect to the housing, and a second pin operably associated with the second camming channel and a second slider configured to longitudinally translate with respect to the housing, the first and second slider secured with respective proximal ends of first and second articulation cables, the distal ends being secured at a location distal of the neck assembly, and wherein the articulation cables are disposed on opposed sides of a center drive rod assembly. The first and second camming channels may be configured to provide equidistant linear motion directly proportional to the angular rotation of the first and second cam disks. The first and second camming channels may have a shape substantially similar to a logarithmic spiral. In some embodiments, each articulation cable remains substantially taut upon translation thereof. In an embodiment, the first and second cam disks are monolithically formed. A torsion spring may operably couple the first and second cam disks. In some embodiments, the articulation assembly includes an articulation knob supported on a housing of the handle assembly, an articulation sleeve operatively connected to the articulation knob and including a pair of oppositely pitched outer helical threads, an articulation collar threadably connected to each helical thread and configured to permit axial translation and prevent rotation thereof, and an articulation cable secured to each articulation collar, wherein each articulation cable includes a first end secured to the respective articulation collar and a second end secured at a location distal of the neck assembly, and wherein the articulation cables are disposed on opposed sides of a center drive rod assembly.

In an embodiment, each articulation cable is operably associated with a seal having first and second lumens extending therethrough, and wherein at least one lumen is configured to receive at least one articulation cable in substantial sealing relationship therewith. At least one of the first and second lumens of the seal may have an arched section. In an embodiment, at least one of the first and second lumens of the seal is repositionable through a plurality of positions including a first position and a second position in response to longitudinal translation of at least one articulation cable therethrough. In an embodiment, at least one lumen of the seal is biased towards at least one of the first or second positions.

In some embodiments, rotation of the articulation knob results in rotation of the articulation sleeve and concomitant axial translation of the articulation collars, wherein axial translation of the articulation collars results in articulation of the end effector. In an embodiment, rotation of the articulation sleeve in a first direction results in relative axial separation of the articulation collars to articulate the end effector in a first direction, and rotation of the articulation sleeve in a second direction results in relative axial separation of the articulation collars to articulate the end effector in a second direction.

In one embodiment, the neck assembly includes a plurality of links in pivotable contact with one another, wherein each link includes a knuckle formed on a first side thereof and a clevis formed on a second side thereof, wherein the knuckle of a first link is operatively connected to a clevis of an adjacent link. In one embodiment, the neck assembly further includes at least one stiffener plate translatably disposed in the plurality of operatively connected links. In one embodiment, one end of the at least one stiffener plate is securely attached to the neck assembly. The knuckles and devises may be configured to enable uni-directional articulation of the neck assembly. The knuckles and devises may be configured to at least partially overlap one another when the neck assembly is in either the substantially linear configuration or the off-axis configuration. An endoscopic stitching device according to the present invention may include a handle assembly that has a pair of handles and a center drive rod connected at a first end to the handles and at a second end to the pair of jaws, wherein actuation of the handles results in axial translation of the center drive rod and concomitant opening and closing of the jaws.

An endoscopic stitching device consistent with an embodiment of the invention includes a handle assembly including a housing; an elongate shaft supported by and extending from the housing; an end effector supported on a distal end of the elongate shaft, the end effector including a neck assembly configured and adapted for articulation in one direction between a substantially linear configuration and an off-axis configuration, and a pair of juxtaposed jaws pivotally associated with one another, wherein each jaw defines a suture needle receiving recess formed in a tissue contacting surface thereof, and wherein the jaws are rotatably supported on the end effector for selective rotation about a longitudinal axis thereof when the end effector is in the substantially linear configuration and in the articulated configuration; an articulation assembly supported on the housing and actuatable to articulate the end effector, wherein actuation of the articulation assembly results in articulation of the end effector between the linear configuration and the off-axis configuration; and a rotation assembly supported on the housing, the rotation assembly being configured to transmit an actuation from the handle assembly through the elongate shaft to effectuate rotation of the jaws.

In an embodiment, the articulation assembly includes an articulation cam supported on a housing of the handle assembly and includes first and second cam disks having opposing respective first and second camming channels defined therein, a first pin operably associated with the first camming channel and a first slider configured to longitudinally translate with respect to the housing, and a second pin operably associated with the second camming channel and a second slider configured to longitudinally translate with respect to the housing, the first and second slider secured with respective proximal ends of first and second articulation cables, the distal ends being secured at a location distal of the neck assembly, and wherein the articulation cables are disposed on opposed sides of a center drive rod assembly. The first and second camming channels may be configured to provide equidistant linear motion directly proportional to the angular rotation of the first and second cam disks. The first and second camming channels may have a shape substantially similar to a logarithmic spiral. In some embodiments, each articulation cable remains substantially taut upon translation thereof. In an embodiment, the first and second cam disks are monolithically formed. A torsion spring may operably couple the first and second cam disks.

In an embodiment, the rotation assembly includes a knob rotatably supported on the housing and operatively connected to a center drive rod assembly, wherein the center drive rod assembly includes a distal end extending through the elongate shaft and connected to the jaws. The rotation assembly may include a beveled gear assembly operatively associated with the knob. The beveled gear assembly may be configured to translate the center drive rod assembly for opening and closing the jaws. The beveled gear assembly may be configured to translate rotational energy to the center drive rod assembly in accordance with at least one of the following ratios 1:1, more than 1:1, or less than 1:1. In an embodiment, the beveled gear assembly includes a sun gear disposed in mechanical cooperation with the knob and operatively associated with first and second beveled gears, the first and second beveled gears being operatively associated with each other. The beveled gear assembly may further include a first beveled gear mount disposed in mechanical cooperation with the first beveled gear and the knob. The second beveled gear may be disposed in mechanical cooperation with the center drive rod assembly. In an embodiment, at least a portion of the center drive rod assembly extending through the neck assembly is flexible.

In one embodiment, the endoscopic stitching device includes a center drive rod assembly at least translatably supported in the housing, the elongate shaft and the end effector, and at least rotatably supported in the elongate shaft and the end effector, the center drive rod assembly including a proximal end operatively connected to at least one handle of the handle assembly and a distal end extending through the elongate shaft and operatively connected to the jaws, wherein axial translation of the center drive rod assembly results in opening and closing of the jaws.

In one embodiment, axial rotation of at least a distal portion of the center drive rod assembly results in rotation of the jaws about a longitudinal axis thereof. In an embodiment, the end effector further includes a pair of axially translatable needle engaging blades slidably supported, one each, in a respective jaw, each blade having a first position wherein a portion of the blade engages a suture needle when a suture needle is present in suture needle receiving recess fanned in the tissue contacting surface of the jaw, and a second position wherein the blade does not engage the suture needle. A proximal end of each blade may be rotatably supported on a respective barrel of a concentric barrel pair, wherein the blades rotated about the barrels upon a rotation of the jaws. A suture needle may be loadable into the suture needle receiving recess defined in the jaw when the respective blade is in the second position.

An endoscopic stitching device consistent with invention may have a loading/unloading assembly supported on the handle assembly and connected to each blade, wherein the loading/unloading assembly is movable between a first position in which the blades are in the first position and a second position in which the blades are in the second position. The loading/unloading assembly may be actuatable in a first direction to move a first blade to the first position and a second blade to the second position, and a second direction to move the first blade in the second direction and the second blade in the first direction.

In an embodiment, the articulation assembly includes an articulation knob supported on the housing of the handle assembly, an articulation sleeve operatively connected to the articulation knob and including a pair of oppositely pitched outer helical threads, an articulation collar threadably connected to each helical thread and configured to permit axial translation and prevent rotation thereof, and an articulation cable secured to each articulation collar, wherein each articulation cable includes a first end secured to the respective articulation collar and a second end secured at a location distal of the neck assembly, and wherein the articulation cables are disposed on opposed sides of a center drive rod assembly.

In an embodiment, each articulation cable is operably associated with a seal having first and second lumens extending therethrough, and wherein at least one lumen is configured to receive at least one articulation cable in substantial sealing relationship therewith. At least one of the first and second lumens of the seal may have an arched section. At least one of the first and second lumens of the seal may be repositionable through a plurality of positions including a first position and a second position in response to longitudinal translation of at least one articulation cable therethrough. In an embodiment, at least one lumen of the seal is biased towards at least one of the first or second positions.

In an embodiment, rotation of the articulation knob results in rotation of the articulation sleeve and concomitant axial translation of the articulation collars, wherein axial translation of the articulation collars results in articulation of the end effector. In one embodiment, rotation of the articulation sleeve in a first direction results in relative axial separation of the articulation collars to articulate the end effector in a first direction, and rotation of the articulation sleeve in a second direction results in relative axial separation of the articulation collars to articulate the end effector in a second direction.

An endoscopic stitching device of the invention may have a neck assembly that includes a plurality of links in pivotable contact with one another, wherein each link includes a knuckle formed on a first side thereof and a clevis formed on a second side thereof, wherein the knuckle of a first link is operatively connected to a clevis of an adjacent link. The neck assembly may further include at least one stiffener plate translatably disposed in the plurality of operatively connected links. One end of the at least one stiffener plate may be securely attached to the neck assembly. The knuckles and devises may be configured to enable uni-directional articulation of the neck assembly. The knuckles and devises may be configured to at least partially overlap one another when the neck assembly is in either the substantially linear configuration or the off-axis configuration.

In an embodiment, the handle assembly includes a pair of handles supported on the housing; and a center drive rod connected at a first end to the handles and at a second end to the pair of jaws, wherein actuation of the handles results in axial translation of the center drive rod and concomitant opening and closing of the jaws.

An endoscopic stitching device consistent with an embodiment of the invention includes a handle assembly; an elongate shaft supported by and extending from the handle assembly; an end effector supported on a distal end of the elongate shaft, the end effector including a neck assembly configured and adapted for articulation in one direction between a substantially linear configuration and an off-axis configuration, and a pair of juxtaposed jaws pivotally associated with one another; and a stiffener plate disposed in the neck assembly and axially extending therein, wherein the stiffener plate defines a plane.

In an embodiment, the plane defined by the stiffener plate is substantially orthogonal to a direction of articulation. The stiffener plate may be substantially flat, wherein the substantially flat stiffener plate is bendable in one direction. The stiffener plate may be translatably disposed in the neck assembly. The end effector may be articulatable in a direction out of the plane defined by the stiffener plate. In an embodiment, the stiffener plate restricts planar articulation of the end effector with respect to the plane defined by the stiffener plate. In one embodiment one end of the stiffener plate includes an anchor portion secured to the neck assembly, wherein the anchor portion may be bifurcated, the bifurcated anchor portion including at least a pair of spaced apart tines. In an embodiment, a free end of the stiffener plate is axially tapered with respect to the width thereof. In some embodiments, the free end of the stiffener plate may be axially tapered with respect to the thickness thereof. In one embodiment, the neck assembly includes a plurality of links in pivotable contact with one another, wherein each link defines a stiffener plate receiving slot for receiving the stiffener plate therethrough. The stiffener plate may extend through the slot of at least one of the links. The stiffener plate, however, may also extend through the slot of all of the links. The stiffener plate may be made of resilient material.

An endoscopic stitching device consistent with an embodiment of the invention includes a handle assembly; an elongate shaft supported by and extending from the handle assembly; an end effector supported on a distal end of the elongate shaft, the end effector including a neck assembly configured and adapted for articulation in one direction between a substantially linear configuration and an off-axis configuration, and a pair of juxtaposed jaws pivotally associated with one another; and a pair of stiffener plates disposed in the neck assembly and axially extending therein, wherein each of the pair of stiffener plates defines a plane.

In one embodiment, the pair of stiffener plates is substantially parallel with one another. The plane defined by each of the pair of stiffener plates may be substantially orthogonal to a direction of articulation. In an embodiment, the pair of stiffener plates is substantially flat, wherein the pair of substantially flat stiffener plates is bendable in one direction. In an embodiment, the pair of stiffener plates is translatably disposed in the neck assembly, wherein the end effector is articulatable in a direction out of the plane defined by the pair of stiffener plates. In one embodiment, the pair of stiffener plates restricts planar articulation of the end effector with respect to the planes defined by the pair of stiffener plates. One end of each of the pair of stiffener plates may include an anchor portion secured to the neck assembly. The anchor portion may be bifurcated, each of the bifurcated anchor portion including at least a pair of spaced apart tines. In an embodiment, a free end of the respective stiffener plate is axially tapered with respect to the width thereof. In another embodiment, a free end of the respective stiffener plate is axially tapered with respect to the thickness thereof. In one embodiment, the neck assembly includes a plurality of links in pivotable contact with one another, wherein each link defines a pair of stiffener plate receiving slots tor receiving the stiffener plates therethrough. The pair of stiffener plates may extend through the slot of at least one of the links. The pair of stiffener plates may also extend through the slot of all of the links. The stiffener plate may be made of resilient material.

DETAILED DESCRIPTION OF THE DRAWINGS

The foregoing objects, features and advantages of the disclosure will become more apparent from a reading of the following description in connection with the accompanying drawings, in which:

FIG. 2 is a top, plan view of the flexible stitching device of FIG. 1;

FIG. 3 is a side, elevational view of the flexible stitching device of FIGS. 1 and 2;

FIG. 4 is a perspective view of an end effector of the flexible stitching device of FIGS. 1-3;

FIG. 5 is a perspective view of a neck assembly of the flexible stitching device of FIGS. 1-3;

FIG. 6 is a perspective view of the neck assembly of FIG. 5, as viewed along line 6-6 of FIG. 5;

FIG. 10 is a perspective view, with parts separated, of a needle load assembly and an end effector articulation assembly of the flexible stitching device;

FIG. 11 is a perspective view of a suture needle assembly of the present disclosure;

FIG. 13 is a perspective view, with parts assembled, of the needle retention assembly of FIG. 12;

FIG. 14 is a longitudinal, cross-sectional view of the needle retention assembly of FIGS. 12 and 13, as taken through 14-14 of FIG. 13;

FIG. 17 is an enlarged view of the indicated area of detail of FIG. 15;

FIG. 18 is an enlarged view of the indicated area of detail of FIG. 16;

FIG. 24 is a cross-sectional view of the end effector assembly, of the flexible stitching device, during the initial actuation of the handle assembly;

FIG. 25 is an enlarged view of the indicated area of detail of FIG. 24;

FIG. 41 is a perspective view, with parts separated, of the neck assembly of the flexible stitching device;

FIG. 42 is a perspective view of a link of the neck assembly of FIG. 41;

FIG. 49 is a perspective view, with parts separated, of the connection of a distal link of the neck portion of the end effector assembly to a distal support member of the end effector assembly;

FIG. 50 is an enlarged view of the indicated area of detail of FIG. 49;

FIG. 76 is a side elevational view of an articulation cam of the articulation assembly of FIGS. 73-75, with the articulation cam being illustrated in a first position;

FIG. 77 is a side elevational view of the articulation cam of FIG. 76 with the articulation cam being illustrated in a second position;

FIG. 78 is a side elevational view of the articulation cam of FIGS. 76-77 with the articulation cam being illustrated in a third position;

DETAILED DESCRIPTION

Figure 1:
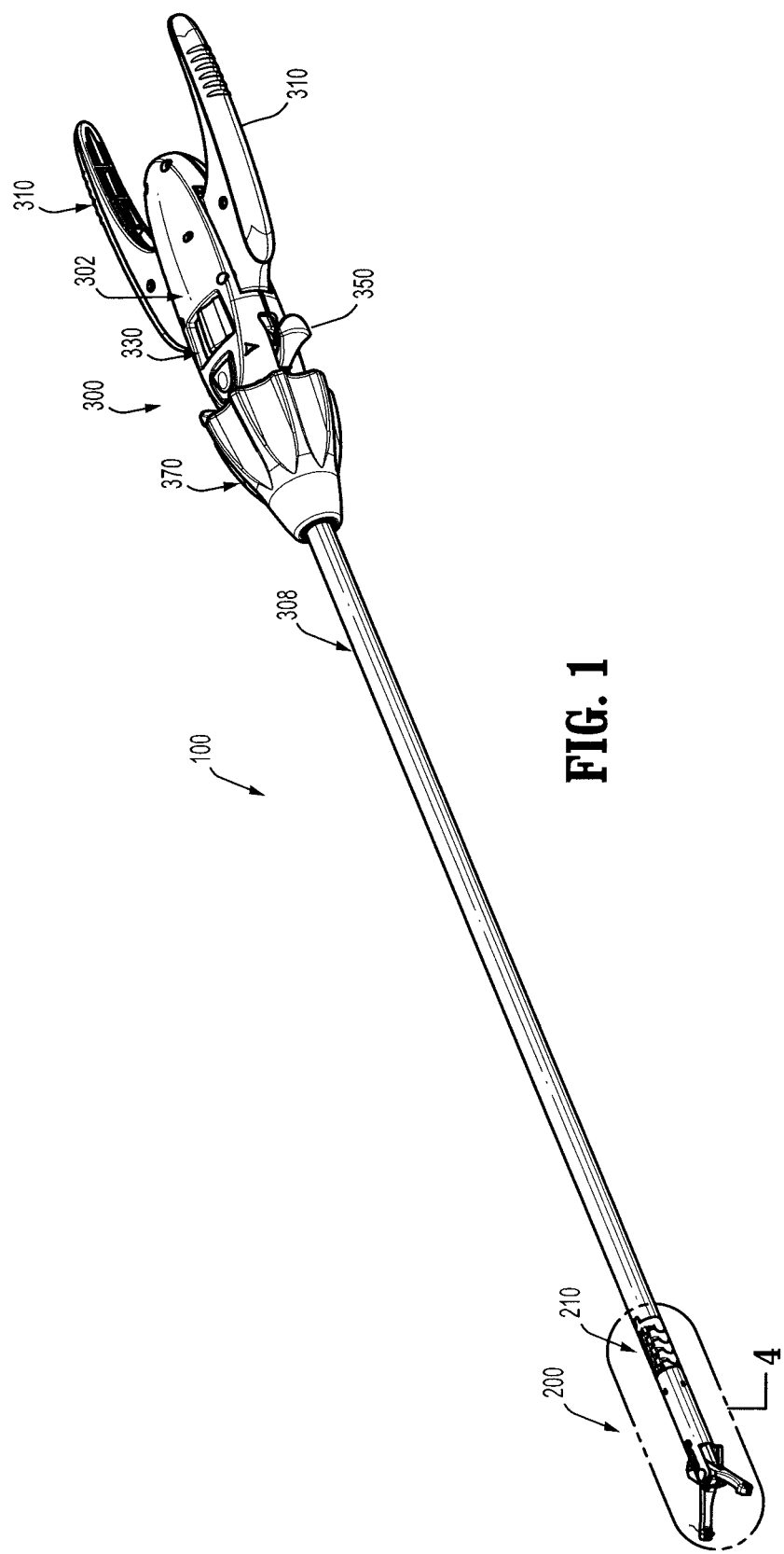
FIG. 1 is a perspective view of a flexible stitching device according to an embodiment of the present disclosure.
Figure 7:
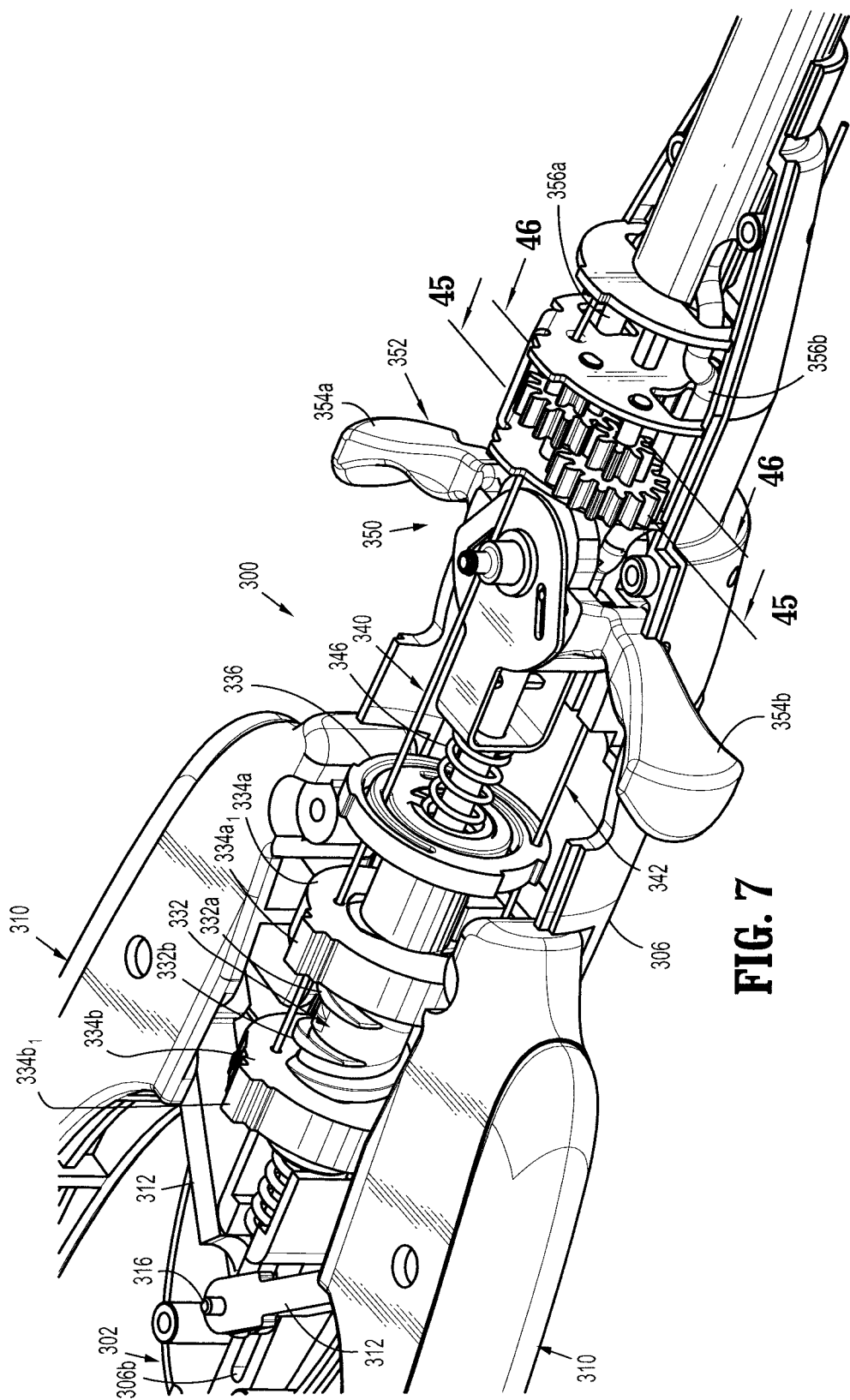
FIG. 7 is a top, right-side, perspective view of a handle assembly of the flexible stitching device, illustrated with a housing half-section removed therefrom.
Figure 8:
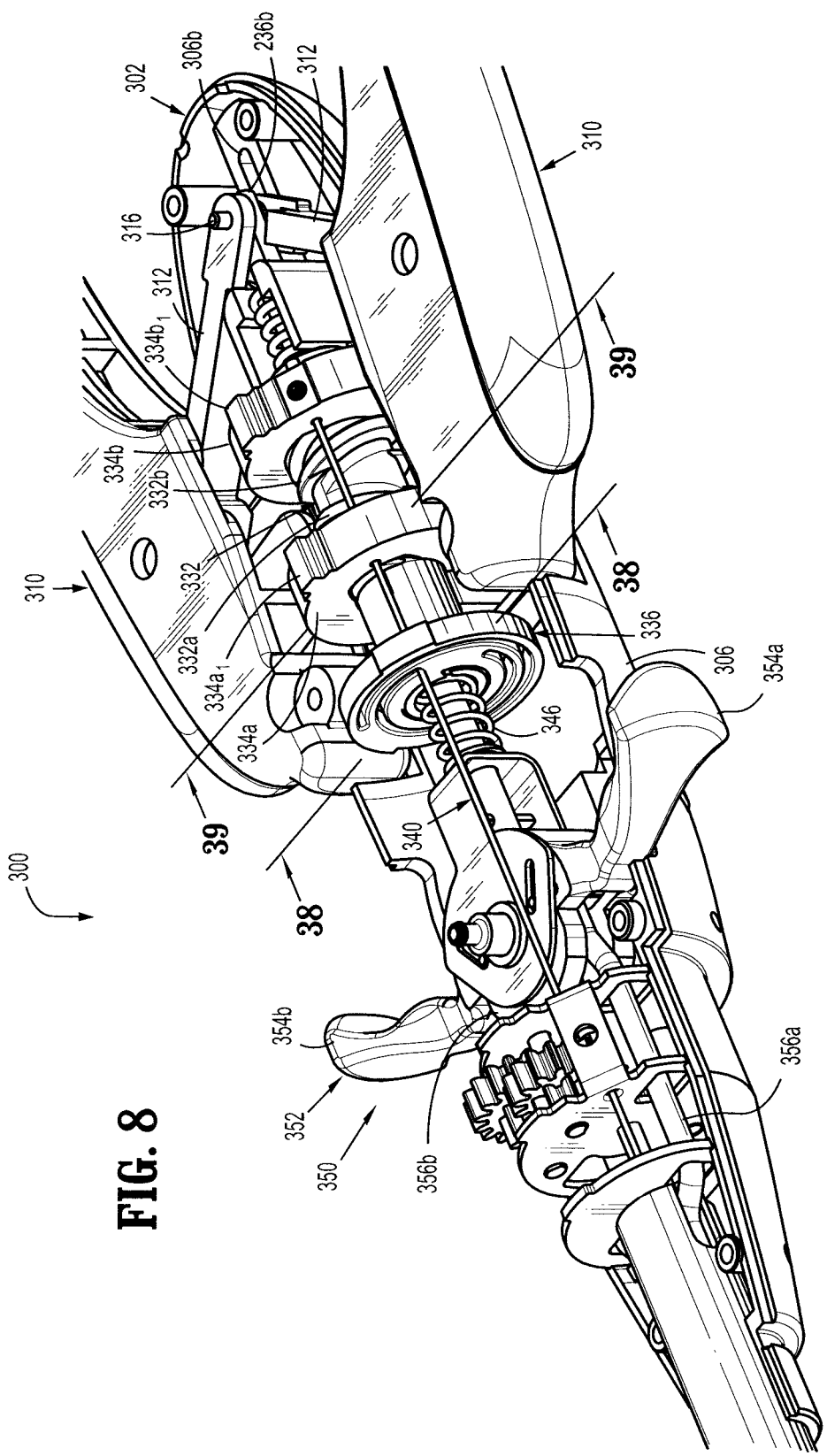
FIG. 8 is a top, left-side, perspective view of a handle assembly of the flexible stitching device, illustrated with a housing half-section removed therefrom.

The present disclosure relates to devices, systems and methods for endoscopic, laparoscopic, endoluminal, and/or transluminal suturing. In one embodiment, for example, such a device comprises a handle. Handle assembly or other suitable actuating mechanism (e.g., robot, etc.) connected to a proximal end of a flexible, elongated body portion. A neck assembly operatively supported on a distal end of the flexible, elongated body portion allows an end effector, operatively supported at a distal end of the neck assembly, to articulate in response to actuation of articulation cables. The end effector includes a suture needle and a pair of jaws. In operation, the suture needle is passed back and forth through tissue from one jaw to the other. The device is adapted to be placed in a lumen of a flexible endoscope and then inserted into a natural orifice of a patient and transited endoluminally through the anatomy of the natural lumen to a treatment site within or outside the natural lumen.

In the drawings and in the description which follow, the term "proximal", as is traditional, will refer to the end of the device which is closest to the operator, while the term "distal" will refer to the end of the device which is furthest from the operator.

Referring now in specific detail to the drawings, in which like reference numbers identify similar or identical elements, FIGS. 1-3 illustrate a flexible stitching device, shown generally at 100. Stitching device 100 is adapted to be particularly useful in endoscopic or laparoscopic procedures wherein an endoscopic portion of the stitching device, i.e., end effector, is insertable into an operative site, via a cannula assembly or the like (not shown).

As seen in FIGS. 1-3, stitching device 100 includes an end effector 200 of supportable on or extends from a handle assembly 300 and/or a distal end of an elongate tubular body portion 308 extending distally from handle assembly 300.

As seen in FIGS. 1-6, 9, 41 and 42, end effector 200 includes a neck assembly 210 supported on a distal end of shaft 308 extending from handle assembly 300, and a tool or jaw assembly 220 supported on a distal end of neck assembly 210. Neck assembly 210 includes a plurality of links 212 each including a proximal knuckle 212a and a distal clevis 212b formed therewith. As seen in FIGS. 41 and 42, each knuckle 212a operatively engages a clevis 212b of an adjacent link 212. Each link 212 defines a central lumen 212c (see FIG. 42) formed therein and two pair of opposed lumen 212d1, 212d2 and 212e1, 212e2, respectively, formed on either side of central lumen 212c. A pair of articulation cables 340, 342, slidably extend through respective lumens 212e1, 212e2, of links 212.

Links 212 are configured to enable end effector 200 to move between a substantially linear configuration and a substantially angled, off-axis or articulated configuration. Links 212 are also configured so as to permit end effector 200 to be articulated in solely a single direction. For example, as seen in FIGS. 5 and 6, when end effector 200 is in a linear condition, the knuckles and devises on a first side of central lumen 212c are fully seated within one another, and the knuckles and devises on a second side of central lumen 212c are not fully seated within one another, thereby permitting end effector 200 to be articulated in the direction of the not fully seated side of central lumen 212c. Moreover, the knuckles and corresponding devises are dimensioned such that when end effector 200 is in the substantially linear configuration, the knuckles and the corresponding devises on the not fully seated side of central lumen 212c are at least aligned with one another or at least partially overlap one another. In this manner, the possibility of tissue, vessels or other body structures getting caught or pinched therebetween is reduced.

Operation of neck assembly 210 to articulate end effector 200 thereabout, will be discussed in greater detail below.

As seen in FIGS. 1-4, 9, 49 and 50, jaw assembly 220 of end effector 200 includes a jaw support member 222, and a pair of jaws 230, 232 mounted for pivotable movement on jaw support member 222. Jaw support member 222 defines a lumen 224 in a proximal end thereof and a pair of spaced apart arms 226 in a distal end thereof. As seen in FIG. 49, lumen 224 is configured and dimensioned to receive a stem 212f extending from a distal-most link 212 of neck assembly 210.

As seen in FIGS. 49-52, jaw support member 222 defines an annular groove 224a formed in a surface of lumen 224 thereof and stem 212f defines an annular race 212f1 formed in an outer surface thereof. An annular groove 224a formed in a surface of lumen 224 of jaw support member 222 and annular race 212f1 formed in the outer surface of stem 212f are in registration with one another when stem 212f is connected to jaw support member 222. A ring 213 is disposed within annular groove 224a formed in a surface of lumen 224 of jaw support member 222 and annular race 212f, formed in the outer surface of stem 212f to thereby maintain stem 212f connected to jaw support member 222 and permit rotation of jaw support member 222 relative to stem 212f.

As seen in FIGS. 4, 17 and 18, each jaw 230, 232 includes a needle receiving recess 230a, 232a, respectively, configured to surround and hold at least a portion of a needle 104 of a suture needle assembly 102 disposed therein substantially perpendicular to tissue engaging surfaces thereof. As seen in FIG. 11, needle 104 includes a groove 104a formed near each end thereof. A suture 106 may be secured to surgical needle 104 at a location between grooves 104a.

Suture 106 of suture needle assembly 104 may comprise a one-way or barbed suture, wherein the suture includes an elongated body having a plurality of barbs extending therefrom. The barbs are oriented in such a way that the barbs cause the suture to resist movement in an opposite direction relative to the direction in which the barb faces.

Suitable sutures for use with suture needle assembly 104 include, and are not limited to, those sutures described and disclosed in U.S. Pat. Nos. 3,123,077; 5,931,855; and U.S. Patent Publication No. 2004/0060409, filed on Sep. 30, 2002, the entire content of each of which being incorporated herein by reference.

Jaws 230, 232 are pivotably mounted on support member 222 by means of a jaw pivot pin 234 which extends through holes 226a formed in arms 226 of support member 222 and respective pivot holes 230b, 232b formed in jaws 230, 232. To move jaws 230, 232 between an open position and a closed position there is provided an axially or longitudinally movable center drive rod assembly 236 having a camming pin 238 mounted at a distal end of a center drive rod distal portion 236a. Camming pin 238 rides in and engages angled camming slots 230c, 232c formed in respective jaws 230, 232 such that axial or longitudinal movement of center rod assembly 236 causes jaws 230, 232 to be cammed between open and closed positions.

Jaw assembly 220 includes a drive assembly 240 slidably and rotatably disposed within lumen 224 of support member 222. As seen in FIGS. 9 and 12-14, drive assembly 240 includes an inner drive assembly 242 and an outer drive assembly 244. Inner drive assembly 242 includes an inner barrel or collar 242a defining a lumen 242b therethrough. Lumen 242b is configured to slidably and rotatably receive center drive rod distal portion 236a of center drive rod assembly 236 therein. Inner drive assembly 242 further includes a cuff 250a slidably and/or rotatably supported on inner barrel 242a, and a first blade 250b extending from cuff 250a. Blade 250b extends from cuff 250a in a direction substantially parallel to a central longitudinal axis of lumen 242b of inner barrel 242a.

As seen in FIGS. 9 and 12-14, outer drive assembly 244 includes an outer barrel or collar 244a defining a lumen 244b therethrough and an annular recess 244c formed in a surface of lumen 244b. Lumen 244b is configured to slidably and rotatably receive inner barrel 242a therein, such that inner barrel 242a is nested within lumen 244b of outer barrel 244a. Outer drive assembly 244 further includes a cuff 252a slidably and/or rotatably supported in annular recess 244c, and a second blade 252b extending from ring 244d. Blade 252b extends from cuff 252a in a direction substantially parallel to a central longitudinal axis of lumen 244b of outer barrel 244a.

Jaw assembly 220 further includes a clevis 246 disposed between arms 226 of support member 222. Clevis 246 includes a pair of spaced apart arms 246b extending from a base 246a. Each arm 246b defines a lumen 246c therethrough. Clevis 246 defines a central aperture 246d formed in base 246a. Arms 246b are spaced apart an amount sufficient and central aperture 246d of base 246b is dimensioned so as to slidably and rotatably receive distal portion 236a of center rod assembly 236 therethrough.

Jaw assembly 220, as discussed above, further includes a pair of needle engaging members or blades 250b, 252b which are slidably supported within a respective lumen 246c of arms 246b of clevis 246. Each blade 250b, 252b includes a distal end slidably extending into blade receiving channels 230d, 232d (see FIG. 17) of respective jaws 230, 232. Each blade 250b, 252b is resilient so as to flex or bend as jaws 230, 232 are opened and closed and still translate relative thereto when jaws 230, 232 are in either the open or closed condition.

In operation, as inner drive assembly 242 and outer drive assembly 244 are translated, in an axial direction, relative to one another. Blades 250b, 252b are also translated with respect to one another.

Turning now to FIGS. 1-3 and 7-10, a detailed discussion of handle assembly 300 is provided. Handle assembly 300 includes a housing 302 having an upper housing half 304 and a lower housing half 306. Handle assembly 300 further includes a pair of handles 310 pivotably secured to housing 302 and extending outwardly therefrom.

Housing halves 304, 306 of flexible stitching device may be joined together by snap-fit engagement or by suitable fasteners (e.g., screws) or the like. Housing 302 defines a window 304a, 306a respectively formed in housing halves 304, 306. Windows 304a, 306a of housing halves 304, 306 are dimensioned to receive and provide access to an articulation assembly 330.

Figure 9:
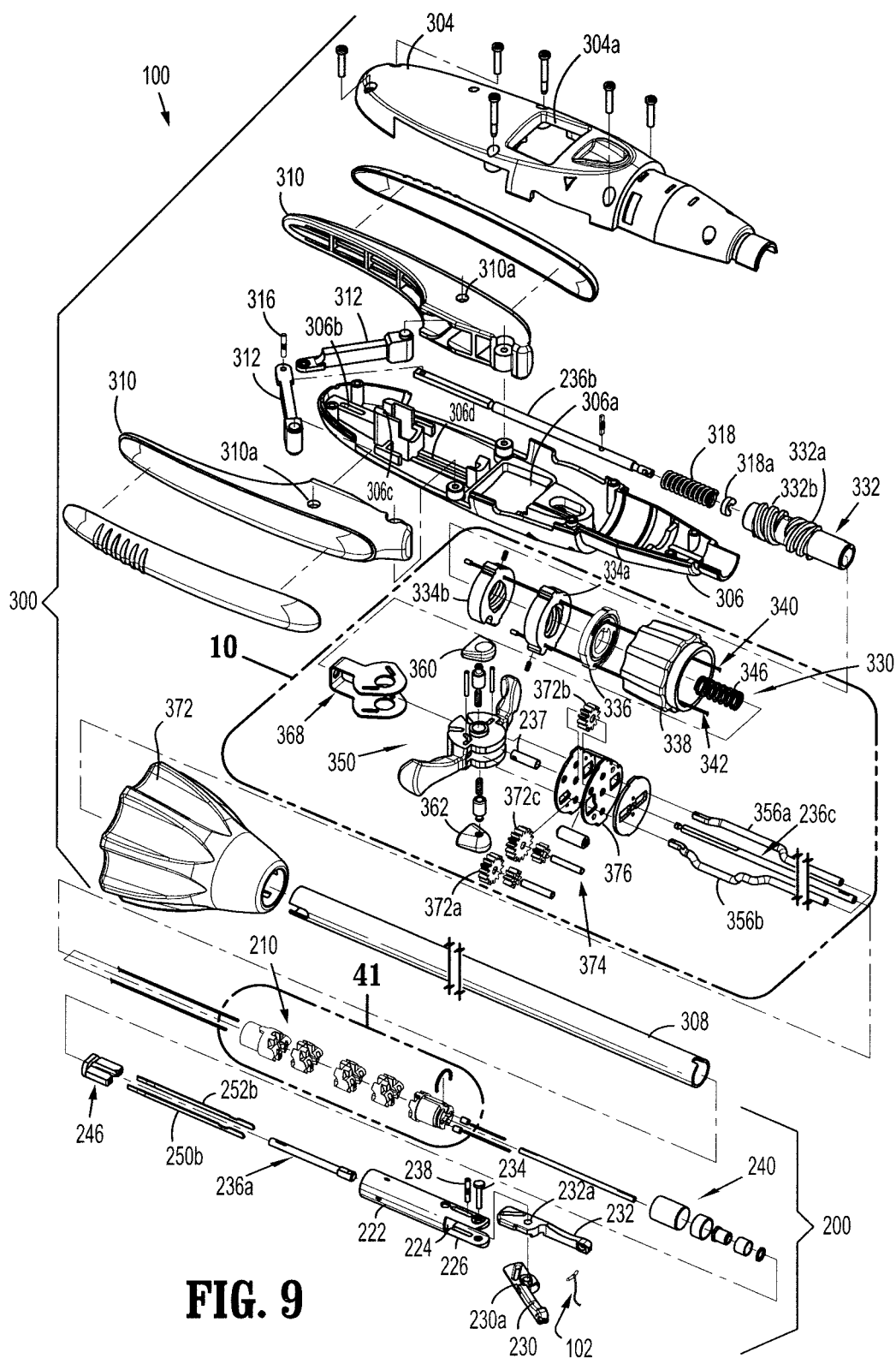
FIG. 9 is a perspective view, with parts separated, of the flexible stitching device.

As seen in FIG. 9, handles 310 are secured to housing 302 at handle pivot posts. Handle assembly 300 includes a link member 312 having a first end pivotably connected to each handle 310 at a pivot point 310a formed in a respective handle 310 and a second end pivotally connected to one another and pivotally connected to a proximal portion 236b of center drive rod assembly 236 via a drive pin 316. Each end of drive pin 316 is slidably received in a respective elongate channel 304b, 306b of housing halves 304, 306. In use, as will be described in greater detail below, as handles 310 are squeezed, link members 312 push center drive rod assembly 236 proximally via drive pin 316.

As mentioned above, handle assembly 300 includes a center drive rod assembly 236 translatably supported in housing 302. Handle assembly 300 includes a biasing member 318, in the form of a return spring, supported on proximal portion 236b of center drive rod assembly 236 and held in place between a surface 306c formed in lower housing half 306 and a retaining clip 318a connected to proximal portion 236b of center drive rod assembly 236.

Figure 47:
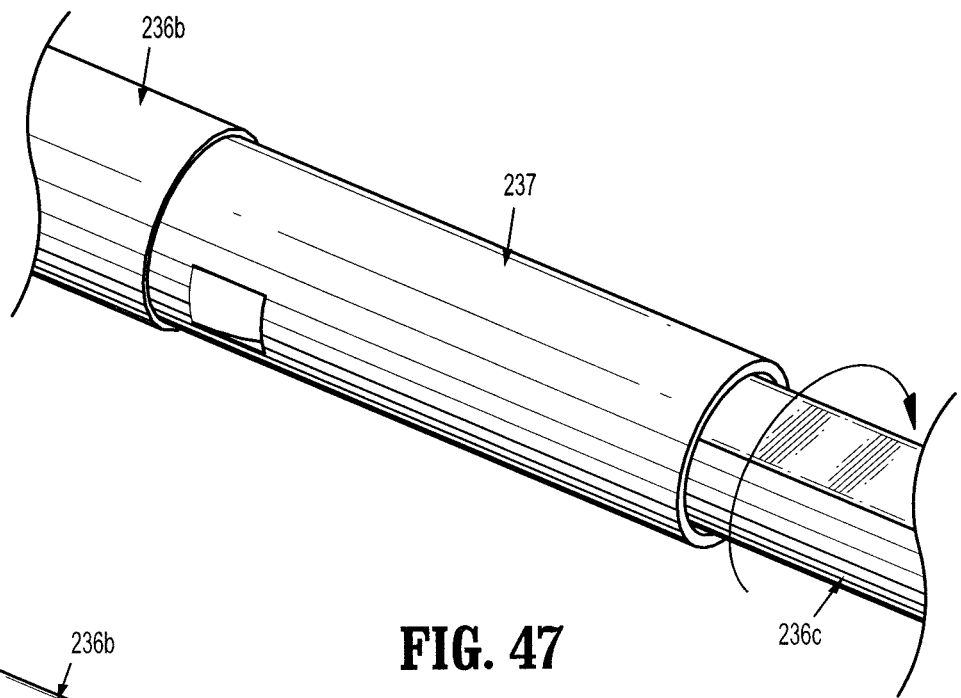
FIG. 47 is a perspective view illustrating the connection of a distal center rod and a proximal center rod, including a coupling sleeve.
Figure 48:
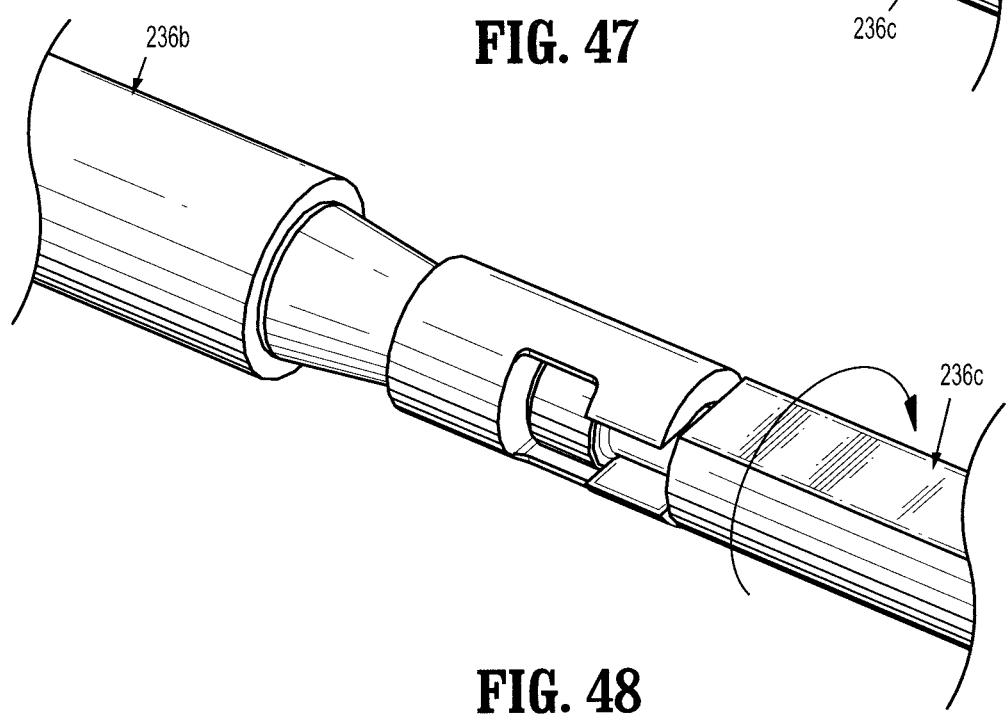
FIG. 48 is a perspective view illustrating the connection of the distal center rod and the proximal center rod, with the coupling sleeve removed therefrom.
Figure 51:
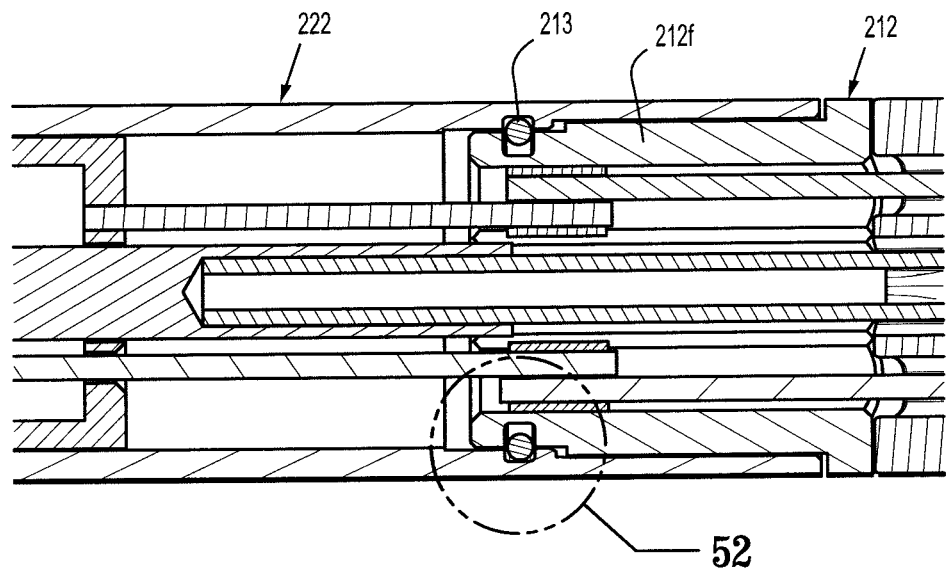
FIG. 51 is a longitudinal cross-sectional view illustrating the connection of the distal link of the neck assembly the distal support member.
Figure 52:
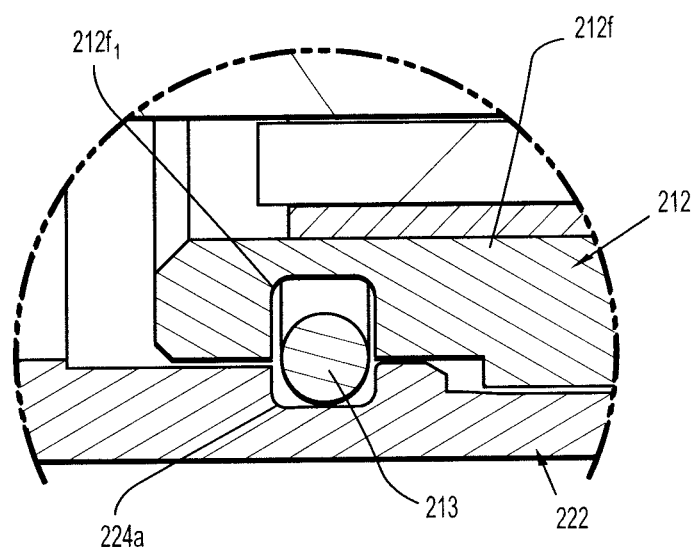
FIG. 52 is an enlarged view of the indicated area of detail of FIG. 51.
Figure 53:
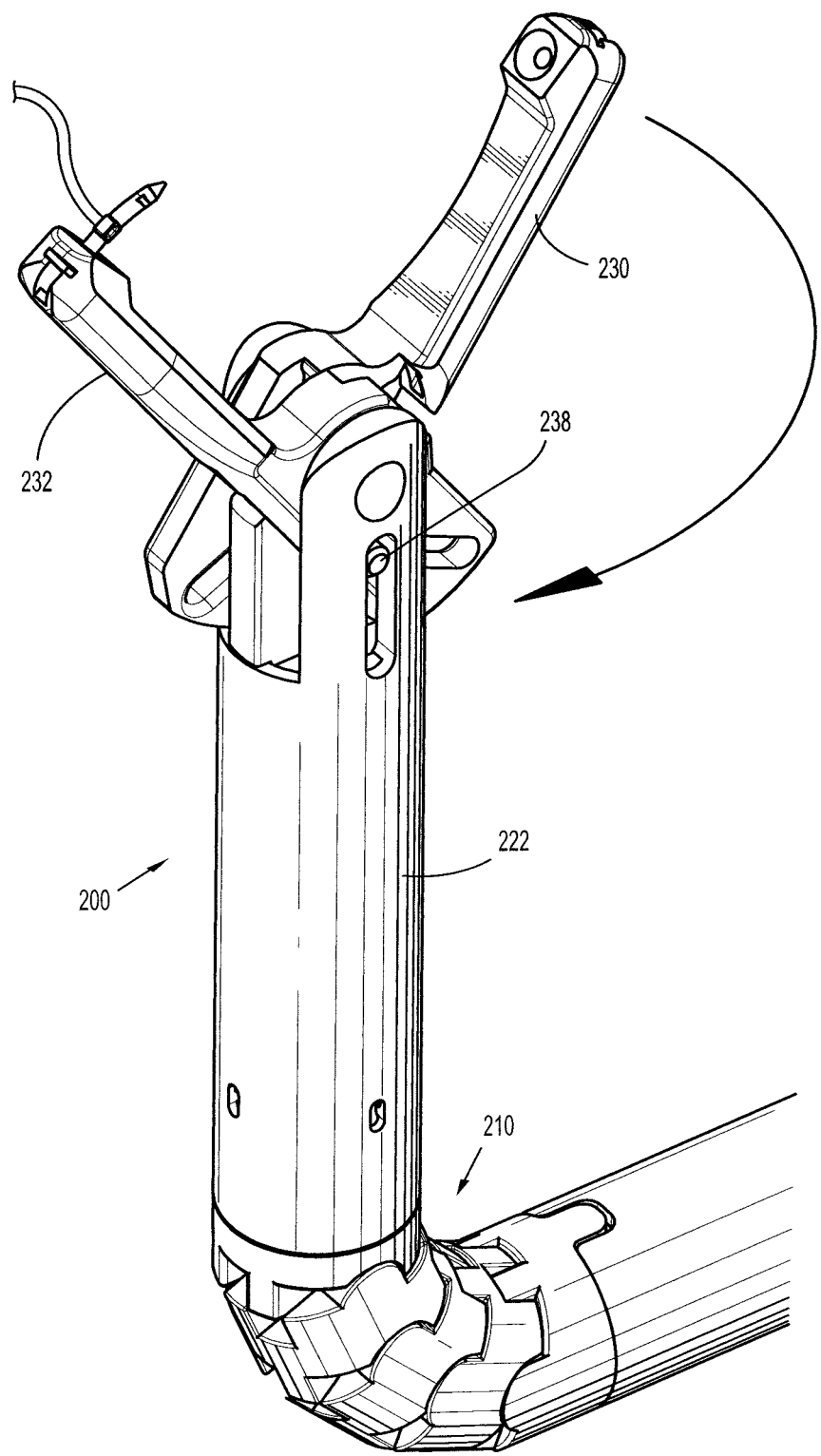
FIG. 53 is a perspective view of the end effector assembly, illustrating a rotation thereof.
Figure 54:
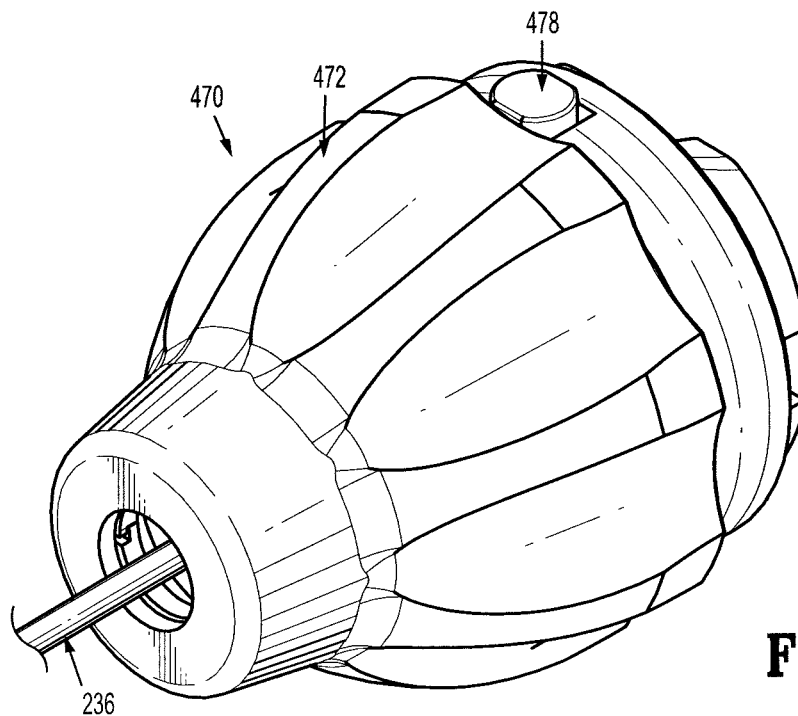
FIG. 54 is a front, perspective view of an end effector rotation assembly according to another embodiment of the present disclosure.
Figure 55:
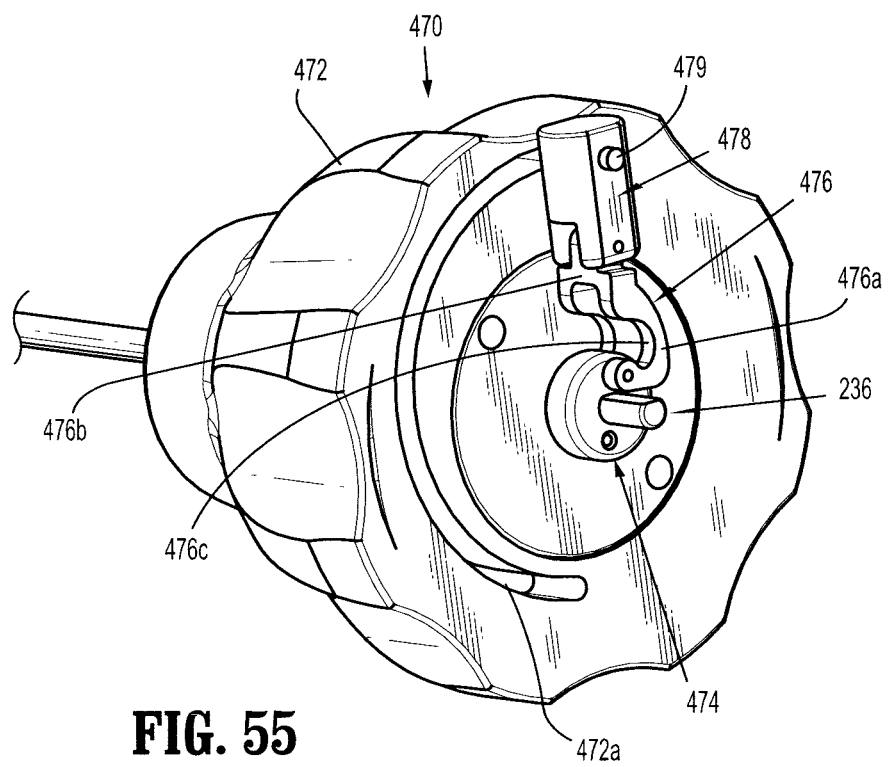
FIG. 55 is a rear, perspective view of the end effector rotation assembly of FIG. 54.
Figure 56:
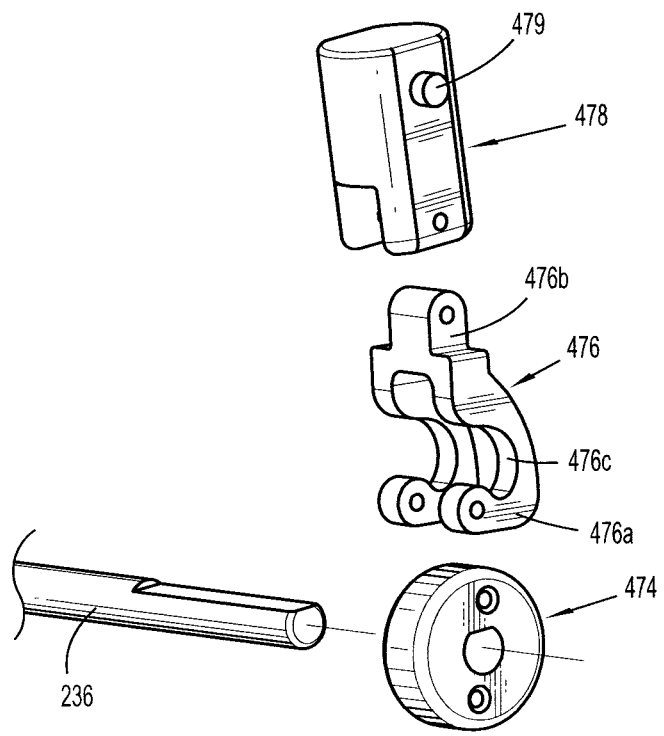
FIG. 56 is a perspective view, with parts separated, of the end effector rotation assembly of FIGS. 54 and 55.
Figure 57:
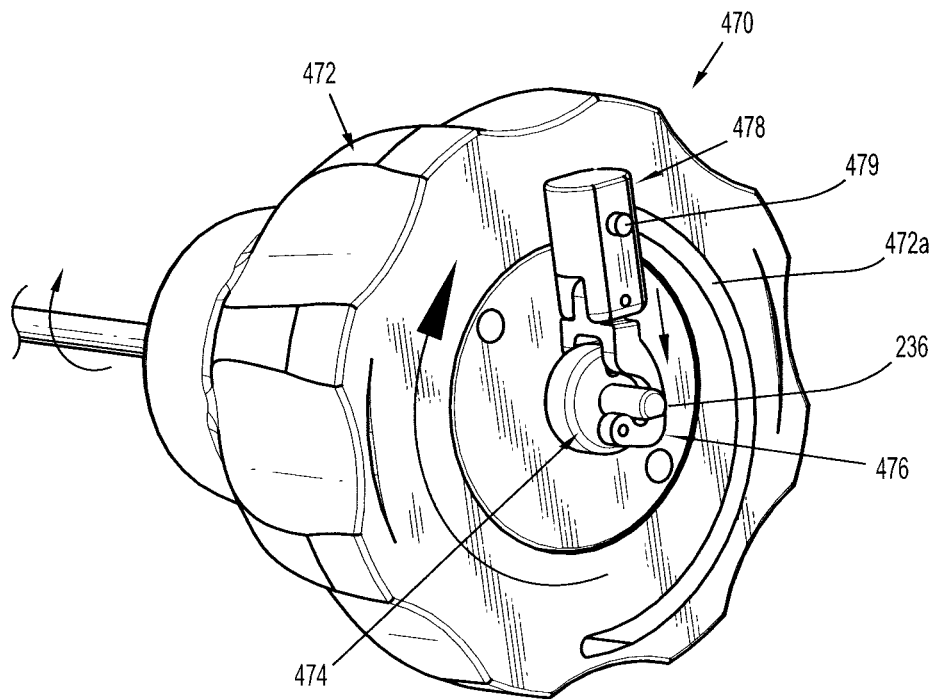
FIG. 57 is a rear, perspective view of the end effector rotation assembly of FIGS. 54-56, illustrating an operation thereof.
Figure 58:
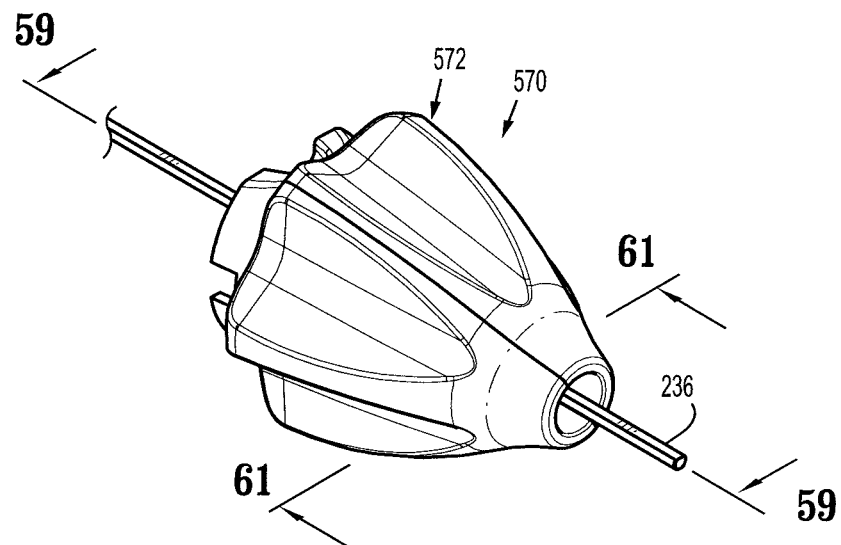
FIG. 58 is a front, perspective view of an end effector rotation assembly according to still another embodiment of the present disclosure.
Figure 59:
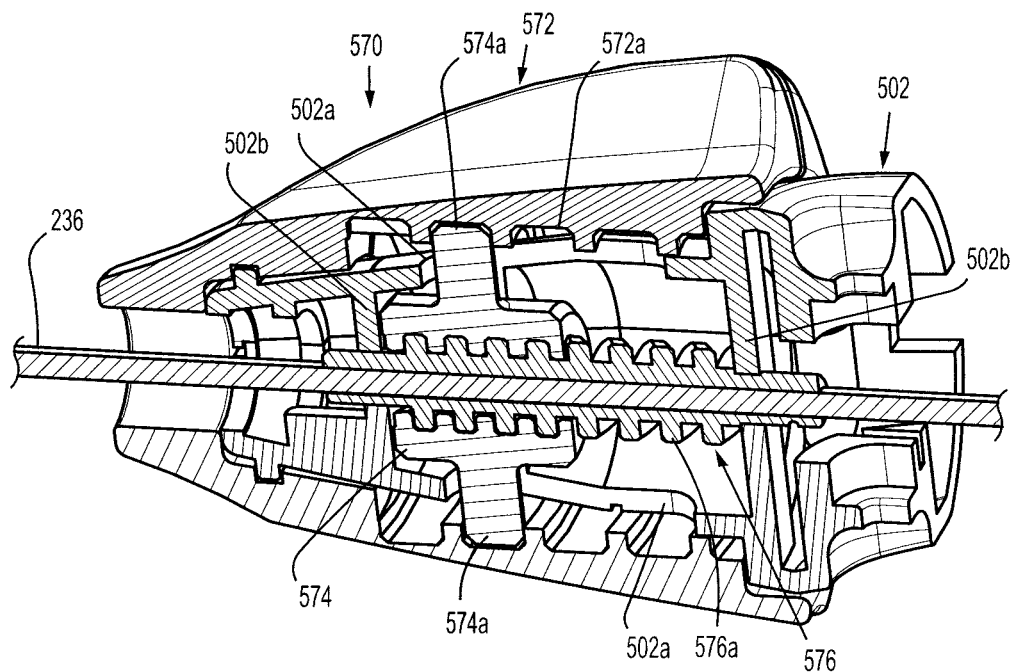
FIG. 59 is a cross-sectional view of the end effector rotation assembly of FIG. 58, as taken through 59-59 of FIG. 58.
Figure 60:
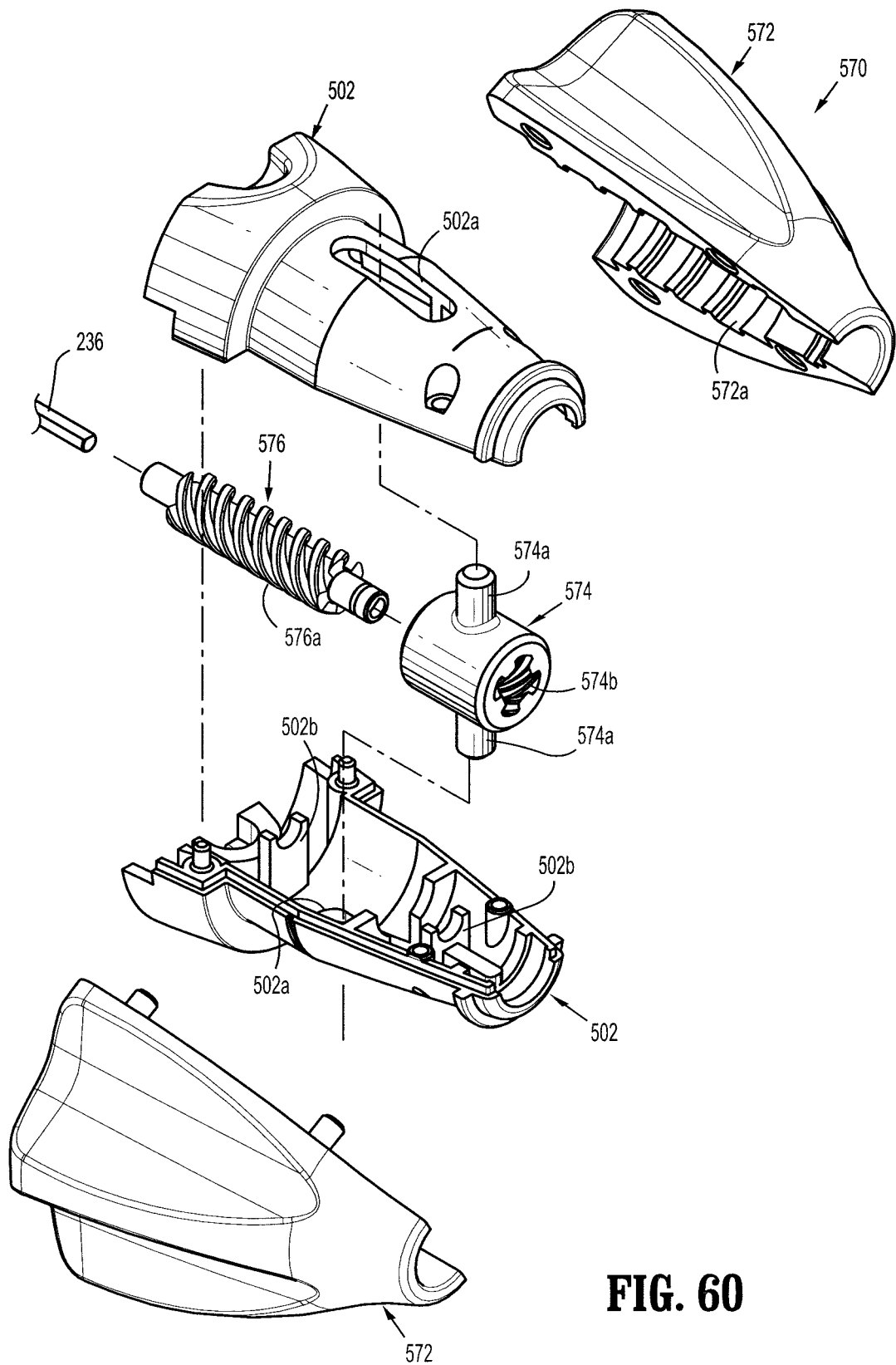
FIG. 60 is a perspective view, with parts separated, of the end effector rotation assembly of FIGS. 58 and 59.
Figure 61:
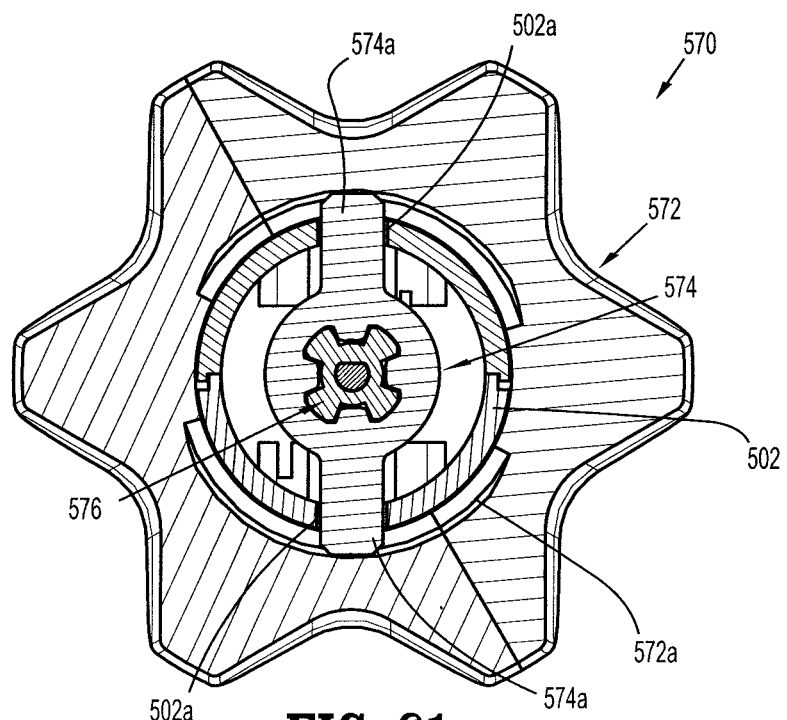
FIG. 61 is a cross-sectional view of the end effector rotation assembly of FIGS. 58-60, as taken through 61-61 of FIG. 58.

As seen in FIGS. 9, 47 and 48, a distal end proximal portion 236b of center drive rod assembly 236 is rotatably connected to a proximal end of an intermediate portion 236c of center drive rod assembly 236. In this manner, intermediate portion 236c of center drive rod assembly 236 is free to rotate relative to proximal portion 236b of center drive rod assembly 236. A sleeve 237 may be provided to maintain intermediate portion 236c of center drive rod assembly 236 and proximal portion 236b of center drive rod assembly 236 connected to one another. Intermediate portion 236c of center drive rod assembly 236 is connected to distal portion 236a of center drive rod assembly 236. In operation, as proximal portion 236b of center drive rod assembly 236 is translated upon the actuation of handles 310, said translation is transmitted to intermediate portion 236c and distal portion 236a of center drive rod assembly 236. As described above, as distal portion 236a of center drive rod assembly 236 is translated camming pin 238, mounted to distal portion 236a of center drive rod assembly 236, rides in and engages angled camming slots 230c, 232c formed in respective jaws 230, 232 to cause jaws 230, 232 to be cammed between open and closed positions.

Handle assembly 300 further includes an articulation assembly 330 rotatably supported in housing 302. Articulation assembly 330 includes a threaded articulation sleeve 332 rotatably supported and axially fixed on center drive rod 314, at a location distal of biasing member 318. Threaded articulation sleeve 332 defines a distal thread and a proximal thread 332a, 332b, respectively.

As seen in FIGS. 9, 10, 19 and 20, articulation assembly 330 further includes a distal articulation collar 334a and a proximal articulation collar 334b operatively connected to a respective thread 332a, 332b of articulation sleeve 332. Each collar 334a, 334b defines a pair of radially extending tabs 334a1, 334b1, respectively, that are in slidably engagement in elongate slots 304d, 306d (see FIG. 20) of upper and lower housing halves 304, 306, respectively. Threads 332a, 332b of articulation sleeve 332 and respective threads of distal and proximal articulation collars 334a, 334b are configured such that rotation of articulation sleeve 332 results in either approximation of distal and proximal articulation collars 334a, 334b relative to one another when articulation sleeve 332 is rotated in a first direction or separation of distal and proximal articulation collars 334a, 334b relative to one another when articulation sleeve 332 is rotated in a second direction. It is contemplated that the pitch of the threads between articulation sleeve 332 and articulation collars 334a, 334b may be selected as necessary to achieve the intended purpose of approximating or separating the collars 334a, 334b relative to one another.

Articulation assembly 330 further includes an articulation disk 336 rotatably disposed in housing 302 and keyed or otherwise secured to articulation sleeve 332. In this manner, as articulation disk 336 is rotated, concomitant rotation is transmitted to articulation sleeve 332 and to distal and proximal articulation collars 334a, 334b. Articulation disk 336 is keyed or otherwise connected to an articulation knob 338 rotatably supported in housing 302 and accessible through windows 304a, 306a of upper and lower housing halves 304, 306. In operation, as articulation knob 338 is rotated, said rotation is transmitted to articulation disk 336.

Articulation assembly 330 further includes a pair of articulation cables 340, 342 extending through and secured to end effector 200 and handle assembly 300. A first articulation cable 340 includes a first end secured to proximal articulation collar 334b and a second end extending through distal articulation collar 334a, through a respective slot in articulation disk 336, through respective lumen 212e1 of links 212, and secured to distal-most link 212 or stem 212f of neck portion 210 (see FIG. 18). A second articulation cable 342 includes a first end secured to distal articulation collar 334a and a second end extending through a respective slot in articulation disk 336, through respective lumen 212e2 of links 212, and secured to distal-most link 212 or stem 212f of neck portion 210 (see FIG. 18).

In operation, as will be described in greater detail below, as articulation knob 338 is rotated, rotation is transmitted to articulation disk 336 and on to articulation sleeve 332. As articulation sleeve 332 is rotated, distal and proximal articulation collars 334a, 334b are approximated and/or separated relative to one another, and thus cause retraction of either first or second articulation cable 340, 342, depending on the direction of rotation of articulation knob 338.

Articulation assembly 330 further includes a biasing member 346 supported on intermediate portion 236c of center drive rod assembly 236.

As seen in FIGS. 1-3 and 7-14, handle assembly 300 further includes a needle loading/retaining assembly 350 supported thereon. Needle loading/retaining assembly 350 includes a lever 352 pivotably supported in housing 302 and having a pair of arms 354a, 354b extending therefrom. Needle loading/retaining assembly 350 further includes a first blade control rod 356a and a second blade control rod 356b. Each blade control rod 356a, 356b includes a proximal end connected to lever 352 at opposed sides of a pivot axis. In this manner, as lever 352 is actuated or pivoted in a first direction, first blade control rod 356a is moved in a first direction and second blade control rod 356b is moved in a second direction, opposite to the first direction, and vice-versa. A distal end of each blade control rod 356a, 356b is connected to a respective inner drive assembly 242 and outer drive assembly 244, in particular, to respective inner barrel 242a and outer barrel 244a of drive assembly 240.

Figure 12:
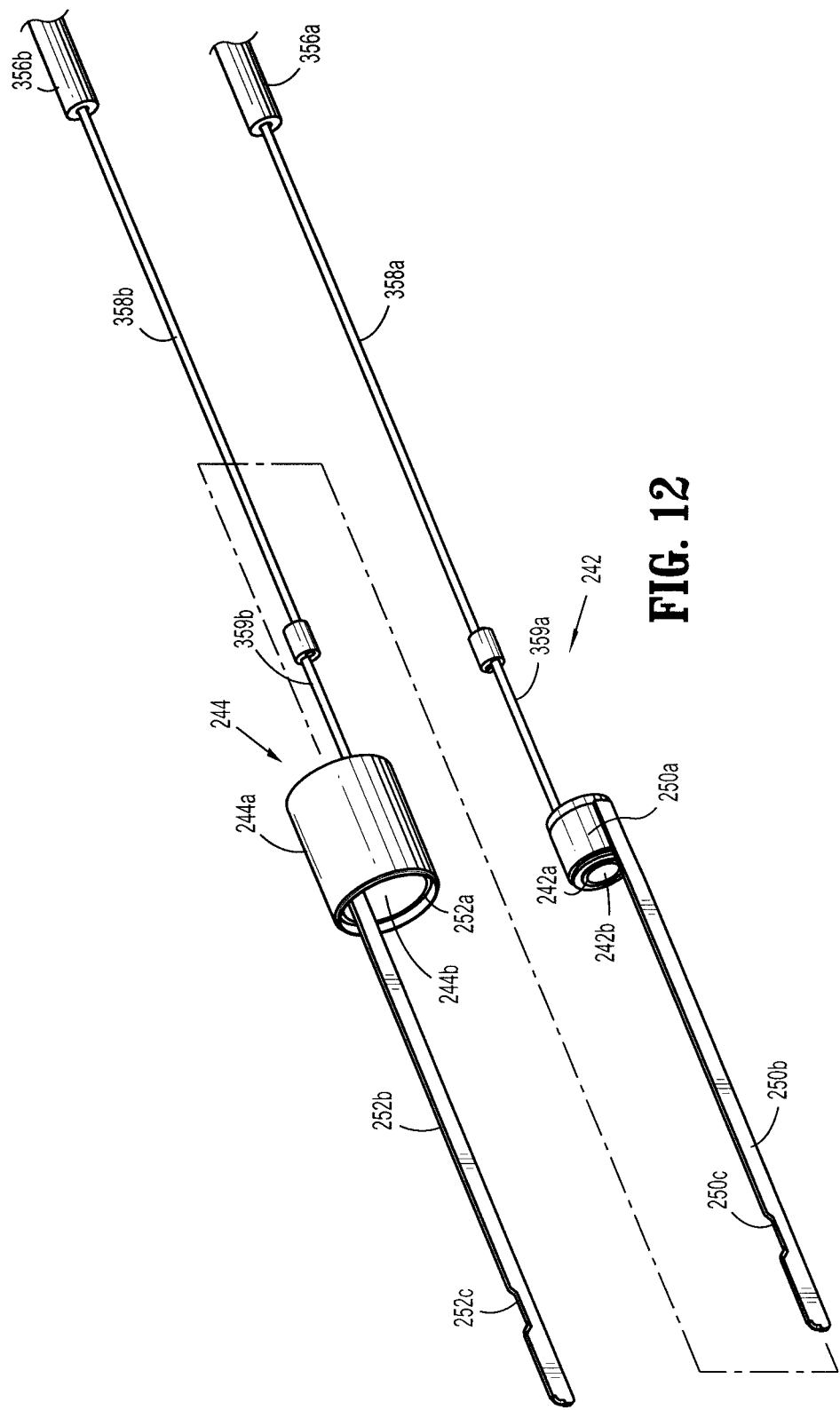
FIG. 12 is a perspective view, with parts separated, of a needle retention assembly of the flexible stitching device.
Figure 15:
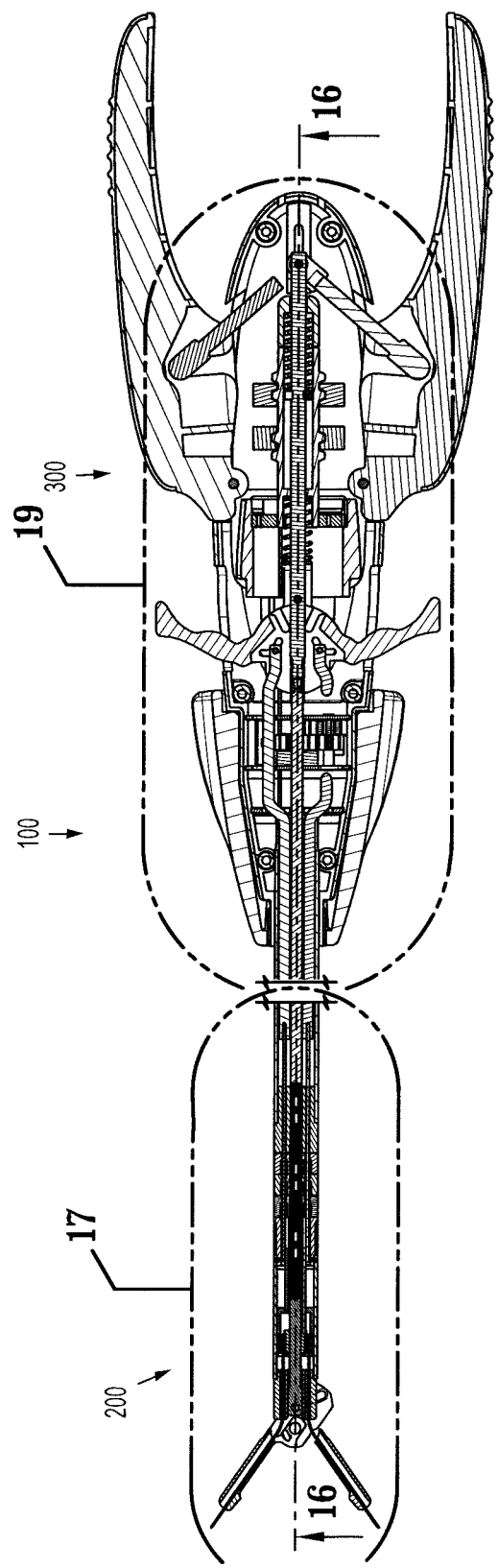
FIG. 15 is a longitudinal, cross-sectional view of the flexible stitching device of the present disclosure, as taken through 15-15 of FIG. 3.

As seen in FIGS. 12-14, needle loading/retaining assembly 350 further includes resilient bendable rods 358a, 358b interconnecting the distal end of each blade control rod 356a, 356b to respective inner barrel 242a and outer barrel 244a of drive assembly 240. As seen in FIGS. 13 and 14, a rod 359a, 359b may interconnect respective distal ends of blade control rods 356a, 356b and inner and outer barrels 242a, 244a.

Figure 20:
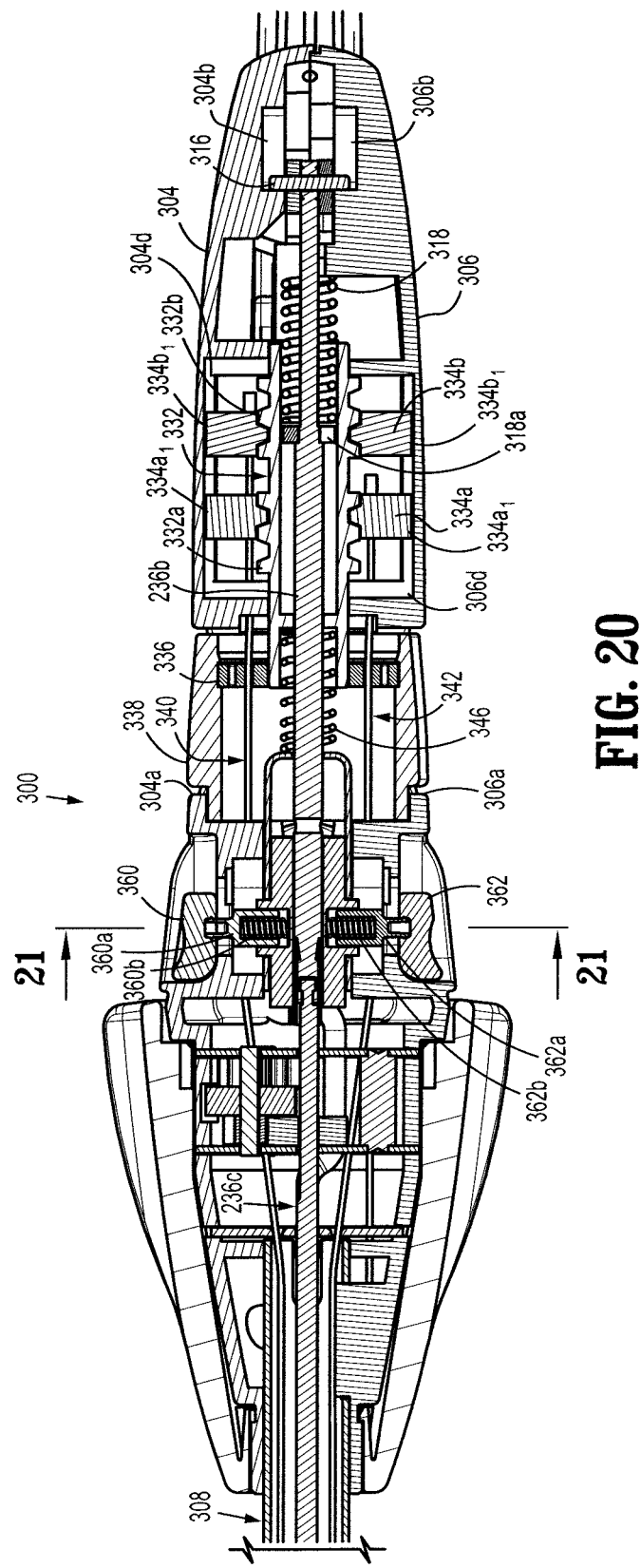
FIG. 20 is an enlarged view of the indicated area of detail of FIG. 16.
Figure 21:
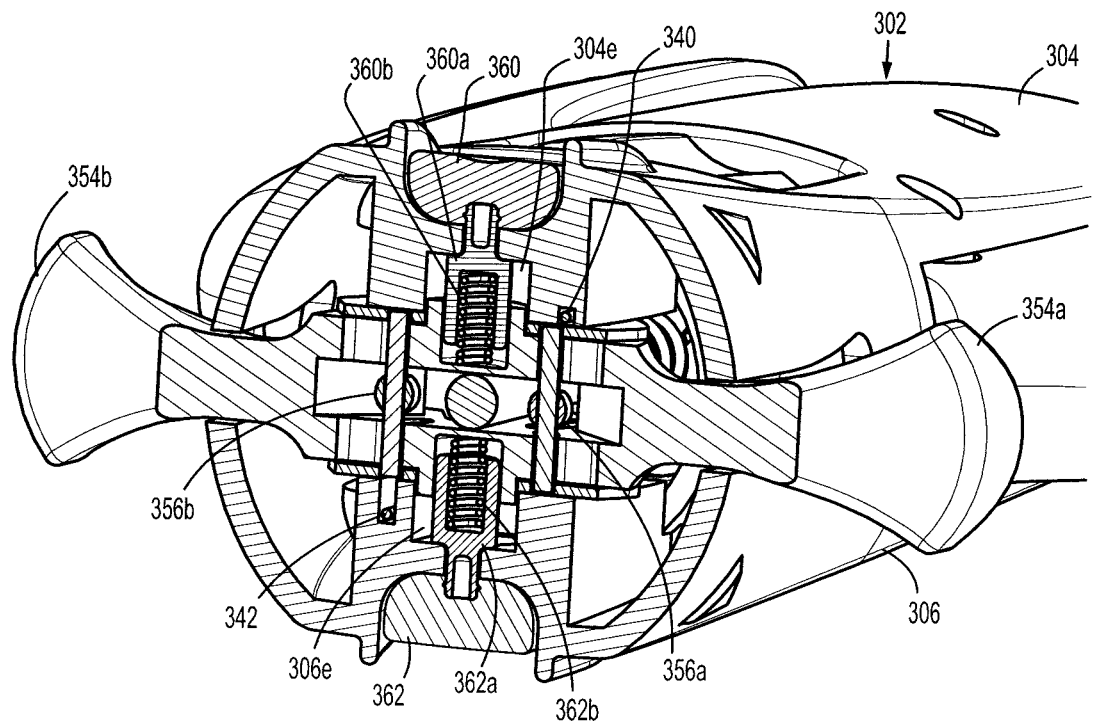
FIG. 21 is a cross-sectional view of the handle assembly, as taken through 21-21 of FIG. 20.
Figure 22:
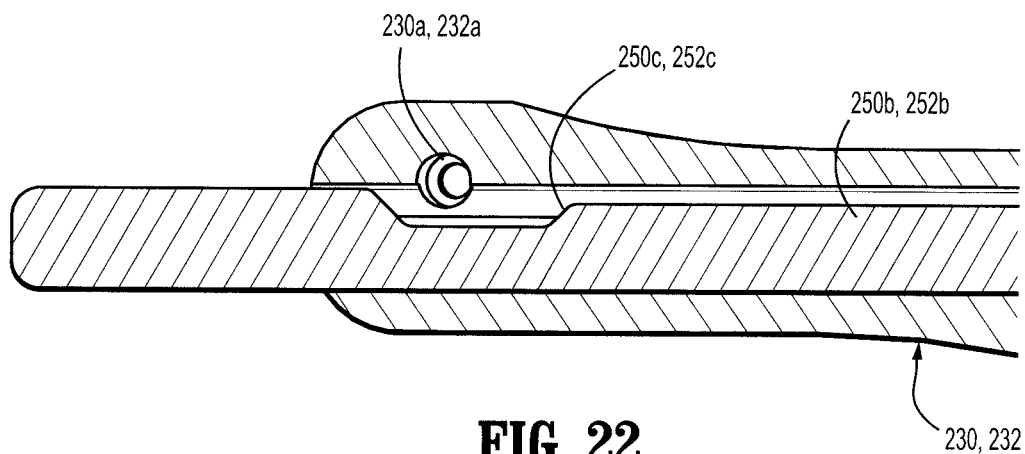
FIG. 22 is a cross-sectional view of a jaw of the end effector assembly, as taken through 22-22 of FIG. 17.

As seen in FIGS. 9, 10, 20-22 and 26-30, needle loading/retaining assembly 350 further includes a pair of needle loading/unloading buttons 360, 362 supported on housing 302. Needle loading/unloading buttons 360, 362 are slidable between a distal-most position and a proximal-most position. When needle loading/unloading buttons 360, 362 are in the distal-most position, blades 250b, 252b are in a distal-most position such that a respective notch 250c, 252c formed therein, as seen in FIG. 22, is aligned with or in registration with respective needle receiving openings 230a, 232a of respective jaws 230, 232. With blades 250b, 252b in a distal-most position, needle 104 of suture needle assembly 102 may be placed into a selected needle receiving opening 230a, 232a of a selected jaw 230, 232. When needle loading/unloading buttons 360, 362 are in the proximal-most position blades 250b, 252b are in a proximal-most position such that the respective notch 250c, 252c formed therein is out of aligned with or registration with respective needle receiving openings 230a, 232a of respective jaws 230, 232. With blades 250b, 252b in the proximal-most position, needle 104 of suture needle assembly 102, placed into the selected needle receiving opening 230a, 232a of a selected jaw 230, 232, is held in place due to the blade 250b, 252b engaging a groove 104a of needle 104.

As seen in FIGS. 9, 20 and 21, each button 360, 362 is supported on a respective biased stem 360a, 362a by a respective biasing member 360b, 362b. As seen in FIGS. 21 and 27-30, stems 360a, 360b are slidably disposed within respective slots 304e, 306e of upper and lower housing halves 304, 306. Each slot 304e, 306e includes an enlarged proximal end 304f, 306f configured to receive a portion of a respective stem 360a, 362a therein as buttons 360, 362 are moved to a proximal position. In order to move buttons 360, 362 in a distal direction, once stems 360a, 362a have seated in enlarged proximal ends 304f, 306f of slots 304e, 306e of upper and lower housing halves 304, 306, the user must depress buttons 360, 362 to move stems 360a, 362a out of enlarged proximal ends 304f, 306f of slots 304e, 306e and thus allow for buttons 360, 362 to move distally.

Figure 27:
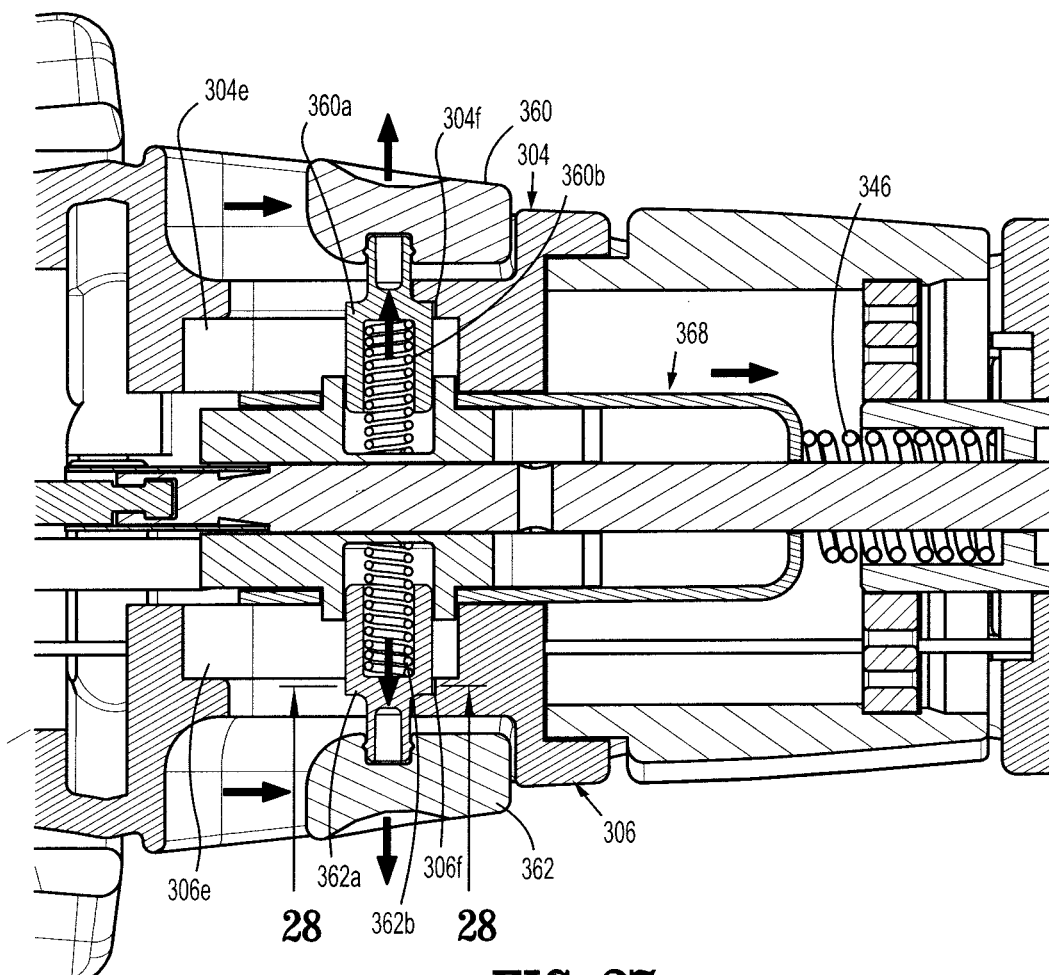
FIG. 27 is a cross-sectional view illustrating the movement of the needle load assembly during the initial actuation of the handle assembly.
Figure 28:
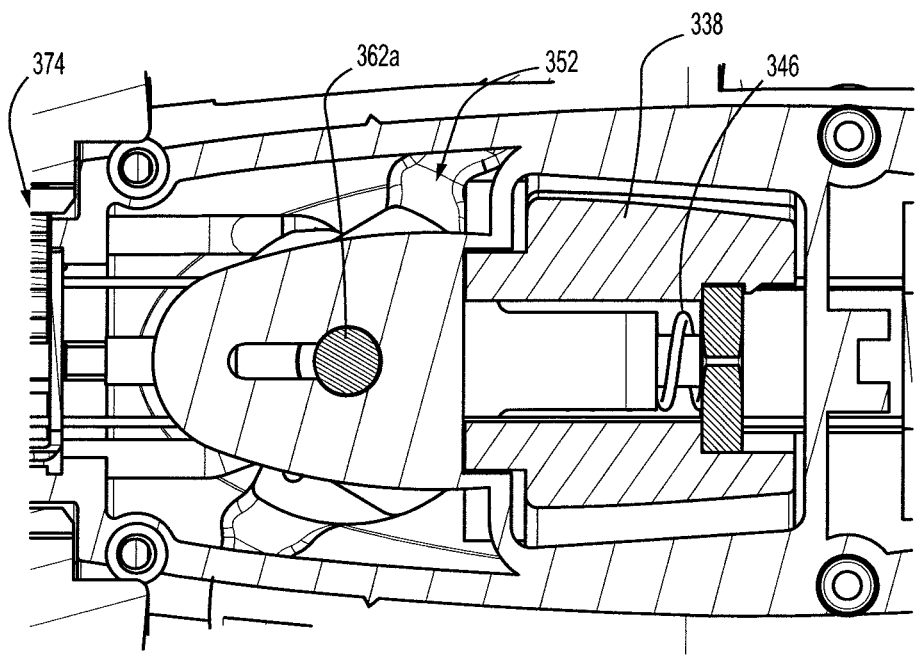
FIG. 28 is a cross-sectional view of the needle load assembly of FIG. 27 as taken through 28-28 of FIG. 27.
Figure 29:
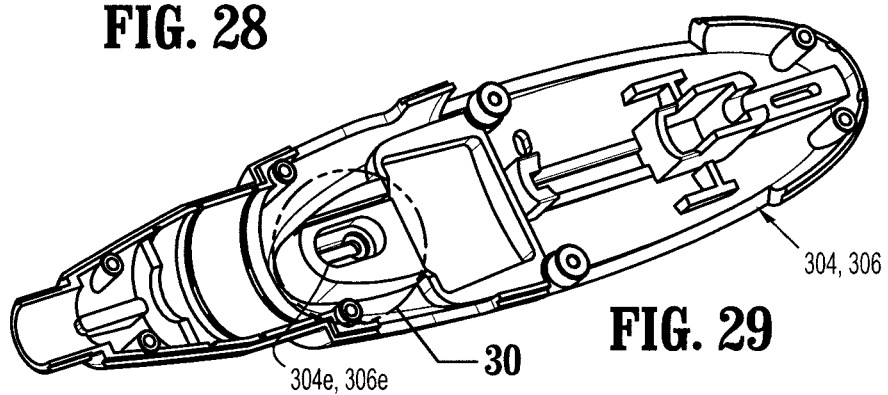
FIG. 29 is a perspective view of a housing half-section of the flexible stitching device.
Figure 30:
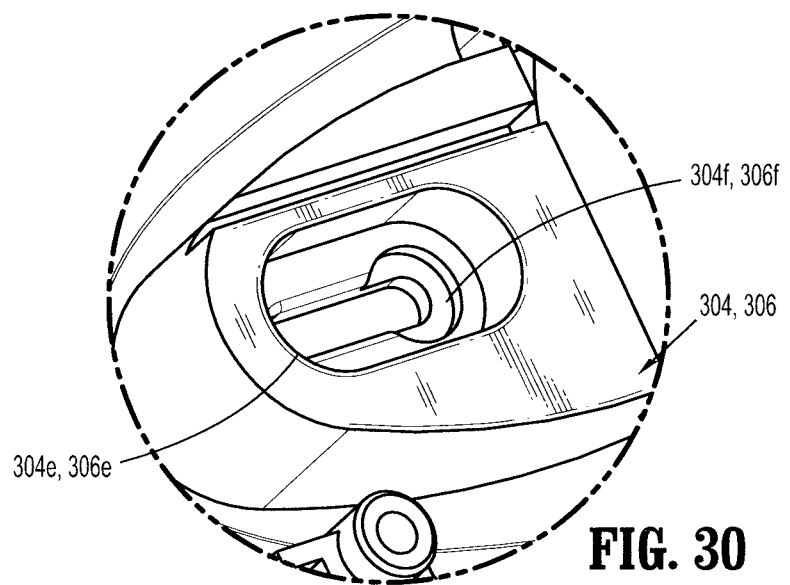
FIG. 30 is an enlarged view of the indicated area of detail of FIG. 29.

As seen in FIGS. 9, 10, 20 and 27, needle loading/retaining assembly 350 is supported on a frame or bracket 368. Bracket 368 is movable distally and proximally with lever 352 and is configured to permit passage of center drive rod assembly 236 therethrough. As seen in FIG. 27, biasing member 346 is interposed between bracket 368 and articulation sleeve 332. In use, as buttons 360, 362 are moved in a proximal direction, bracket 368 is moved in a proximal direction to compress biasing member 346. In this manner, when buttons 360, 362 are depressed to disengage stems 360a, 362a from enlarged proximal ends 304f, 306f of slots 304e, 306e, biasing member 346 is permitted to expand the thus return buttons 360, 362 to a distal position.

As seen in FIGS. 1-3, 7-10, 45 and 46, handle assembly 300 further includes a tip rotation assembly 370 supported on housing 302 for rotating end effector 200 about the longitudinal axis thereof. Tip rotation assembly 370 includes a rotation knob 372 supported on housing 302. Rotation knob 372 defines an annular array of internal gear teeth 372a. Tip rotation assembly 370 includes a gear system 374 supported on a frame 376 in housing 302. Gear system 374 includes at least a first gear 374a operatively engaged with gear teeth 372a of rotation knob 372, at least a second gear 374b keyed to or otherwise connected to intermediate portion 236c of center drive rod assembly 236, and at least a third gear 374c interconnecting the first gear 374a and the second gear 374b such that the direction of rotation of rotation knob 372 results in concomitant rotation of the intermediate portion 236c and the distal portion 236a of center drive rod assembly 236 and, in turn, end effector 200. As intermediate portion 236c and distal portion 236a of center drive rod assembly 236 is rotated, said rotation is transmitted to camming pin 238 of jaws 230, 232 and thus rotation is transmitted to end effector 200. Since blades 250b, 252b are rotatably supported on respective barrels 242a, 244a, blades 250b, 252b also rotate with end effector 200.

Figure 16:
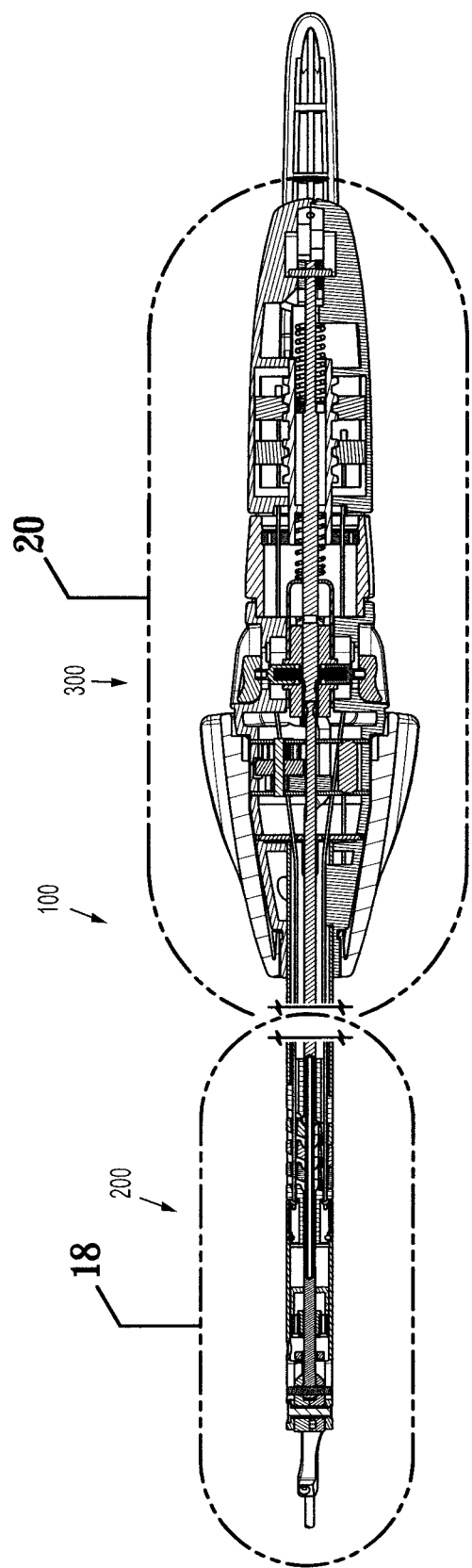
FIG. 16 is a longitudinal, cross-sectional view of the flexible stitching device of the present disclosure, as taken through 16-16 of FIG. 15.
Figure 19:
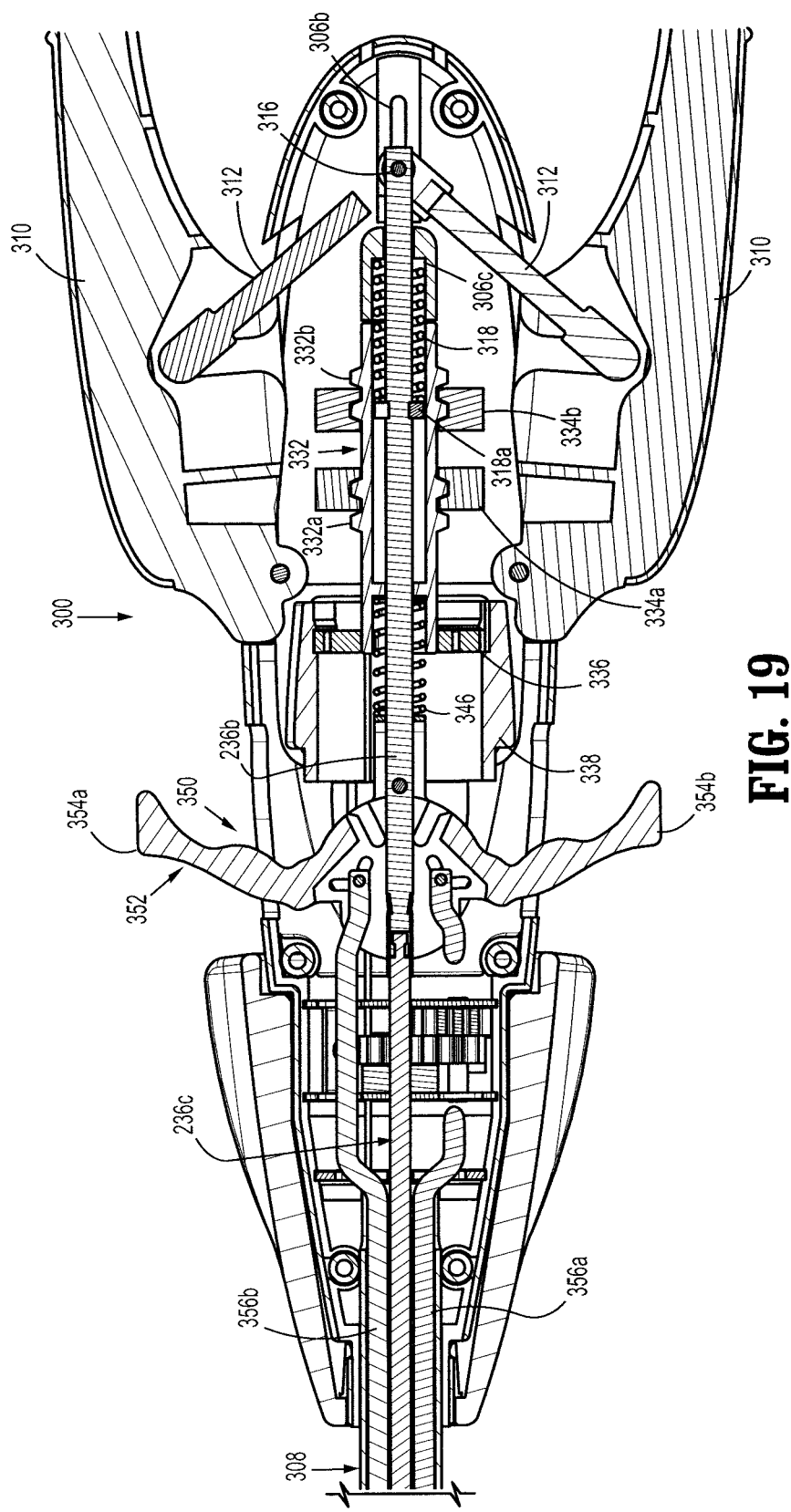
FIG. 19 is an enlarged view of the indicated area of detail of FIG. 15.
Figure 26:
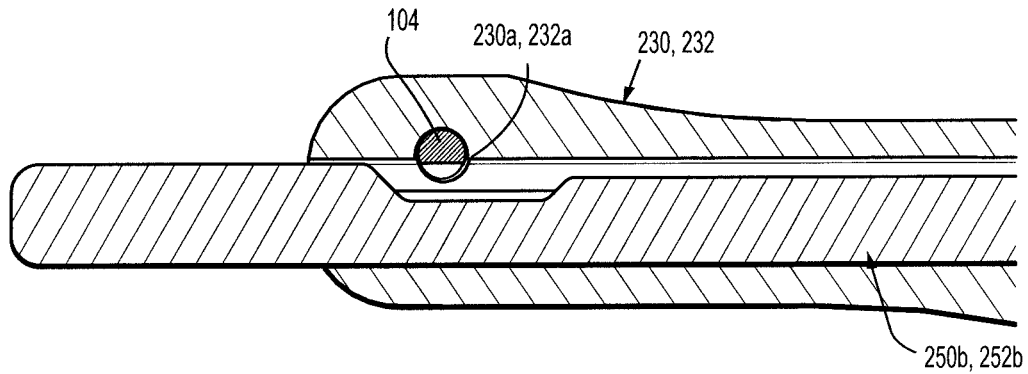
FIG. 26 is a cross-sectional view of the jaw of the end effector illustrating the needle of the suture needle assembly disposed therein.

Turning now to FIGS. 15-53, a detailed discussion of the operation of flexible endoscopic stitching device 100 is provided. As seen in FIGS. 15-22, stitching device 100 is shown in a needle load/unload configuration. When stitching device 100 is in the needle load/unload configuration, as seen in FIGS. 16 and 20, needle loading/retaining assembly 350 is in a distal position such that blades 250b, 252b are in a distal-most position and, as seen in FIG. 22, respective notches 250c, 252c formed therein, are aligned with or in registration with respective needle receiving openings 230a, 232a of respective jaws 230, 232. With notches 250c, 252c of blades 250b, 252b aligned with or in registration with respective needle receiving openings 230a, 232a of respective jaws 230, 232, as seen in FIGS. 24-26, needle 104 of suture needle assembly 102 may be positioned or loaded into a selected one needle receiving opening 230a, 232a of respective jaws 230, 232.

Figure 23:
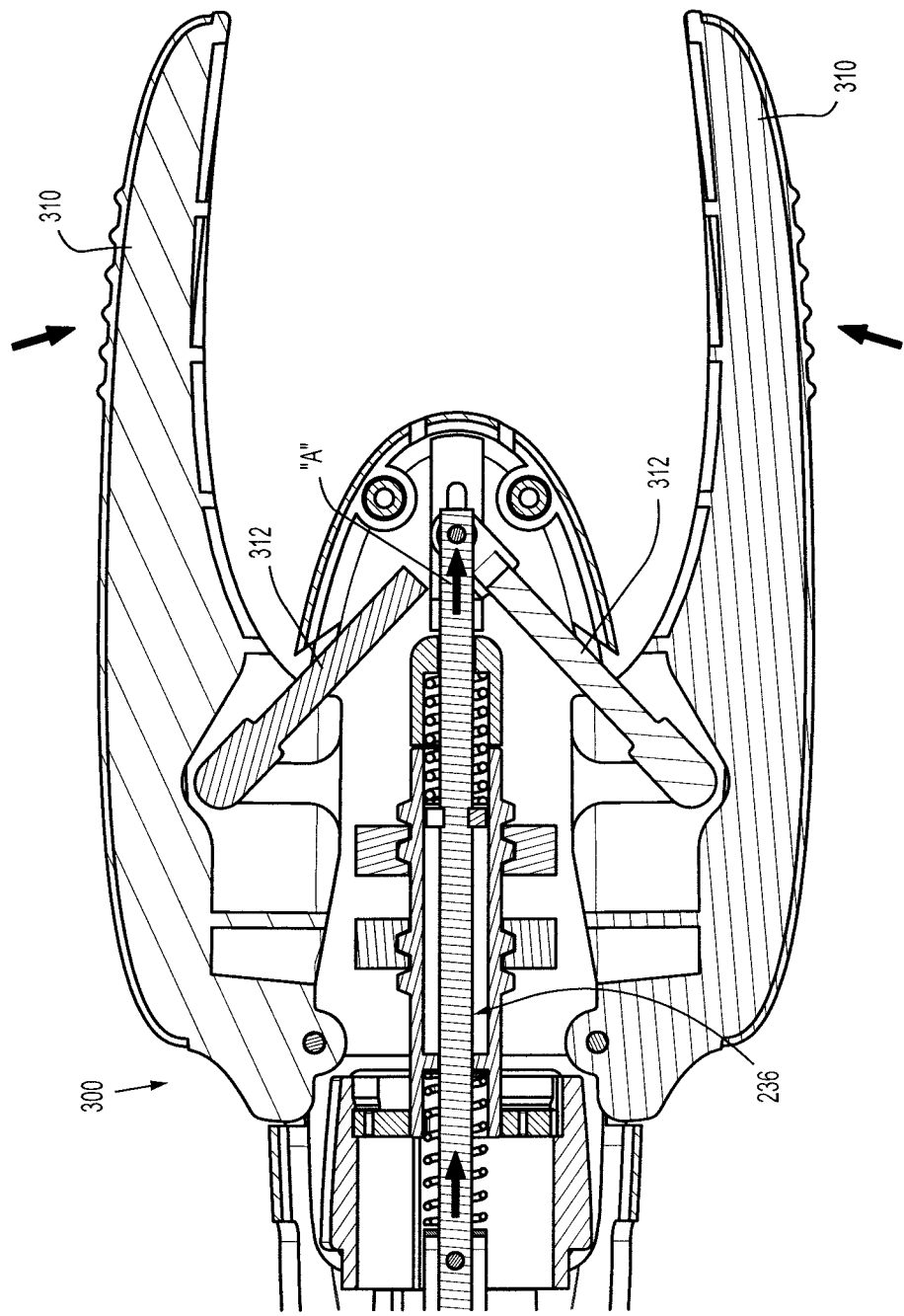
FIG. 23 is a cross-sectional view of the handle assembly, of the flexible stitching device, illustrating an initial actuation of the handles thereof.

As seen in FIGS. 23-26, once needle 104 is loaded into either needle receiving opening 230a, 232a of respective jaws 230, 232, handles 310 are actuated (e.g., squeezed) to move link members 312 and, in turn, axially displace center drive rod assembly 236 in a proximal direction (as indicated by arrow "A" of FIGS. 23 and 24). As seen in FIGS. 24 and 25, as center drive rod assembly 236 is moved in a proximal direction, camming pin 238 is moved in a proximal direction to approximate jaws 230, 232.

As seen in FIG. 27, once needle 104 is loaded into either needle receiving opening 230a, 232a of respective jaws 230, 232, needle loading/retaining assembly 350 is moved in a proximal direction to thereby retract blades 250b, 252b and cause each blade 250b, 252b to engage a respective groove 104a of needle 104.

Figure 31:
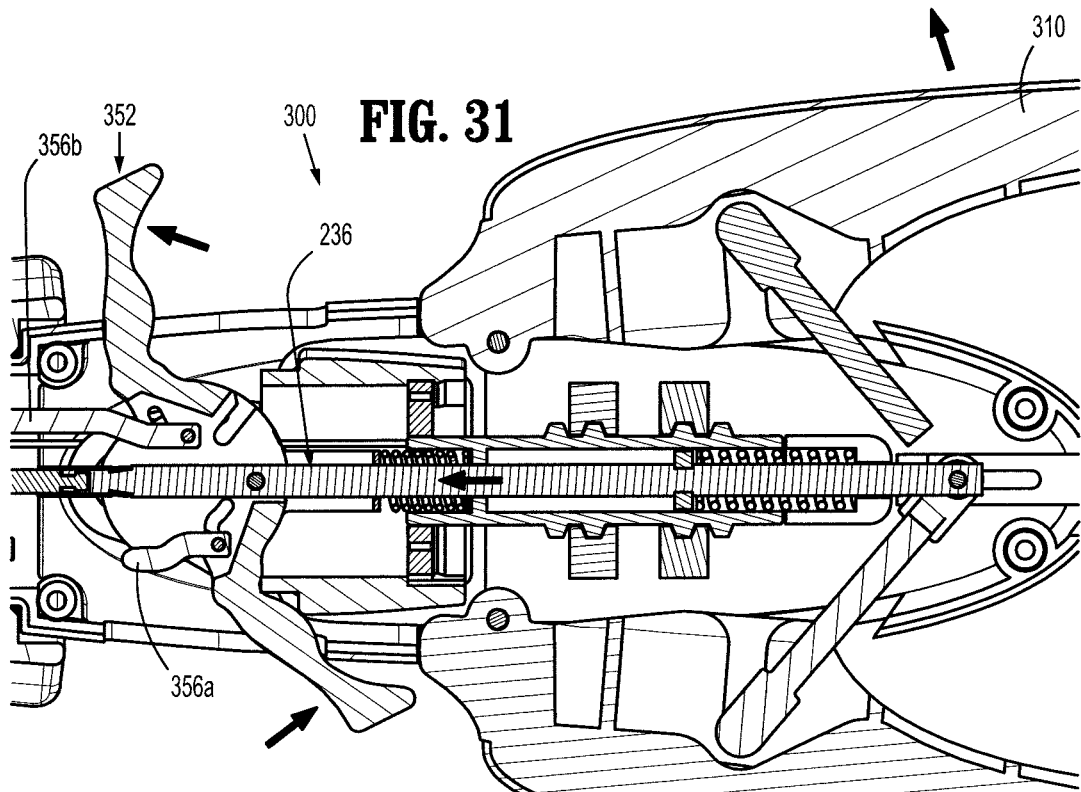
FIG. 31 is a cross-sectional view of the handle assembly, of the flexible stitching device, illustrating a release of handles thereof and an actuation of a needle retention assembly.
Figure 32:
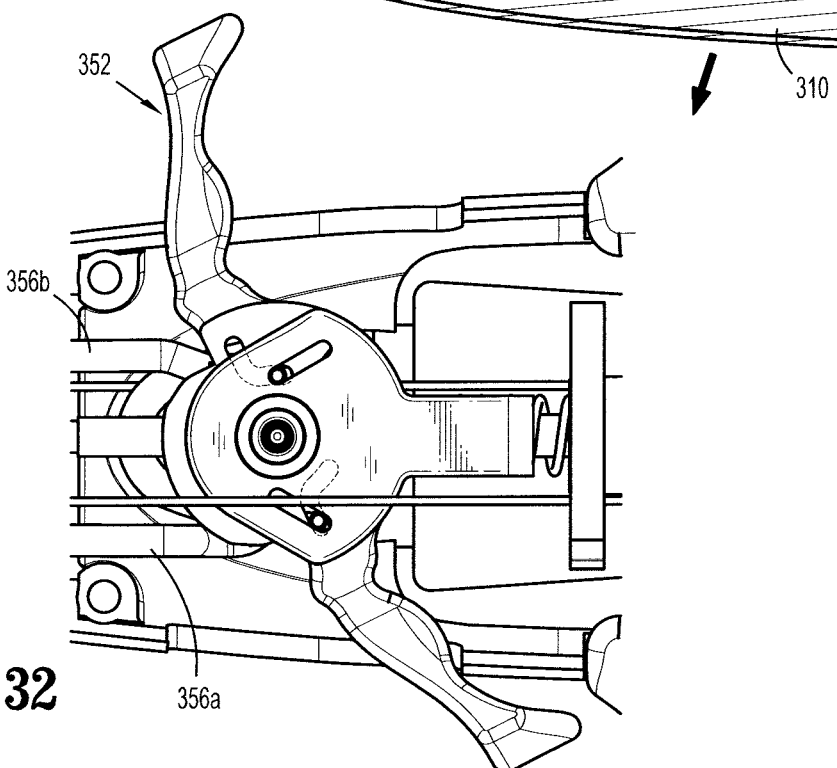
FIG. 32 is a plan view further illustrating the actuation of the needle retention assembly.
Figure 33:
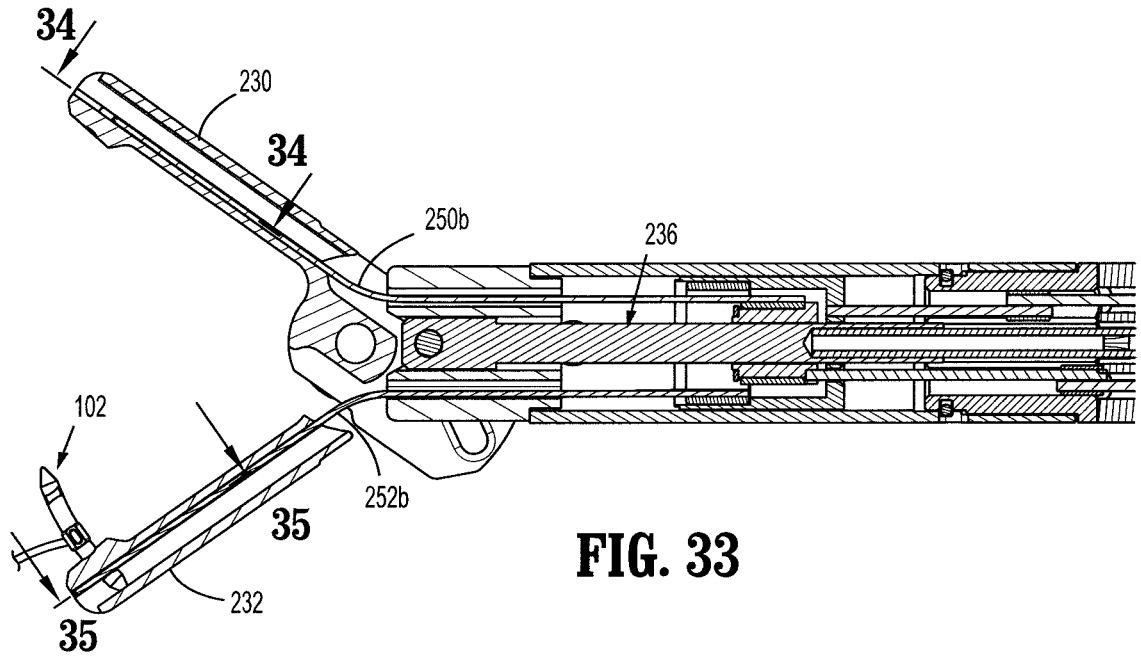
FIG. 33 is a longitudinal, cross-sectional view of the end effector assembly, illustrating the loading of a suture needle assembly therein.
Figure 34:
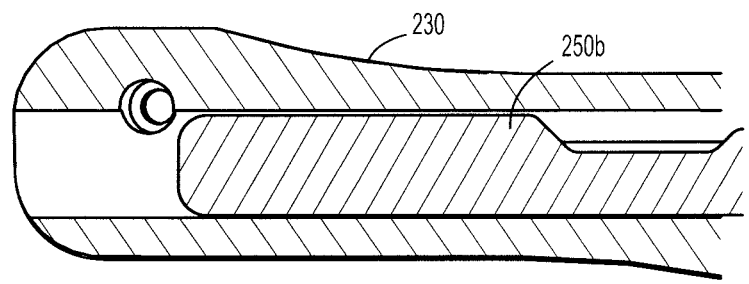
FIG. 34 is a cross-sectional view of the end effector assembly as taken through 34-34 of FIG. 33.
Figure 35:
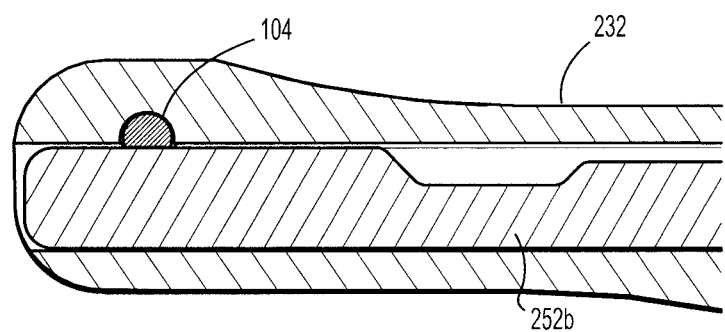
FIG. 35 is a cross-sectional view of the end effector assembly as taken through 35-35 of FIG. 33.
Figure 36:
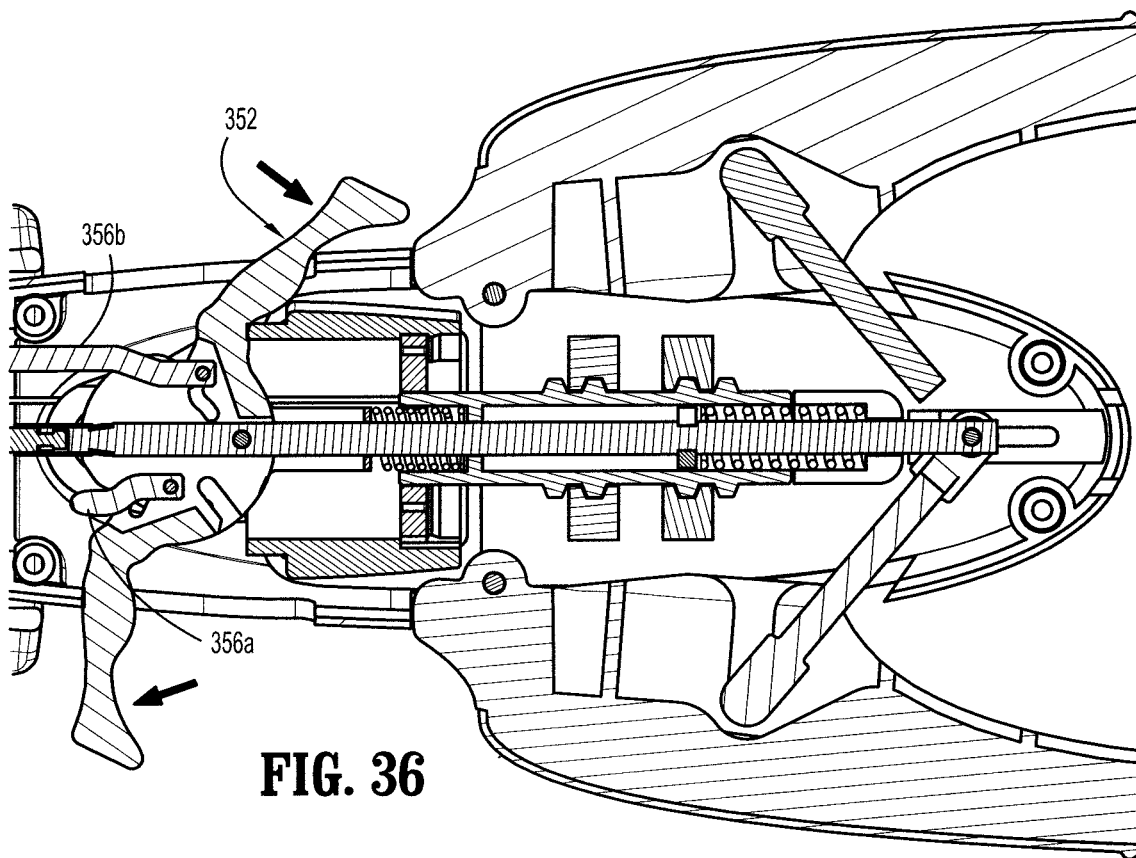
FIG. 36 is a cross-sectional view of the handle assembly, of the flexible stitching device, illustrating a further actuation of the needle retention assembly.

As seen in FIGS. 31-35, with needle 104 engaged by both blades 250b, 252b, as seen in FIGS. 31 and 32, lever 352 is actuated or rotated so that only one blade 250b, 252b, e.g., blade 252b, is maintained in engagement with needle 104, as seen in FIG. 35, and the other blade 250b is disengaged from needle 104, as seen in FIG. 34. With only one blade, e.g., blade 252b, engaged with needle 104, as seen in FIGS. 33-35, handles 310 may be released, as seen in FIG. 31, thereby moving center drive rod assembly 236 and camming pin 238 in a distal direction to open jaws 230, 232.

With jaws 230, 232 open, end effector 200 may be positioned at the surgical site as needed, and handles 310 reactuated to approximate jaws 230, 232. For example, with jaws 230, 232 in an open position and needle 104 loaded therein, jaws 230, 232 may be positioned about or over a target tissue and handles 310 actuated to approximate jaws 230, 232. As jaws 230, 232 are approximated, the exposed end of needle 104 is penetrated through the target tissue and enters into the opposed jaw 230, 232. With needle 104 in the opposed jaw 230, 232, as seen in FIG. 36, lever 352 is once again actuated or rotated so that blades 250b, 252b are reversed. In so doing, blade 252b is disengaged from needle 104 and blade 250b is engaged with needle 104.

Figure 37:
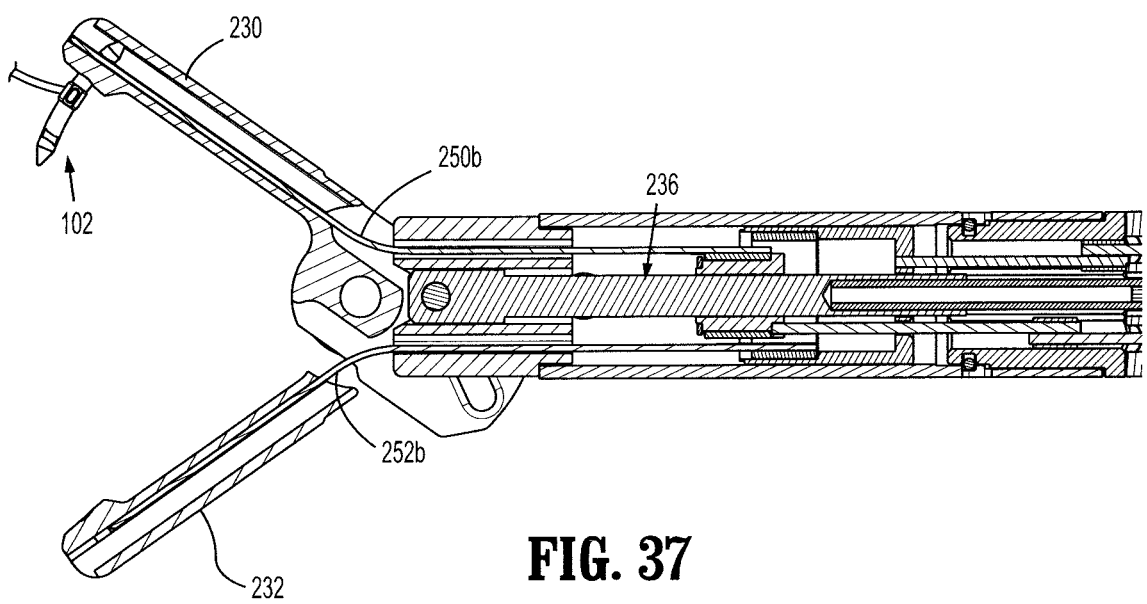
FIG. 37 is a longitudinal, cross-sectional view of the end effector assembly, illustrating the positioning of the needle of the suture needle assembly in an opposite jaw thereof.
Figure 38:
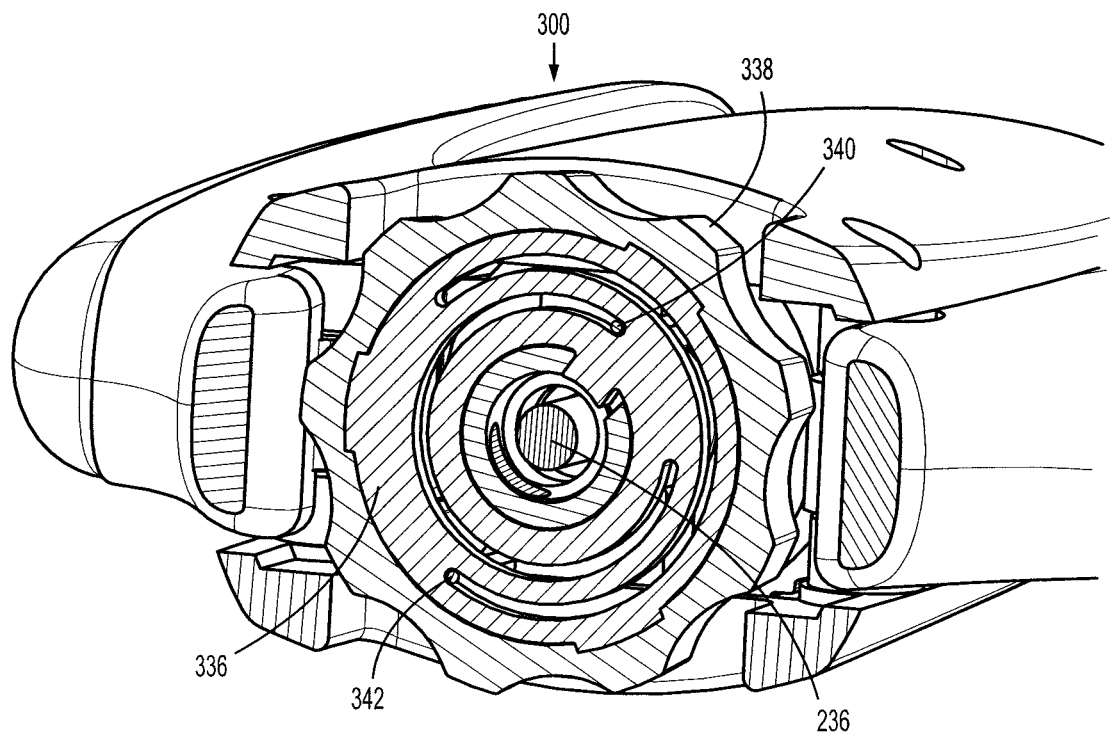
FIG. 38 is a cross-sectional view of the handle assembly as taken through 38-38 of FIG. 8.
Figure 39:
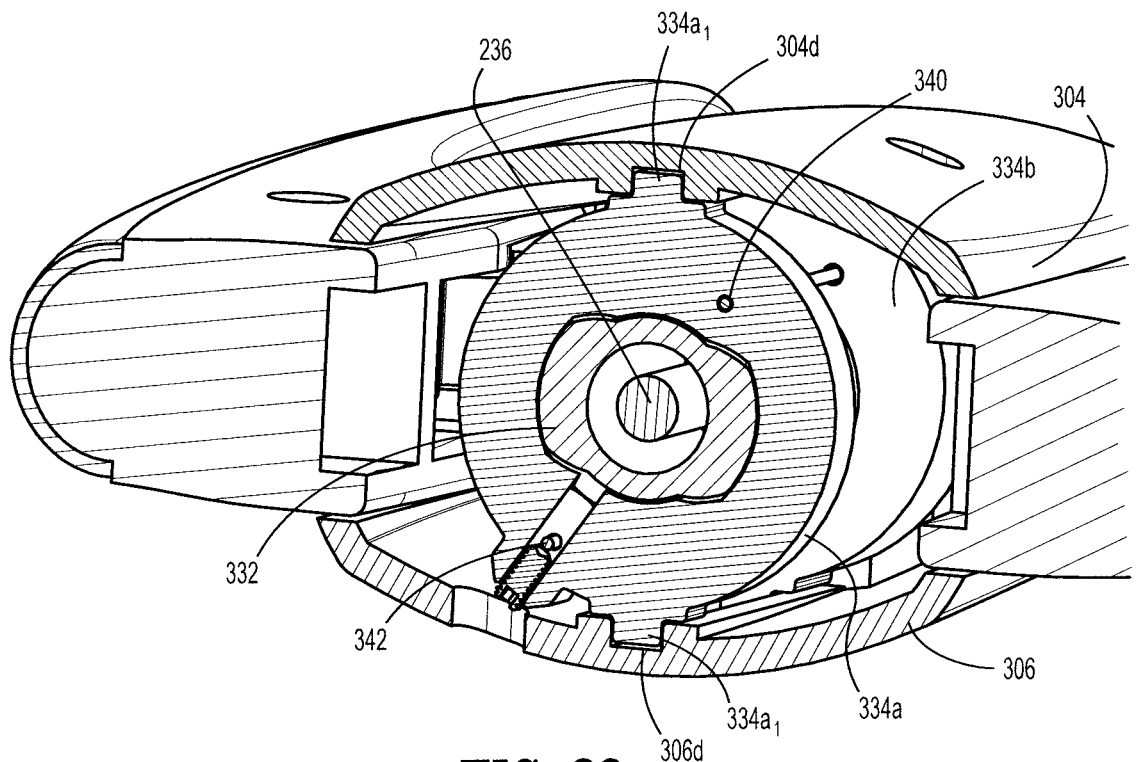
FIG. 39 is a cross-sectional view of the handle assembly as taken through 39-39 of FIG. 8.
Figure 40:
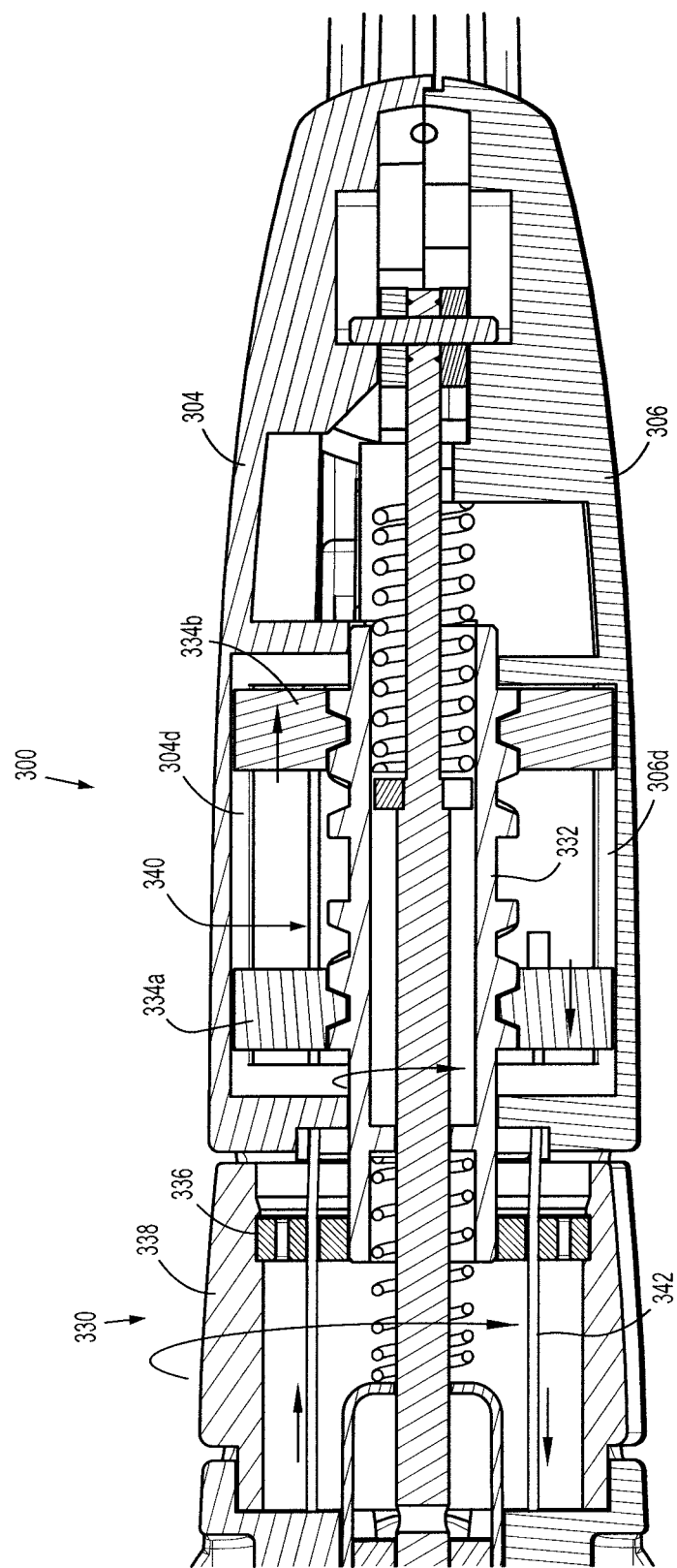
FIG. 40 is a longitudinal cross-sectional view of the handle assembly, illustrating an actuation of the articulation assembly.

As seen in FIG. 37, with needle 104 engaged by blade 250b, handles 310 may be released to thereby open jaws 230, 232 and draw needle 104 through the target tissue. In so doing, suture 106 is also drawn through the tissue. The process is repeated numerous times passing the needle 104 between jaws 230, 232 and drawing suture through the target tissue thereby suturing the target tissue as needed and or desired.

During a surgical procedure, if desired or necessary, as seen in FIGS. 38-44, a user may actuate articulation knob 338 of articulation assembly 330 to effectuate articulation or off-axis movement of end effector 200. In particular, as articulation knob 338 is rotated, rotation is transmitted to articulation disk 336 and on to articulation sleeve 332. As articulation sleeve 332 is rotated, distal and proximal articulation collars 334a, 334b are moved from an approximated condition to a more separated condition relative to one another, thus causing retraction of first articulation cable 340 and extension of second articulation cable 342.

Figure 43:
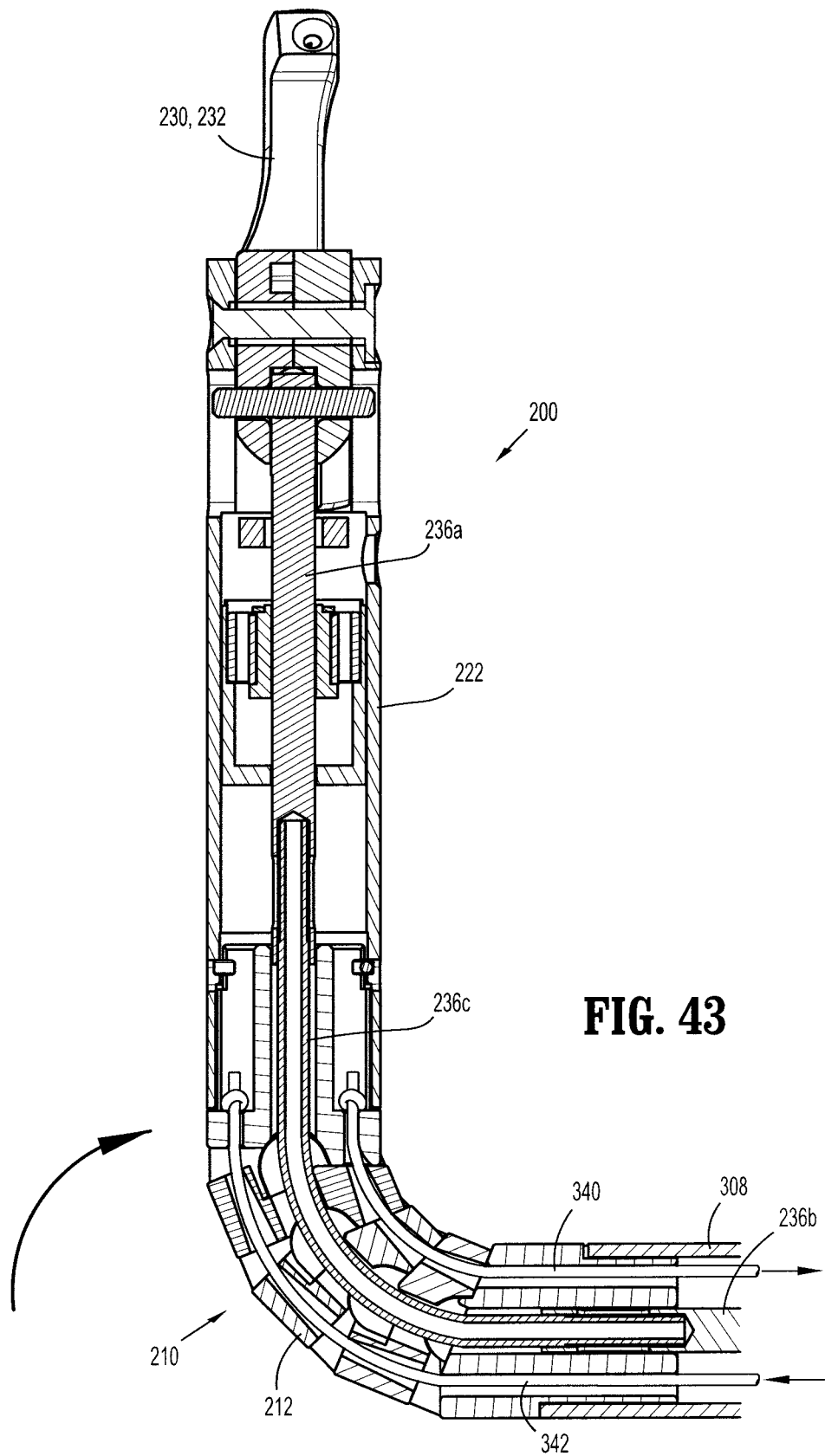
FIG. 43 is a cross-sectional view of the end effector, illustrating an articulation thereof.
Figure 44:
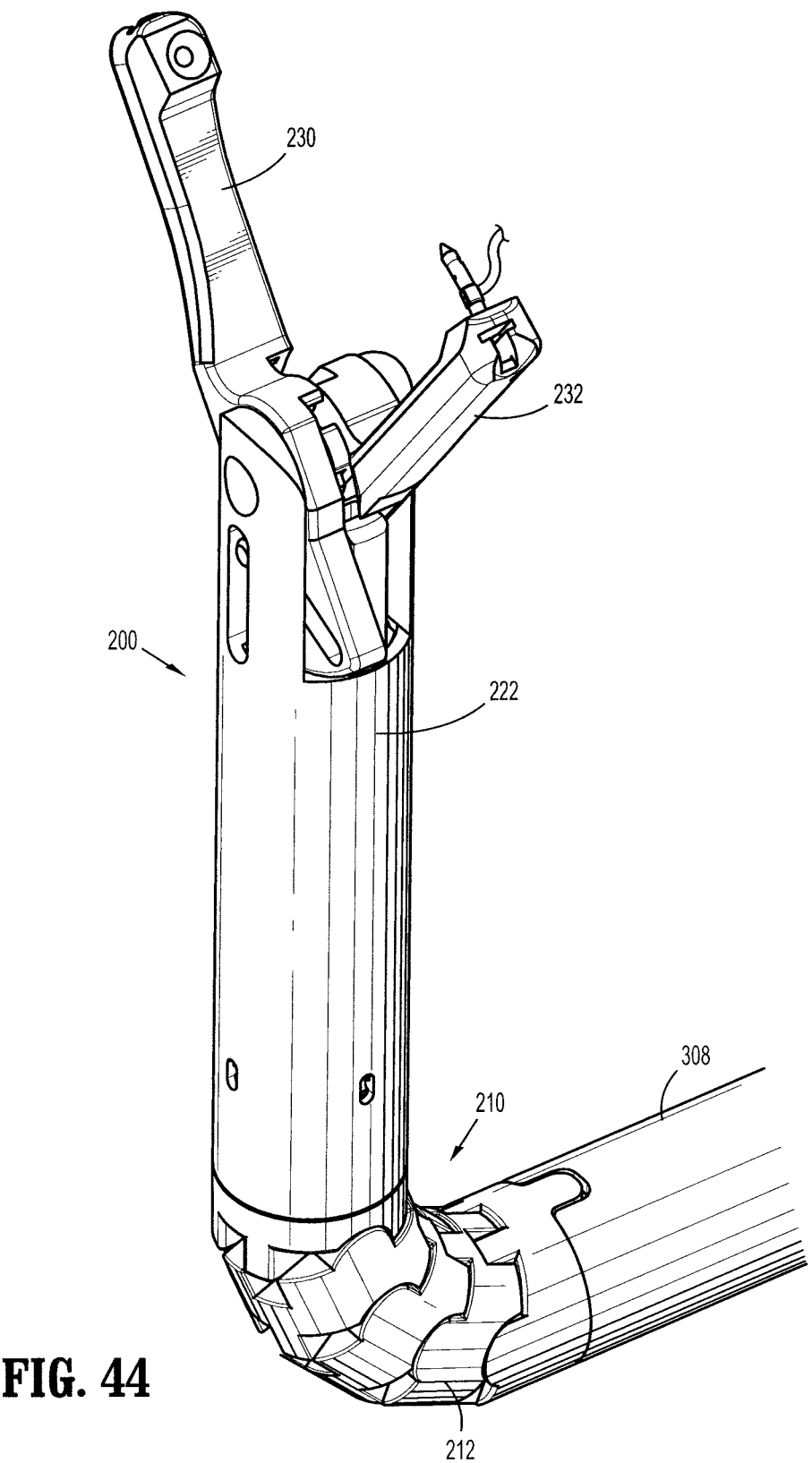
FIG. 44 is a perspective view of the end effector of FIG. 43.
Figure 45:
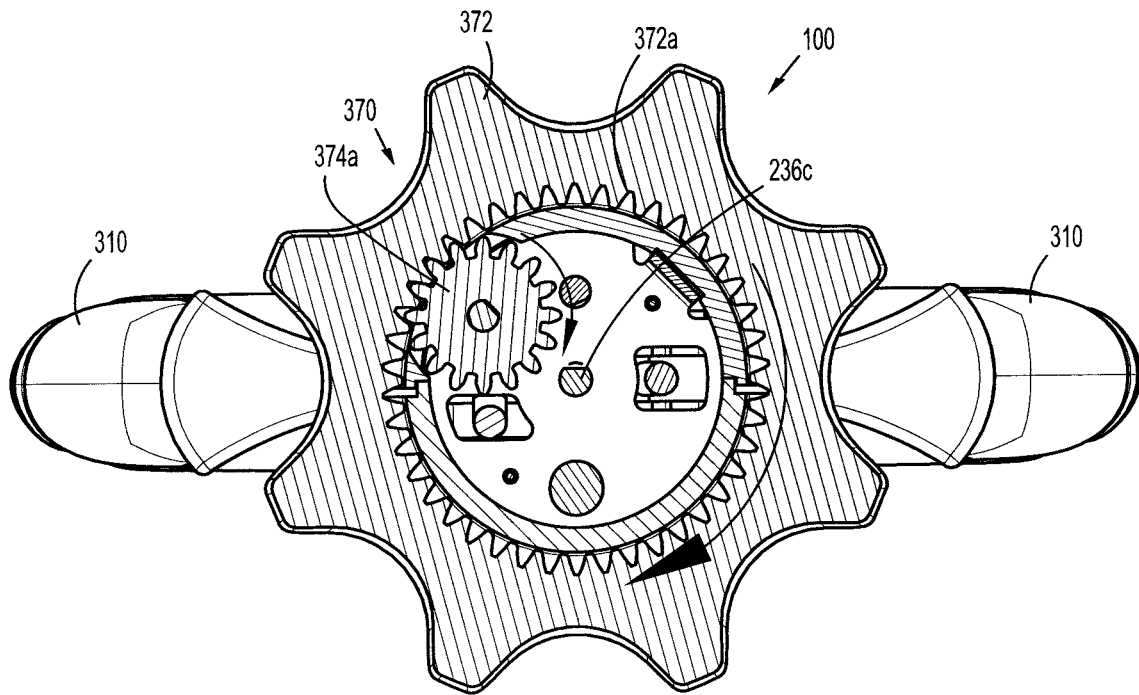
FIG. 45 is a cross-sectional view of the handle assembly as taken through 45-45 of FIG. 7, illustrating an operation of a rotation assembly of the flexible stitching device.
Figure 46:
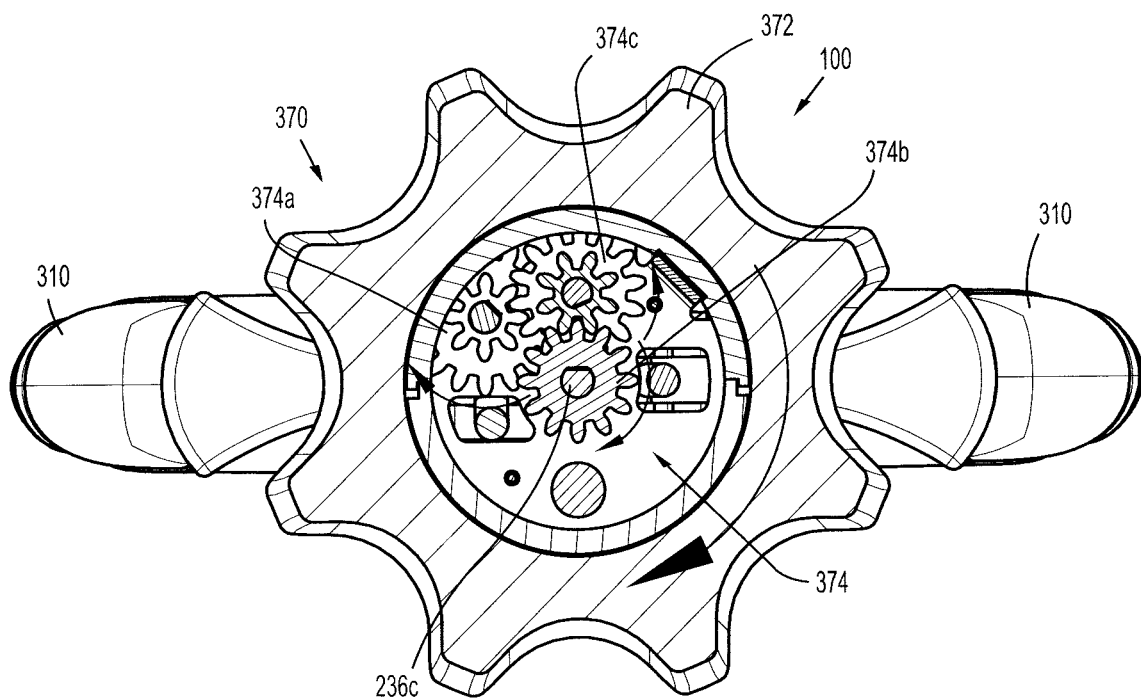
FIG. 46 is a cross-sectional view of the handle assembly as taken through 46-46 of FIG. 7, illustrating a further operation of a rotation assembly of the flexible stitching device.

As seen in FIGS. 43 and 44, as first articulation cable 340 is retracted and second articulation cable 342 is extended, end effector 200 is articulated at neck portion 210. As end effector 200 is articulated, intermediate portion 236c of center drive rod assembly 236 is flexed. In this manner, end effector 200 is still capable of rotation about its axis and jaws 230, 232 are still capable of opening and closing.

As seen in FIG. 44, while in an articulated condition, links 212 remain at least partially over-lapped in order to inhibit entry of tissue of the like therebetween. In this manner, when end effector 200 is returned to un-articulated or linear condition, tissue will not be caught or pinched between links 212 of neck portion 210.

During a surgical procedure, if desired or necessary, as seen in FIGS. 45-53, a user may actuate rotation knob 372 of tip rotation assembly 370 to effectuate rotation of end effector 200 along a longitudinal axis thereof. In particular, as rotation knob 372 is rotated intermediate portion 236c and distal portion 236a of center drive rod assembly 236 is rotated. As intermediate portion 236c and distal portion 236a of center drive rod assembly 236 is rotated, said rotation is transmitted to camming pin 238 of jaws 230, 232 and thus rotation is transmitted to end effector 200.

Turning now to FIGS. 54-57, a tip rotation assembly according to another embodiment of the present disclosure, for use with stitching device 100, is generally designated as 470. Tip rotation assembly 470 includes a rotation knob 472 supported on housing 302. Knob 472 defines an arcuate slot 472a formed in a rear surface thereof and which arcuate slot 472a extends radially outward from a central rotational axis of knob 472 and extends approximately 180° about the central rotational axis. Tip rotation assembly 470 includes a collar 474 keyed to or otherwise secured to center drive rod assembly 236. Tip rotation assembly 470 further includes a wishbone link 476 having a first end 476a pivotally connected to collar 474 and a second end 476b pivotally supporting a piston 478. First end 476a of link 476 is curved about an axis transverse to a pivot axis thereof, so as to define a pocket 476c configured to selectively receive center drive rod assembly 236 therein. A pin 479 extends though piston 478 and connects piston 478 to arcuate slot 472a.

Rotation assembly 470 includes a home position in which pin 479 is located at a first end of arcuate slot 472a, where the arcuate slot 472a is furthest from the center drive rod assembly 236.

In operation, in order to rotate end effector 200 about the longitudinal axis thereof, rotation knob 472 is rotated from the home position. As rotation knob 472 is rotated, pin 479 slidably translates through arcuate slot 472a, approximating pin 479 toward center drive rod assembly 236. As pin 479 is approximated toward center drive rod assembly 236, wishbone link 476 is provided with sufficient clearance in order for wishbone link 476 to encircle center drive rod assembly 236. In this way, rotation of knob 472 results in a transmission of a rotational force to center drive rod assembly 236 via piston 478, wishbone link 476 and collar 474.

Turning now to FIGS. 58-62, a tip rotation assembly according to another embodiment of the present disclosure, for use with stitching device 100, is generally designated as 570. Tip rotation assembly 570 includes a rotation knob 572 supported on housing 502. Knob 572 defines an inner helical thread 572a formed in an inner surface thereof. Tip rotation assembly 570 includes a nut disposed within housing 502. Nut 574 includes a pair of opposed stems 574a extending radially therefrom and through respective longitudinally extending slots 502a formed in housing 502. Stems 574a of nut 574 are sufficiently long to engage helical thread 574a of rotation knob 574. Nut 574 defines an inner helical thread 574b.

Tip rotation assembly 570 further includes a lead screw 576 keyed to or otherwise connected to center drive rod assembly 236. Lead screw 576 includes an outer thread or the like 576a which is configured to operatively engage inner helical thread 574b of nut 574. Lead screw 576 is further axially fixed and rotatably supported in braces 502b formed in housing 502.

Figure 62:
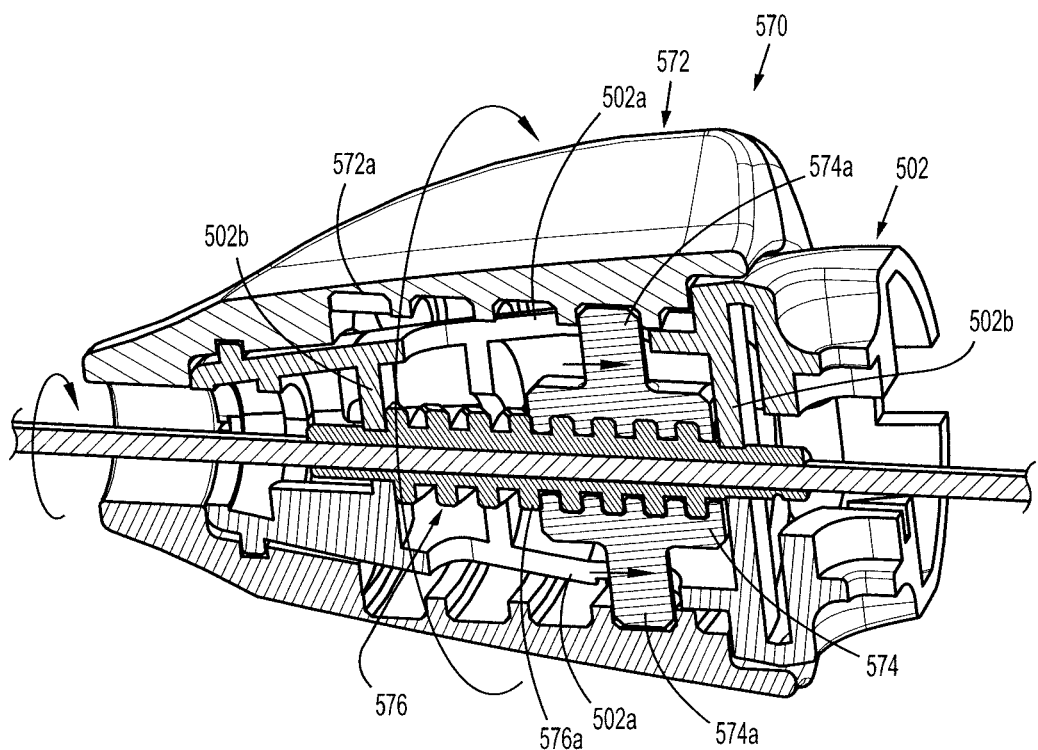
FIG. 62 is the cross-sectional view of FIG. 59, illustrating an operation of the end effector rotation assembly of FIGS. 58-61.
Figure 63:
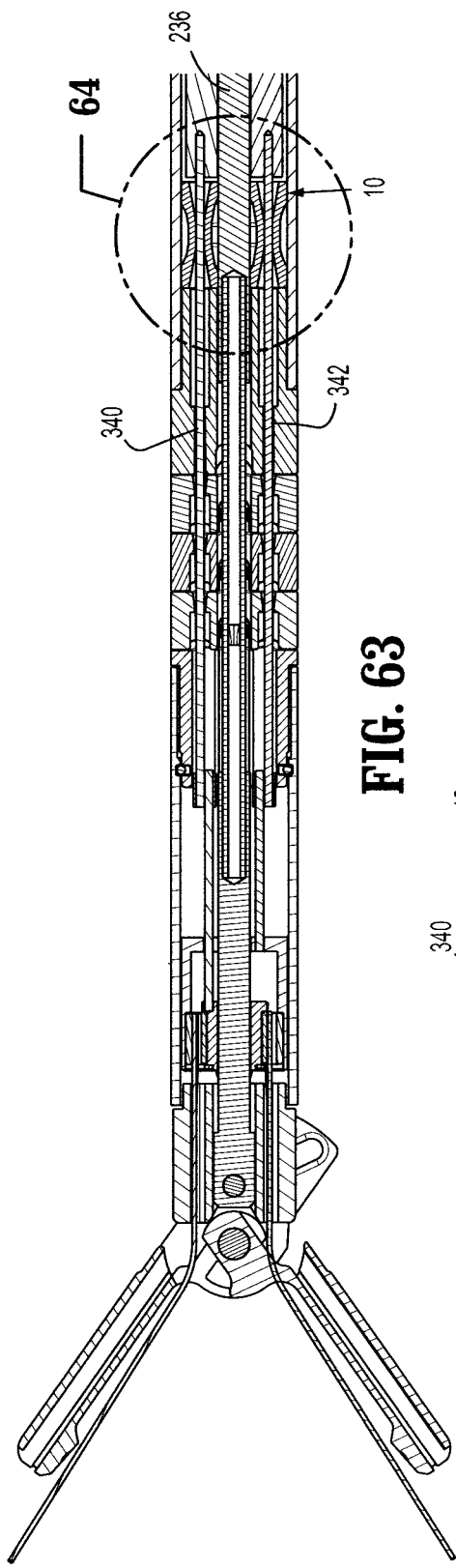
FIG. 63 is a longitudinal, cross-sectional view of another embodiment of the distal end of a flexible stitching device of the present disclosure, including an arched seal therein.
Figure 64:
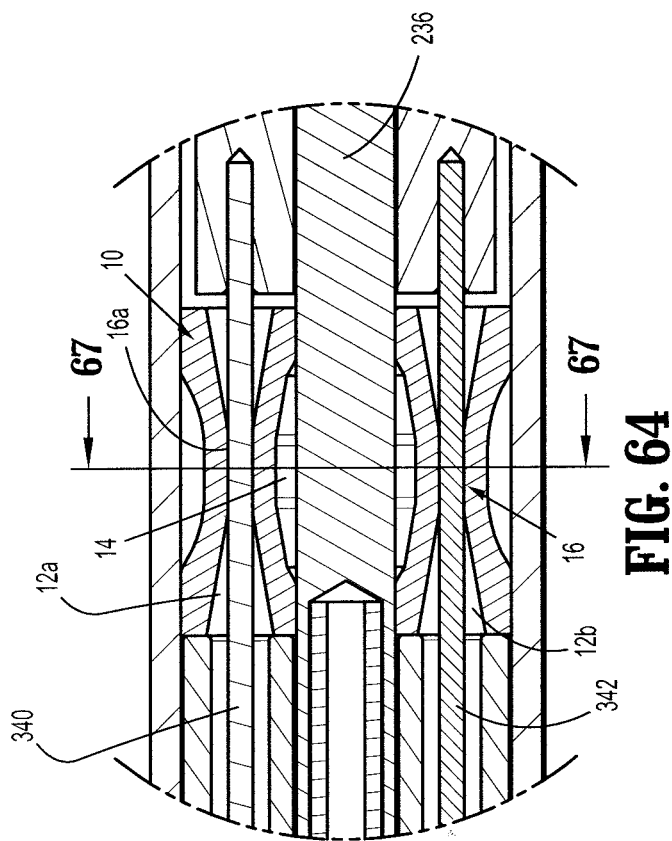
FIG. 64 is an enlarged view of the indicated area of detail of FIG. 63, with the arched seal being illustrated in a first position.
Figure 65:
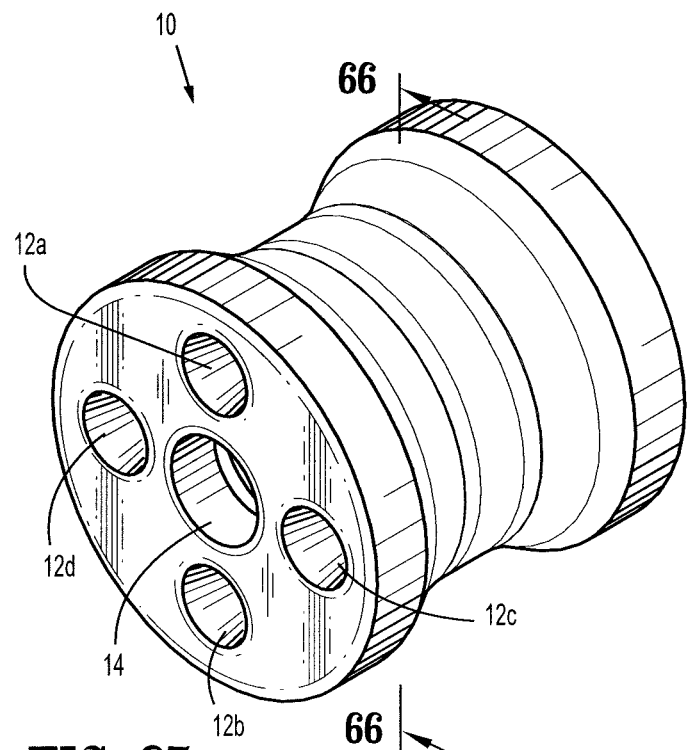
FIG. 65 is a perspective view of the arched seal of FIG. 63.
Figure 66:
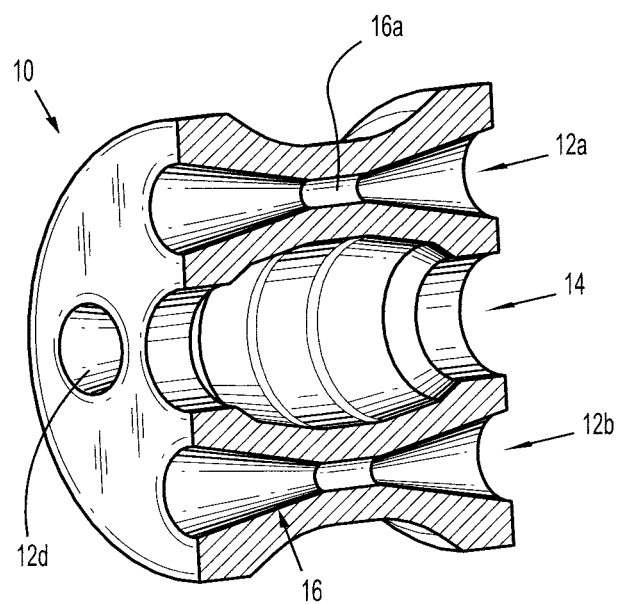
FIG. 66 is a perspective, longitudinal, cross-sectional view of the arched seal of FIGS. 63-65, as taken through 66-66 of FIG. 65.
Figure 67:
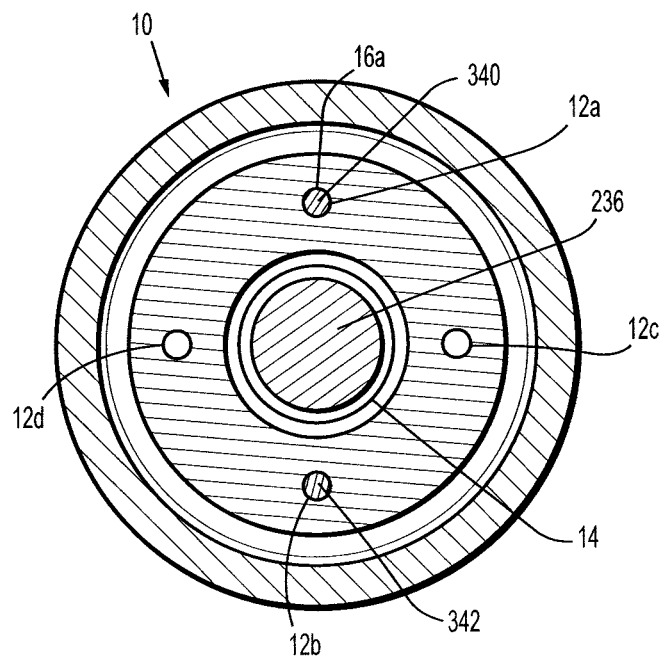
FIG. 67 is a transverse, cross-sectional view of the arched seal of FIGS. 63-66, as taken through 67-67 of FIG. 64.
Figure 68:
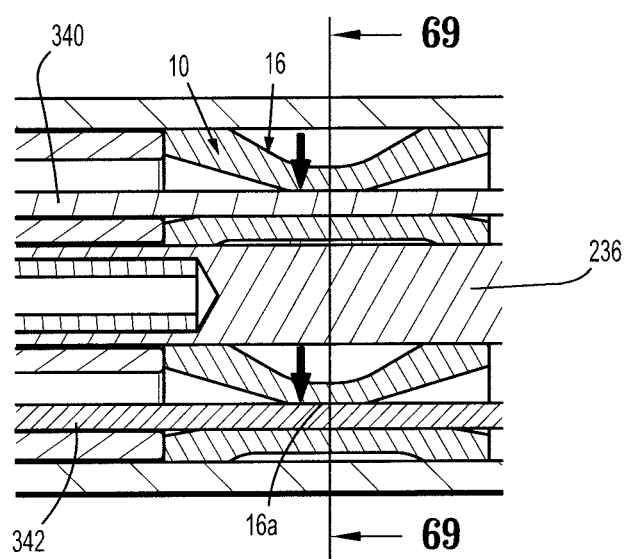
FIG. 68 is a longitudinal, cross-sectional view of the arched seal of FIGS. 63-67, with the arched seal being illustrated in a second position.
Figure 69:
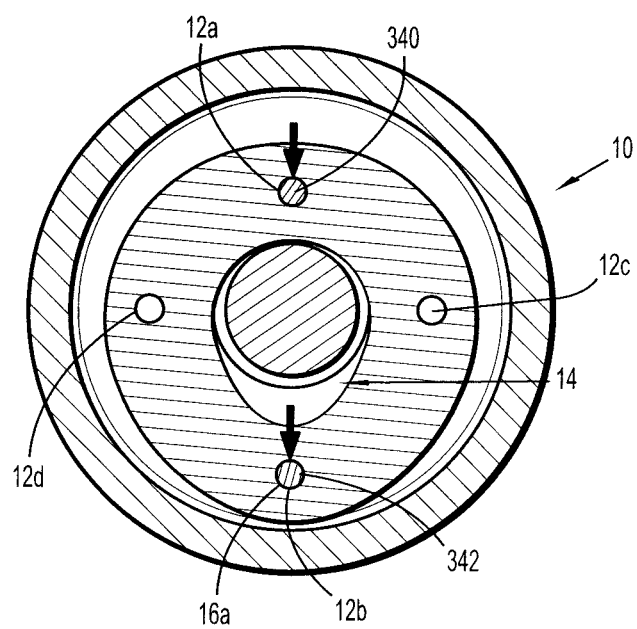
FIG. 69 is a transverse, cross-sectional view of the arched seal of FIGS. 63-68, as taken through 69-69 of FIG. 68.

In operation, as seen in FIG. 62, as rotation knob 572 is rotated, stems 574a of nut 574 are engaged by the inner helical thread 572a of rotation knob 572 and cause nut 574 to move axially through housing 502 and elongate slots 502a of housing 502. As nut 574 moves axially though slots 502a of housing 502, inner thread 574a thereof engages thread 576a of lead screw 576 causing lead screw 576 to rotate since lead screw 576 is axially fixed in braces 502b of housing 502. As lead screw 576 rotates, lead screw 576 transmits said rotation to center drive rod assembly 236.

Referring now to FIGS. 63-69, it is contemplated that each articulation cable 340, 342 may be operably associated with an arched seal 10 disposed in mechanical cooperation with center drive rod assembly 236. Arched seal 10 includes a plurality of cable lumens 12a,12d (see 40 FIG. 65) disposed around a center drive rod lumen 14, all extending therethrough. Center drive rod lumen 14 is configured to receive center drive rod assembly 236 therethrough. Each cable lumen 12a,12d is configured to receive one or more articulation cables 340, 342 in substantial sealing relationship therewith. Each cable lumen 12a,12d may have a respective arched section 16 that includes a venturi portion 16a configured to engage a surface of one or more articulation cables 340, 342 so that arched seal 10 may move with articulation cables 340, 342.

Venturi portion 16a of each arched section 16 enables each cable lumen 12a,12d to be repositionable through a plurality of positions including a first position corresponding to a linear orientation of neck assembly 210 (e.g., FIG. 66) and a second position corresponding to an articulated orientation of neck assembly 210 (e.g., FIG. 68) in response to longitudinal translation of one or more articulation cables 340, 342 therethrough. In this manner, the sealing relationship between arched seal 10 and articulation cables 340, 342 is maintained at all times when neck assembly 210 is in either the linear or the articulated orientation.

Figure 70:
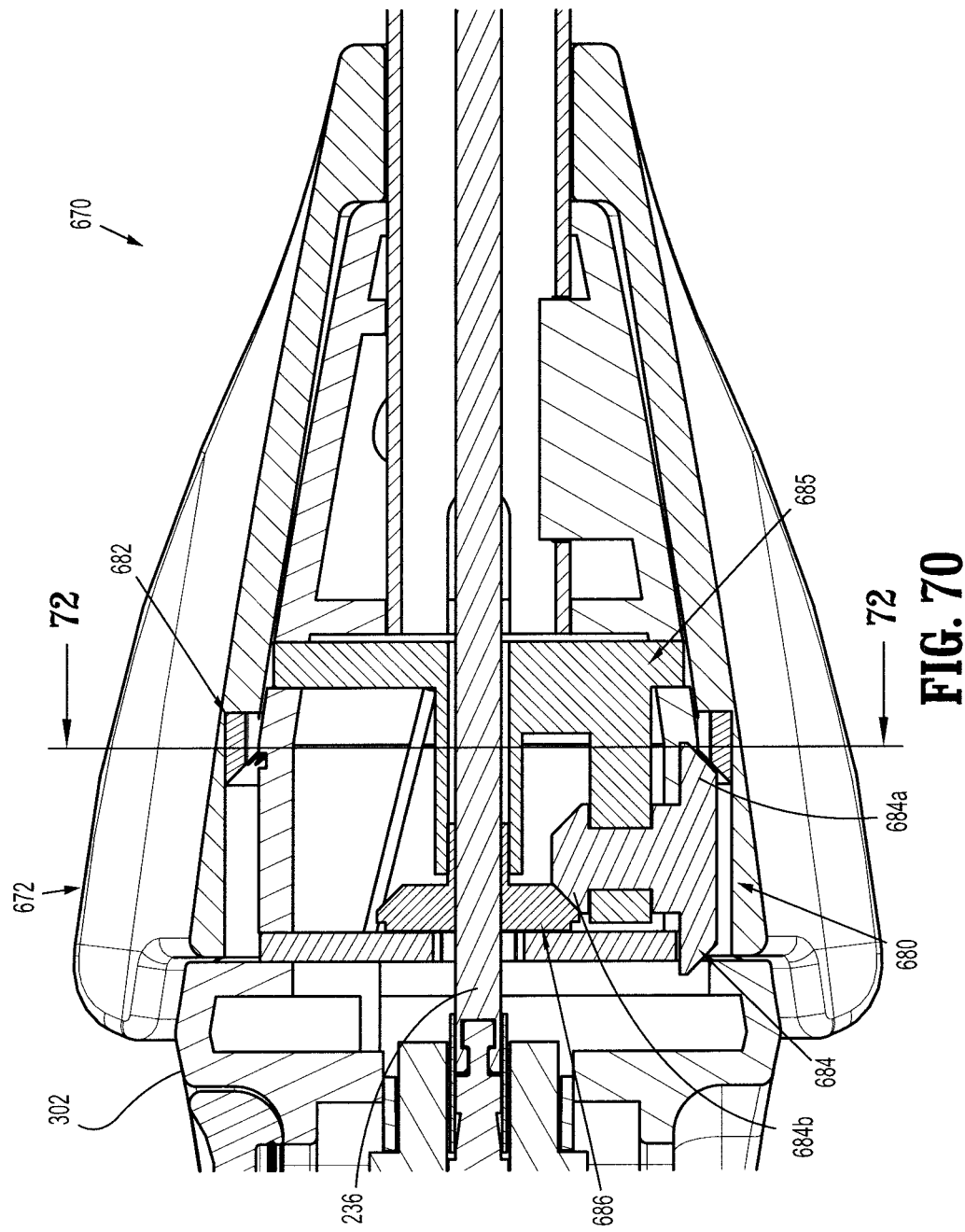
FIG. 70 is a longitudinal, cross-sectional view of an end effector rotation assembly according to another embodiment of the present disclosure.
Figure 71:
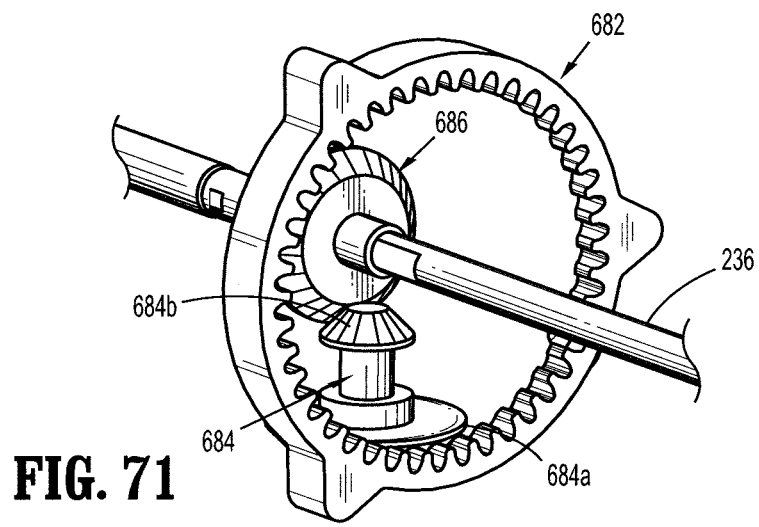
FIG. 71 is a perspective view of a gear assembly of the end effector rotation assembly of FIG. 70.
Figure 72:
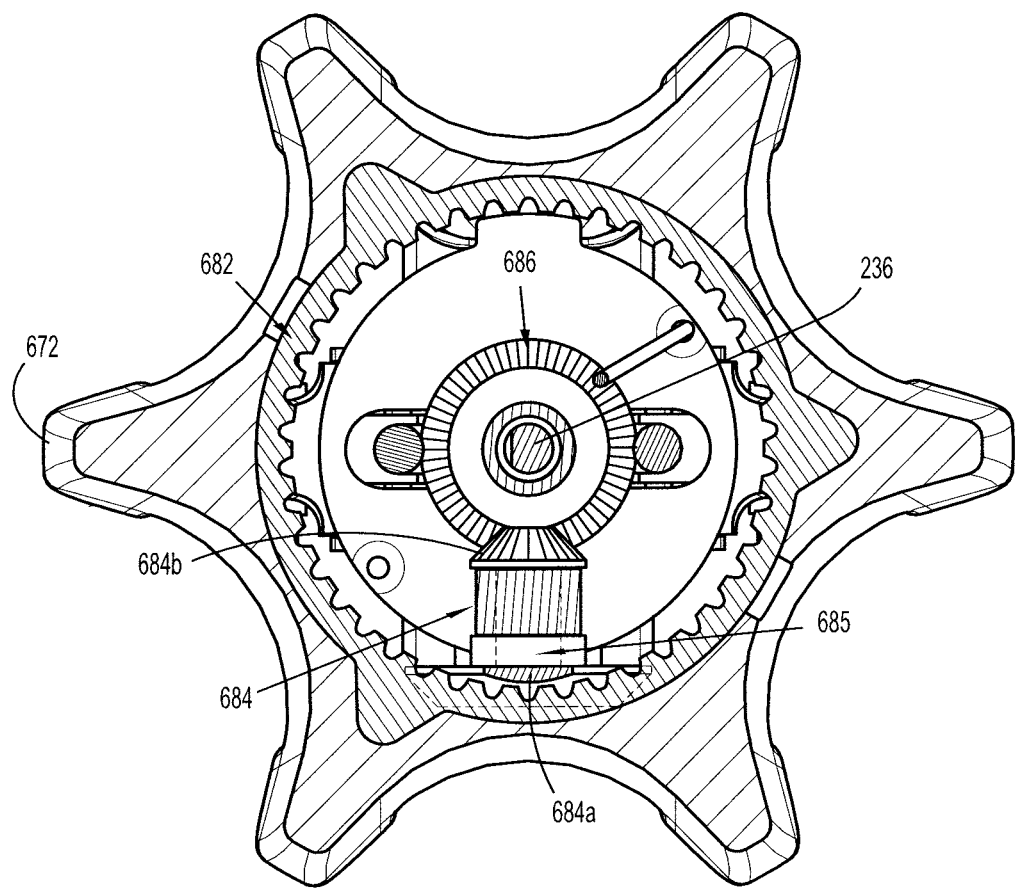
FIG. 72 is a cross-sectional view of the end effector rotation assembly of FIGS. 70 and 71, as taken through 72-72 of FIG. 70.
Figure 73:
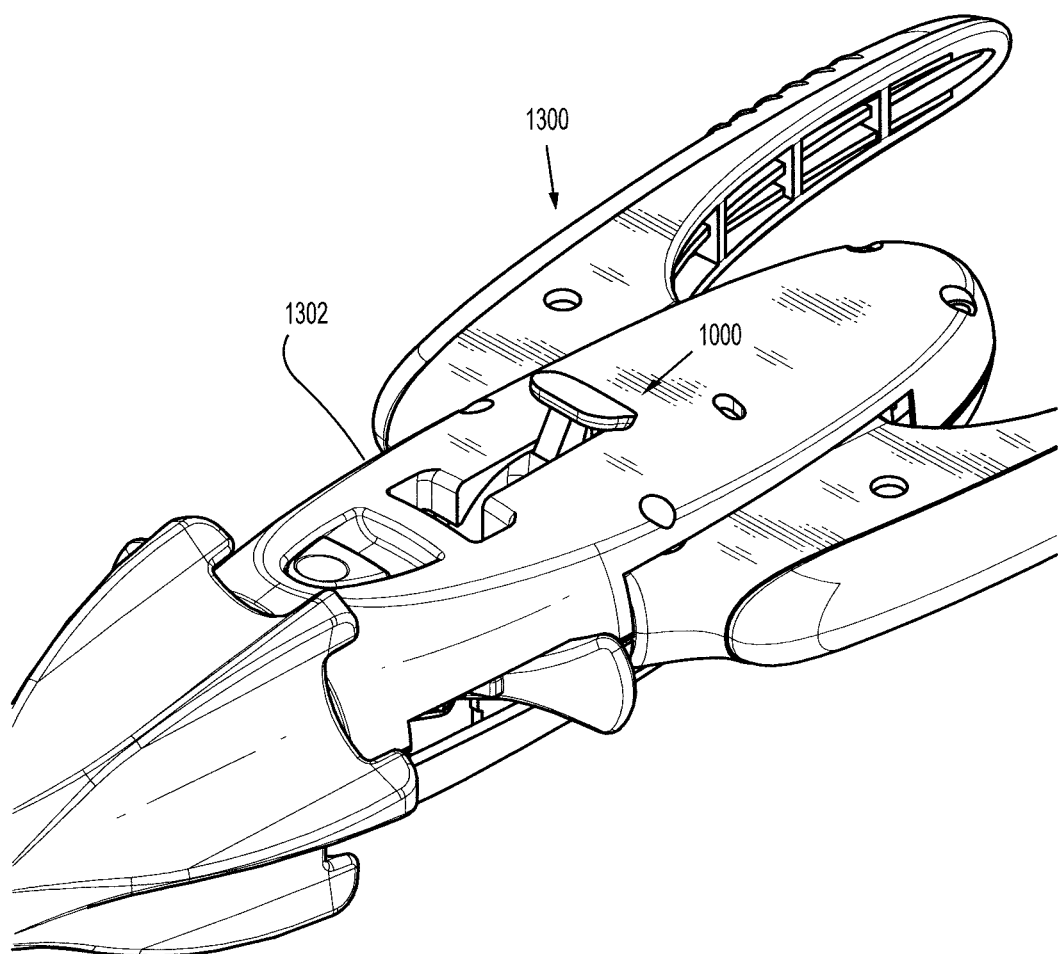
FIG. 73 is a perspective view of another embodiment of a handle assembly of the flexible stitching device, including another embodiment of an articulation assembly therein.
Figure 74:
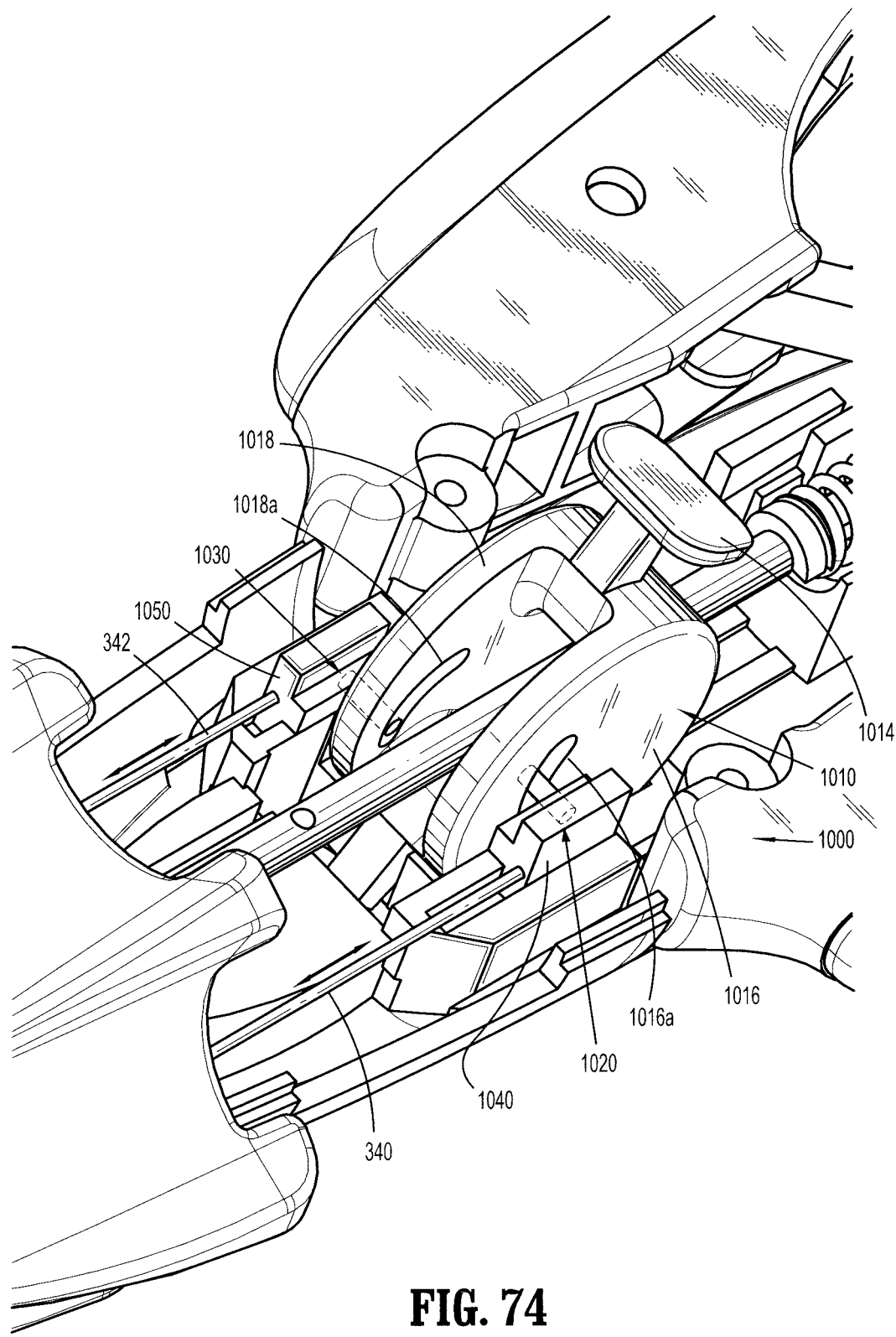
FIG. 74 is an enlarged perspective view of the handle assembly of FIG. 73 with the housing removed to illustrate the articulation assembly.
Figure 75:
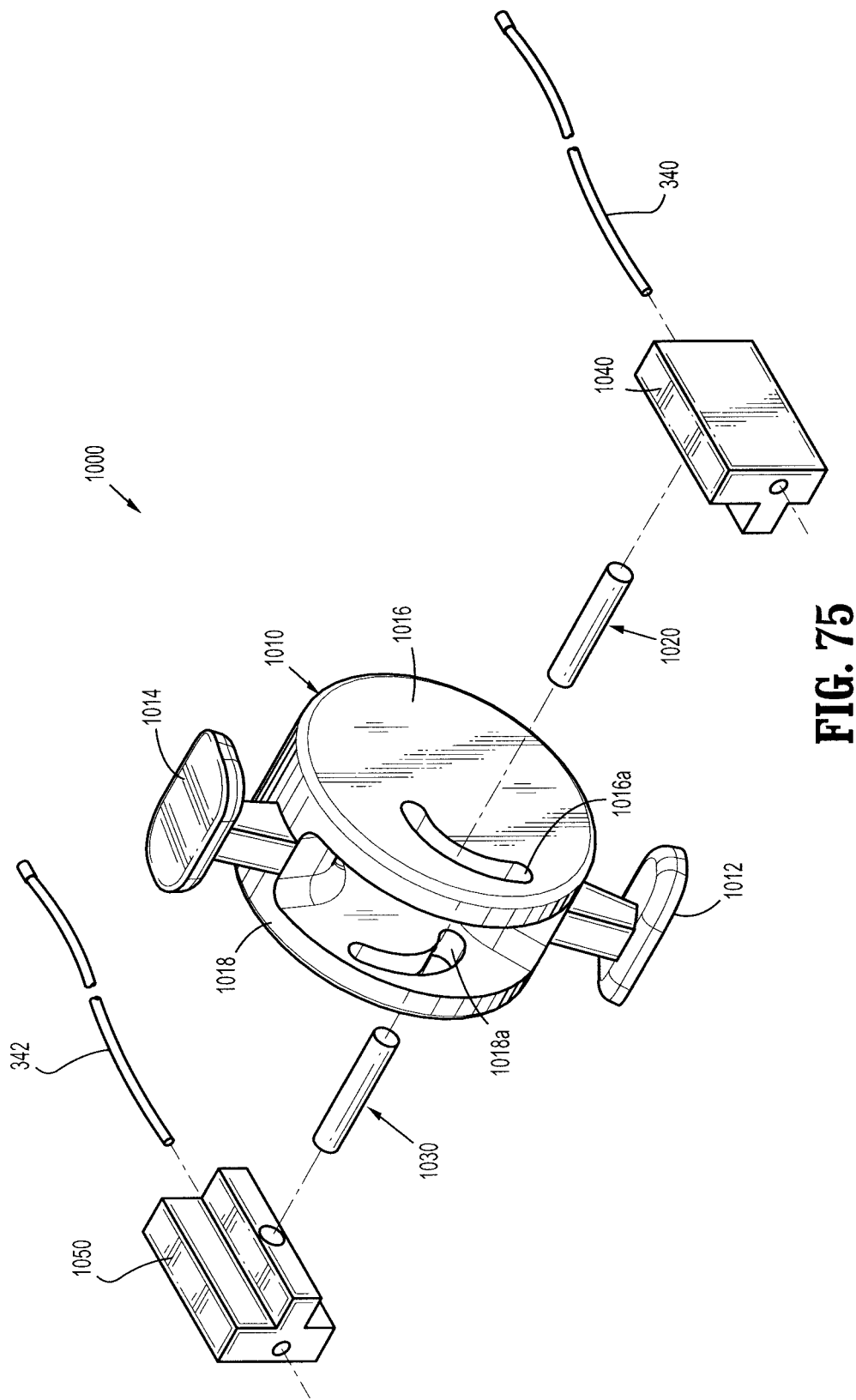
FIG. 75 is a perspective view, with parts separated, of the articulation assembly of FIGS. 73-74.

Turning now to FIGS. 70-72, a tip rotation assembly according to another embodiment of the present disclosure, for use with stitching device 100, is generally designated as 670. Tip rotation assembly 670 includes a rotation knob 672 supported on housing 302 (see FIG. 70) and a beveled gear assembly 680 operatively associated with rotation knob 672. Beveled gear assembly 680 includes a sun gear 682 disposed in mechanical cooperation with knob 672, a first beveled gear 684 that is operatively associated with sun gear 682, and a second beveled gear 686 operatively associated with first beveled gear 684. First beveled gear 684 may be generally orthogonally disposed relative to sun gear 682 and second beveled gear 686. Second beveled gear 686 is disposed in mechanical cooperation with center drive rod assembly 236 for facilitating the transfer of rotational energy from tip rotation assembly 670 to center drive rod assembly 236 for opening and closing jaws 230, 232.

Tip rotation assembly 670 further includes a first beveled gear mount 685 disposed in mechanical cooperation with first beveled gear 684 and knob 672. First beveled gear mount 685 rotatably supports first beveled gear 684 relative to knob 672 and, in particular, interconnecting sun gear 682 and second beveled gear 606.

Sun gear 682 and second beveled gear 686 may be configured and dimensioned to rotate about the longitudinal axis of the stitching device 100 in offset relationship relative to each other. First beveled gear mount 685 is configured to orient first beveled gear 684 such that first beveled gear 684 rotates about an axis transverse to the longitudinal axis of the stitching device 100. Second beveled gear 686 may be keyed to or flat surfaces for engaging center drive rod assembly 236 while still allowing axial movement of center drive rod assembly 236 relative to second beveled gear 686. Sun gear 682, first beveled gear 684, and second beveled gear 686 may be configured and dimensioned to collectively allow only minimal (e.g., five degrees) rotational backlash. In addition, beveled gear assembly 680 of tip rotation assembly 670 may be configured and dimensioned to translate rotational energy to the center drive rod assembly 236 in accordance with one or more of the following ratios: 1:1, more than 1:1, or less than 1:1.

In operation, as rotation knob 672 is rotated (may be clockwise or counterclockwise) about the longitudinal axis of the stitching device 100, sun gear 682 (keyed to rotation knob 672) of beveled gear assembly 680 concentrically rotates therewith. Sun gear 682 engages with a first gear portion 684a of first beveled gear 684, causing first beveled gear 684 to be rotated about an axis transverse to the longitudinal axis of the stitching device 100. Rotation of the first beveled gear 684 causes second gear portion 684b of first beveled gear 684 to engage second beveled gear 686 and to rotate second beveled gear 686 about the longitudinal axis of the stitching device 100. Rotation of the second beveled gear 686 causes the center drive rod assembly 236 to rotate and thus cause jaws 230, 232 to rotate.

Referring now to FIGS. 73-78, a handle assembly 1300 including another embodiment of an articulation assembly 1000 is shown. Articulation assembly 1000 includes an articulation cam 1010, a first pin 1020, a second pin 1030, a first slider 1040, a second slider 1050, and first and second articulation cables 340, 342. Articulation cam 1010 includes first and second articulation arms 1012, 1014, and first and second cam disks 1016, 1018 for positioning articulation cam 1010 through a plurality of positions corresponding to a linear and/or angular orientation of neck assembly 210 including a first position (FIG. 76), a second position (FIG. 77), and a third position (FIG. 78).

Articulation cam 1010 is supported in a housing 1302 of handle assembly 1300. First and second cam disks 1016, 1018 define opposing respective first and second camming channels 1016a, 1018a therein. First and second camming channels 1016a, 1018a may have a shape substantially similar to a logarithmic spiral that may be configured to provide equidistant linear motion directly proportional to the angular rotation of first and second cam disks 1016, 1018. As such, each articulation cable 340, 342 may remain substantially taut upon translation thereof relative to housing 1302.

Referring again to FIGS. 73-78, first pin 1020 is operably associated with first camming channel 1016a of first cam disk 1016 and with first slider 1040. First slider 1040 is configured to longitudinally translate in a channel defined in housing 1302. Second pin 1030 is operably associated with second camming channel 1018a of second cam disk 1018 and with second slider 1050. Second slider 1050 is configured to longitudinally translate in a channel defined in housing 1302. First and second sliders 1040, 1050 are secured to respective proximal ends of first and second articulation cables 340, 342. Distal ends of first and second articulation cables 340, 342 are secured at a location distal of the neck assembly 210, as described above. Articulation cables 340, 342 are disposed on opposed sides of center drive rod assembly 236.

In operation, to articulate neck assembly 210, articulation cam 1010 is rotated via first and/or second articulation arms 1012, 1014. As seen in FIGS. 73-78, as articulation cam 1010, is rotated, first and second pins 1020, 1030 translate through respective first and second camming channels 1016a, 1018a of first and second cam disks 1016, 1018, and cause respective first and second sliders 1040, 1050 to longitudinally translate. As first and second sliders 1040, 1050 longitudinally translate, either first or second articulation cables 340, 342 retract, depending on the direction of the rotation of the articulation cam 1010, thereby causing neck assembly 210 to articulate. In this manner, one articulation cable 340, 342 is retracted, while the other articulation cable 340, 342 extends precisely the same length as the other shortens. The retraction and extension of the articulation cables 340, 342 are proportional with the curvature of first and second camming channels 1016a, 1018a of first and second cam disks 1016, 1018.

In other words, upon articulation of neck assembly 210, the articulation cable 340, 342 translating in a distal direction must travel a greater distance as compared to articulation cable 340, 342 translating in a proximal direction. As such, in order to compensate for any slack in the tension of articulation cables 340, 342, first and second camming channels 1016a, 1018a have been shaped to cause greater proximal translation of articulation cable 340 or 342 the greater the degree of rotation of first and/or second actuation arms 1012,1014.

Figure 79:
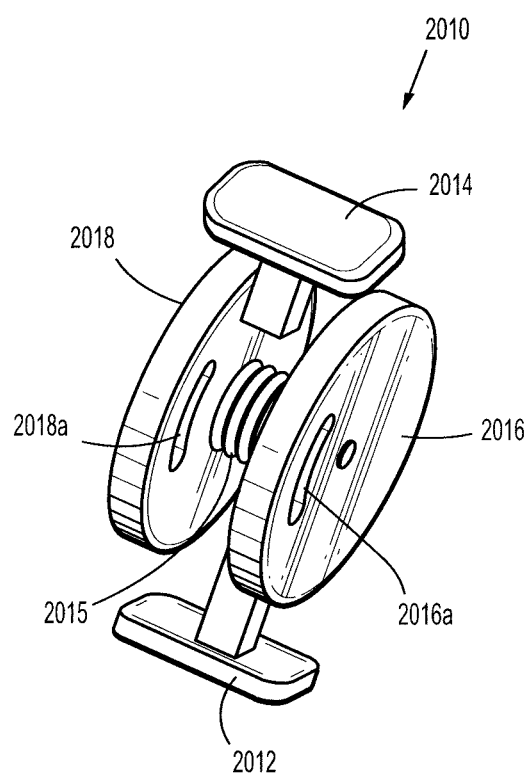
FIG. 79 is a perspective view of another embodiment of an articulation cam in accordance with the present disclosure.

First and second cam disks 1016, 1018 may be monolithically formed. As illustrated in another embodiment of an articulation cam designated generally as 2010 and shown in FIG. 79, first and second cam disks 2016, 2018 may be separate and distinct such that each may rotate in opposed rotational directions via first and second articulation arms 2012, 2014. A torsion spring 2015 may operably couple first and second cam disks 2016, 2018 such that distal and proximal ends of torsion spring 2015 are disposed in mechanical cooperation with respective first and second cam disks 2016, 2018. Torsion spring 2015 may be supported on a shaft axially disposed between first and second cam disks 2016, 2018 to facilitate about 10 to 15 degree rotation of each cam disk 2016, 2018 in relation to each other. Torsion spring 2015 may be preloaded such that it generates force sufficient for maintaining articulation cables 340, 342 in tension for precision operation of the stitching device 100, yet configured to limit rotation of first and second cam disks 2016, 2018 relative to each other during articulation of the neck assembly 210.

Figure 80:
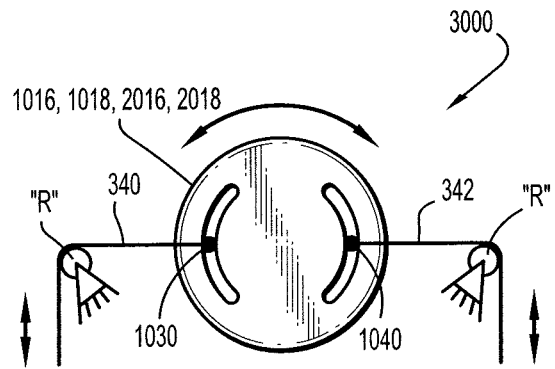
FIG. 80 is a top plan schematic view of another embodiment of an articulation assembly in accordance with the present disclosure.
Figure 81:
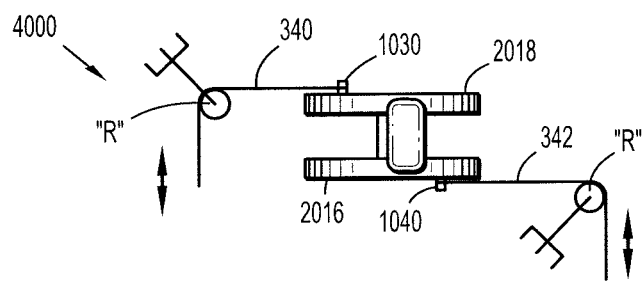
FIG. 81 is a top plan schematic view of another embodiment of an articulation assembly in accordance with the present disclosure.
Figure 82:
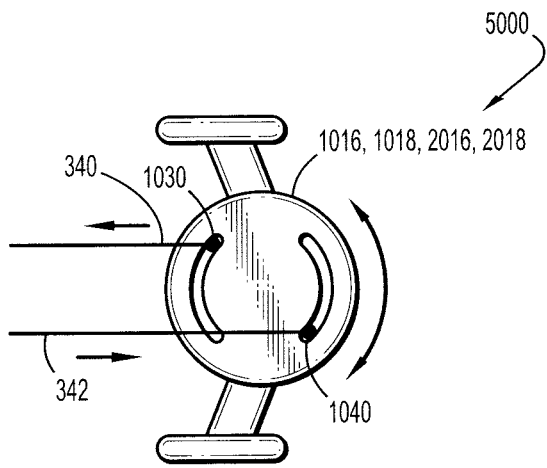
FIG. 82 is a side elevational schematic view of another embodiment of an articulation assembly in accordance with the present disclosure.

As illustrated in other embodiments of articulation assemblies 3000, 4000, 5000 shown in FIGS. 80-82, articulation cables 340, 342 may be attached directly to first or second pins 1020, 1030 that are disposed in mechanical cooperation with respective first and second cam disks 1016, 1018, 2016, 2018 for providing longitudinal translation. As illustrated in the embodiments shown in FIGS. 80-81, articulation cables 340, 342 may be redirected by one or more rollers "R" mounted at various positions on housing 302, 1302. As such, first and second cam disks 1016, 1018, 2016, 2018 may be positioned in longitudinal alignment with the longitudinal axis of the stitching device, transverse thereto, or any other variation thereof since rollers "R" may redirect the articulation cables 340, 342 in any direction, depending on placement thereof.

Turning now to FIGS. 83-88, an alternate embodiment of a neck assembly is generally designated as 1210. Neck assembly 1210 is similar to neck assembly 210 and thus will only be discussed herein to the extent necessary to identify differences in construction and operation thereof.

Figure 83:
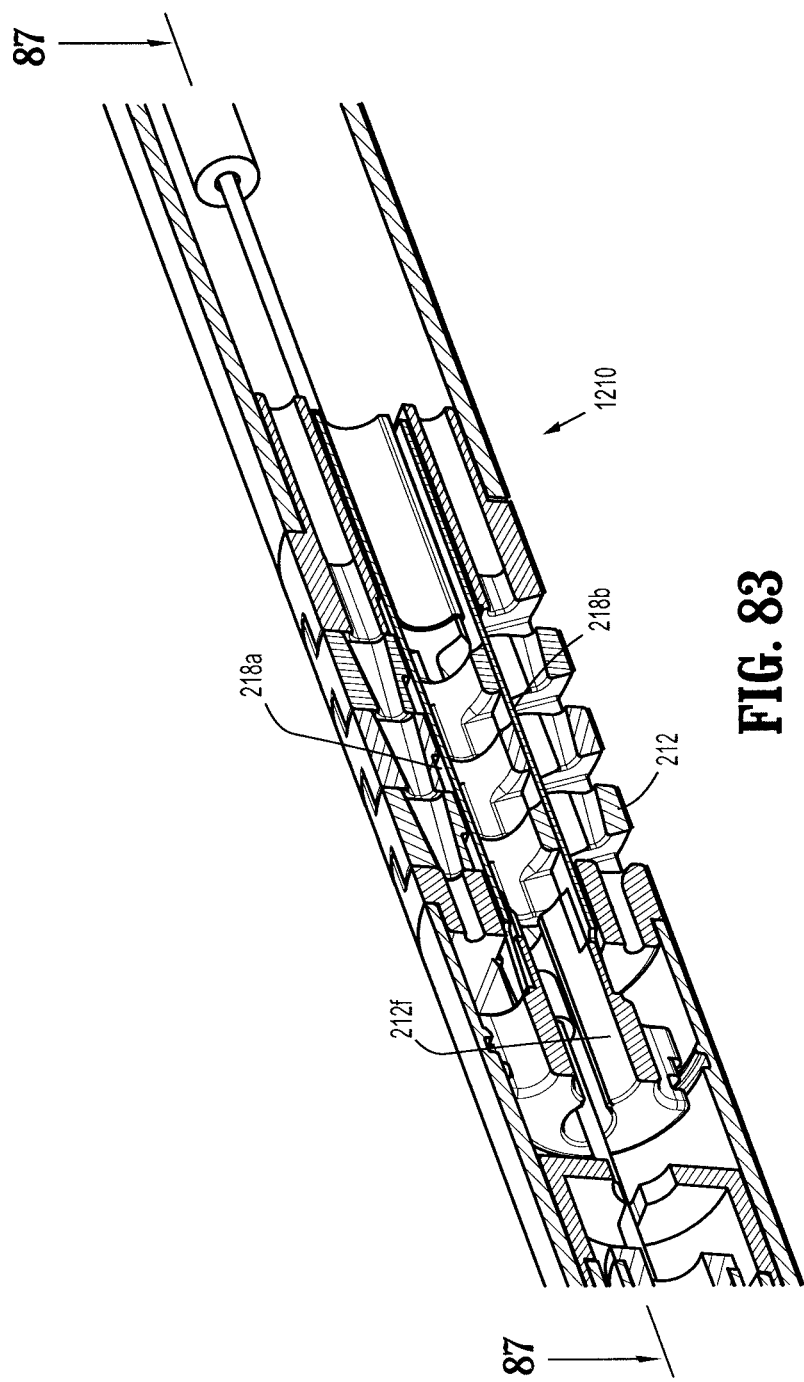
FIG. 83 is a perspective, longitudinal, cross-sectional view of another embodiment of the neck assembly in accordance with the present disclosure, incorporating therein two stiffener plates.
Figure 85B:
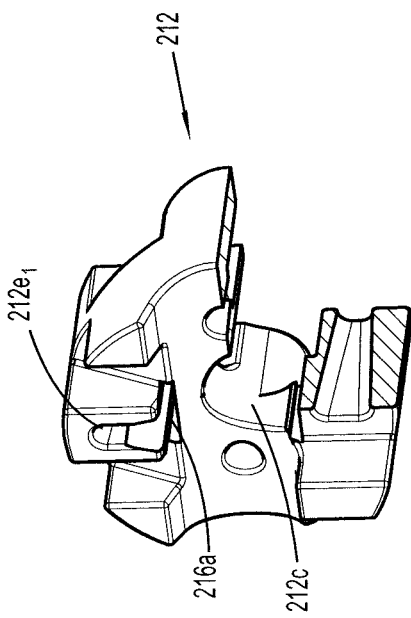
FIG. 85B is a perspective view of the link of FIG. 85A, illustrated with a portion cut away therefrom.
Figure 84B:
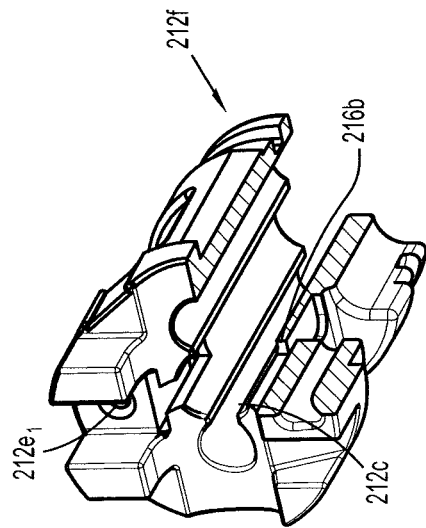
FIG. 84B is a perspective view of the stem of FIG. 84A, illustrated with a portion cut away therefrom.
Figure 85A:
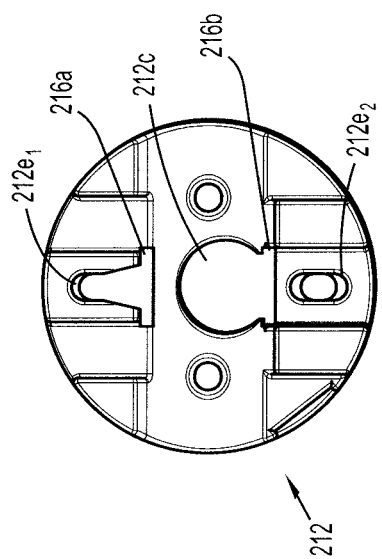
FIG. 85A is a proximal end view of a link of the neck assembly of FIG. 83, configured to receive the two stiffener plates.
Figure 84A:
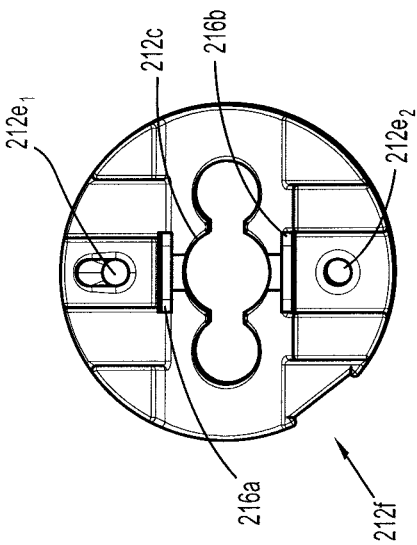
FIG. 84A is a distal end view of a stem of the neck assembly of FIG. 83, configured to receive the two stiffener plates.
Figure 86:
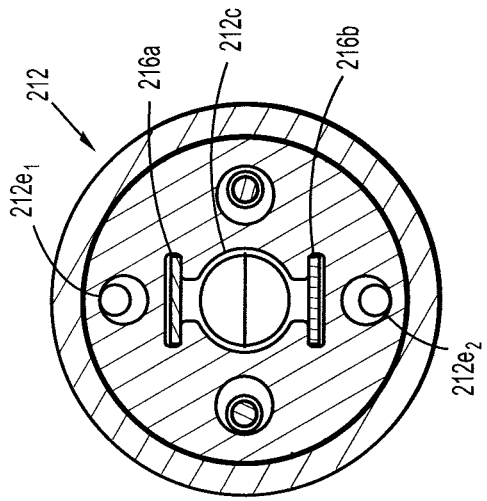
FIG. 86 is a cross-sectional view of another embodiment of a link of a neck assembly in accordance with the present disclosure, incorporating therein two stiffener plates.
Figure 87:
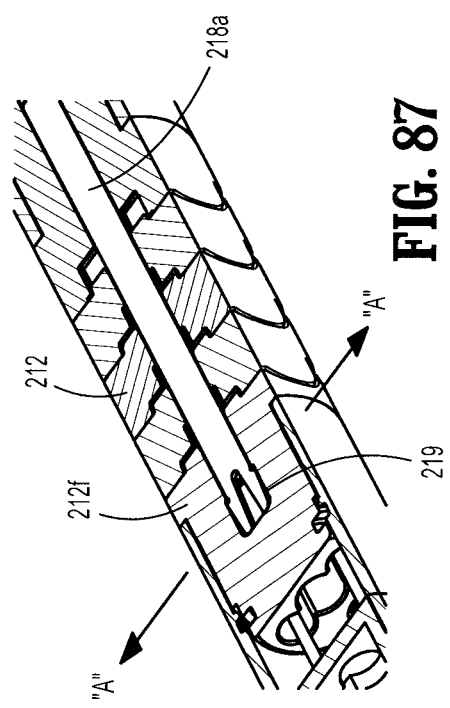
FIG. 87 is a longitudinal cross-sectional view of the neck assembly of FIG. 83 as taken through 87-87 of FIG. 83.
Figure 88:
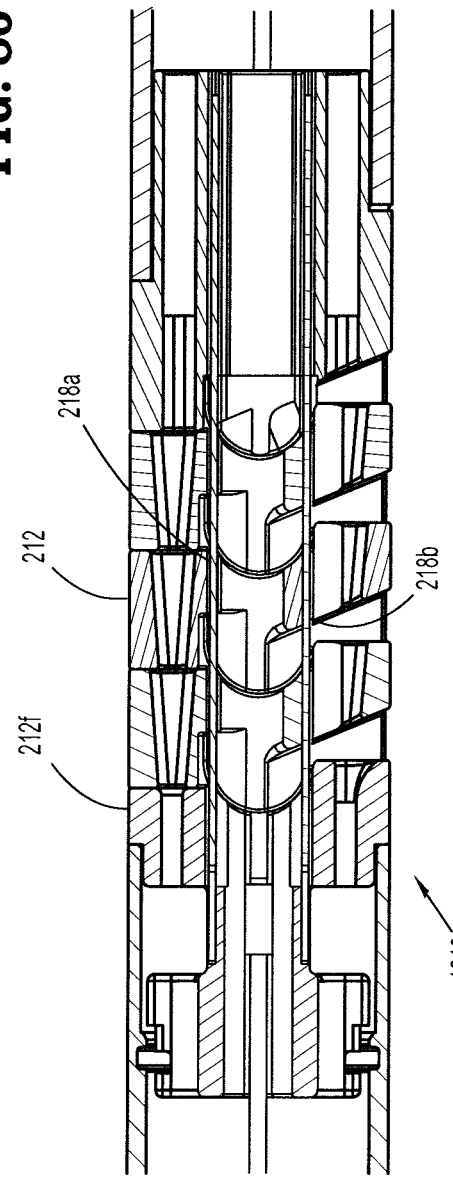
FIG. 88 is another longitudinal, cross-sectional view of the neck assembly of FIG. 83.

As seen in FIGS. 83-88, each link 212 defines a pair of opposed stiffener plate receiving slots 216a, 216b. Slots 216a, 216b are fanned on either side of central lumen 212c and are interposed between central lumen 212c and a respective articulation cable lumen 212e1, 212e2. As shown in FIGS. 83 and 88, neck assembly 1210 includes a pair of stiffener plates 218a, 218b translatably disposed in the plate receiving slots 216a, 216b, respectively. As seen in FIG. 87, a distal-end of each stiffener plate 218a, 218b includes an anchor portion 219 to securely attach respective distal-end of stiffener plate 218a, 218b to stem 212f of neck assembly 1210, while allowing the proximal-end of each stiffener plate 218, 218b to translate freely through plate receiving slots 216a, 216b.

In an embodiment, as seen in FIG. 87, anchor portion 219 of each stiffener plate 218a, 218b may be bifurcated and include a pair of spaced apart tines that snap-fit into packets formed at the ends of plate receiving slots 216a, 216b. Each stiffener plate 218a, 218b may have an elongated, flattered (e.g., ribbon-like) profile. Each stiffener plate 218a, 218b thus defines a plane, wherein the stiffener plates 218a, 218b are supported in neck assembly 1210 such that the respective planes of stiffener plates 218a, 218b are substantially parallel with one another. In the present embodiment, the planes of stiffener plates 218a, 218b are oriented substantially orthogonal to a direction of articulation of end effector 200. Stiffener plates 218a, 218b may be constructed from any durable resilient material, such as, for example, stainless steel, titanium, etc.

Links 212 are configured to enable end effector 200 to move between a substantially linear configuration and a substantially angled, off-axis or articulated configuration. Since stiffener plates 218a, 218b are oriented such that the planes thereof are substantially orthogonal to a direction of articulation of end effector 200, movement or articulation of end effector 200 is restricted solely in two dimensions (i.e., a single plane). As illustrated in FIG. 87, stiffener plate 218a (and stiffener plate 218b, not shown) restrict(s) movement or canting of end effector 200 in the direction of arrows "A."

Figure 89:
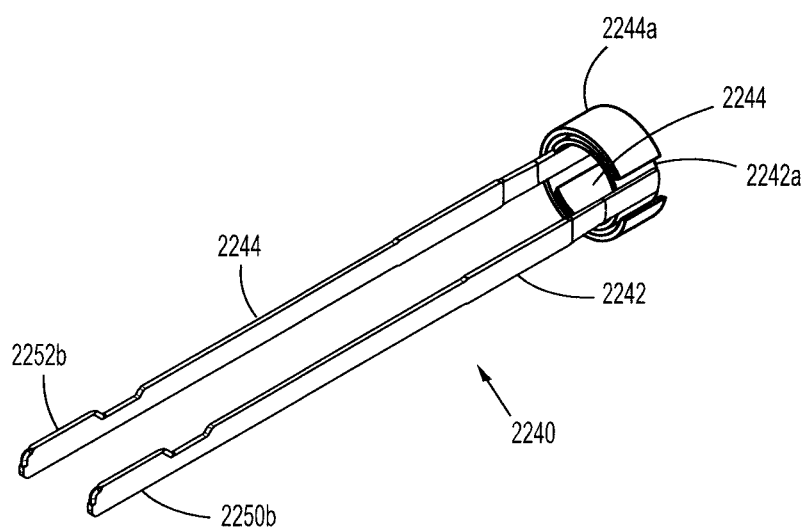
FIG. 89 is a perspective view of a drive assembly according to another embodiment of the present disclosure.

Turning now to FIG. 89, an alternate embodiment of a drive assembly is generally designated as 2240. Drive assembly 2240 is similar to drive assembly 240 and thus will only be discussed herein to the extent necessary to identify differences in construction and operation thereof. As seen in FIG. 89, drive assembly 2240 includes an inner drive member 2242 and an outer drive member 2244. Inner drive member 2242 includes a partially circular collar 2242a and a first blade 2250b extending therefrom. First blade 2250b and the partially circular collar 2242a are constructed or stamped as one unitary member from one piece of sheet metal. Similarly, outer drive member 2244 includes a partially circular collar 2244a and a second blade 2252b extending therefrom. Second blade 2252b and the partially circular collar 2244a are also constructed or stamped as one unitary member from one piece of sheet metal. The partially circular collar 2242a of inner drive member 2242 is nested within the partially circular collar 2244a of outer drive member 2244 and defines a lumen 2242b through which center drive rod distal portion 236a of center drive rod assembly 236 is received. Inner and outer drive members 2242, 2244 provide a snap feature that snaps around inner and outer bushings (not shown), thereby allowing rotation of inner and outer drive members 2242, 2244 around the inner and outer bushings, respectively. Such design reduces the number of parts that are required to hold blades 2250b, 2252b in place, thereby simplifying manufacturability and reducing cost of manufacturing.

While the disclosure has been particularly shown and described with reference to particular embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. An end effector for use with an endoscopic stitching device comprising:
   a pair of jaws, each jaw of the pair of jaws defining a suture needle receiving recess formed in a tissue contacting surface of each of the pair of jaws; and
   a neck assembly configured for articulation in one direction between a substantially linear configuration and an off-axis configuration, wherein the neck assembly defines a central longitudinal axis, the neck assembly including:
      a plurality of links in pivotable contact with one another, each link of the plurality of links including:
         a knuckle formed on a first side of the link;
         a clevis formed on a second side of the link, the knuckle of a link of the plurality of links being operatively connected to the clevis of an adjacent link; and
      a first stiffener plate and a second stiffener plate each extending through at least a pair of operatively connected links of the plurality of links, each stiffener plate including a proximal end and a distal end, wherein of the proximal end and the distal end of each stiffener plate only the distal end is axially fixed, wherein:
         the first stiffener plate is located a first radial distance from the central longitudinal axis of the neck assembly; and
         the second stiffener plate is located a second radial distance, opposite the first radial distance, from the central longitudinal axis of the neck assembly.

2. The end effector according to claim 1, wherein the the neck assembly is articulatable in a direction out of a plane defined by the first stiffener plate.

3. The end effector according to claim 1, wherein the knuckles and devises are configured to enable articulation of the neck assembly in a single plane.

4. The end effector according to claim 1, wherein the knuckles and devises are configured to at least partially overlap one another when the neck assembly is in one of the substantially linear configuration or the off-axis configuration.

5. An end effector for use with an endoscopic stitching device comprising:
   a pair of jaws pivotally associated with one another;
   a neck assembly configured for articulation in one direction between a substantially linear configuration and an off-axis configuration, wherein the neck assembly defines a central longitudinal axis;
   a first stiffener plate disposed in the neck assembly and axially extending within the neck assembly, the first stiffener plate including a proximal end and a distal end, wherein of the proximal end and the distal end of the first stiffener plate only the distal end of the first stiffener plate is axially fixed, the first stiffener plate is located a first radial distance from the central longitudinal axis of the neck assembly; and
   a second stiffener plate disposed in the neck assembly and axially extending within the neck assembly, the second stiffener plate including a proximal end and a distal end, wherein of the proximal end and the distal end of the second stiffener plate only the distal end of the second stiffener plate is axially fixed, the second stiffener plate is located a second radial distance, opposite the first radial distance, from the central longitudinal axis of the neck assembly,
   wherein the first stiffener plate and the second stiffener plate inhibit canting of the end effector in a direction orthogonal to the one direction of articulation of the end effector.

6. The end effector according to claim 5, wherein of the first stiffener plate and the second stiffener plate each defines a respective plane that is substantially orthogonal to the direction of articulation of the end effector.

7. The end effector according to claim 6, wherein each of the first stiffener plate and the second stiffener plate is substantially flat and is bendable in a first direction.

8. The end effector according to claim 6, wherein the the neck assembly is articulatable in a direction out of the plane defined by either the first stiffener plate or the second stiffener plate.

9. The end effector according to claim 6, wherein each of the first stiffener plate and the second stiffener plate restricts articulation of the end effector in the plane defined by either one of the first stiffener plate and the second stiffener plate.

10. The end effector according to claim 6, wherein the distal end of each of the first stiffener plate and the second stiffener plate includes at least a pair of spaced apart tines secured to the neck assembly.

11. The end effector according to claim 6, wherein the neck assembly further includes a plurality of links in pivotable contact with one another, wherein each link defines a pair of stiffener plate receiving slots for respectively receiving the first stiffener plate and the second stiffener plate.

12. The end effector according to claim 11, wherein the first stiffener plate extends through a first of the pair of stiffener plate receiving slots of at least one link of the plurality of links, and the second stiffener plate extends through a second of the pair of stiffener plate receiving slots of at least one link of the plurality of links.

13. The end effector according to claim 11, wherein the first stiffener plate and the second stiffener plate extend through the stiffener plate receiving slots of the entire plurality of links.

14. The end effector according to claim 6, wherein each stiffener plate is made of resilient material.

15. An end effector of an endoscopic stitching device comprising:
   a tool assembly;
   a neck assembly coupled to the tool assembly and configured for articulation in one direction between a substantially linear configuration and an off-axis configuration, wherein the neck assembly defines a central longitudinal axis; and
   a pair of spaced apart stiffener plates axially extending in the neck assembly,
   wherein each stiffener plate of the pair of spaced apart stiffener plates defines a plane and includes a proximal end and a distal end, wherein of the proximal ends and the distal ends of the respective pair of spaced apart stiffener plates only the distal ends of the respective pair of spaced apart stiffener plates are axially fixed, wherein the pair of spaced apart stiffener plates includes:
      a first stiffener plate located a first radial distance from the central longitudinal axis of the neck assembly; and
      a second stiffener plate located a second radial distance, opposite the first radial distance, from the central longitudinal axis of the neck assembly.

16. The end effector according to claim 15, wherein the plane defined by each stiffener plate of the pair of spaced apart stiffener plates is substantially orthogonal to the one direction of articulation.

17. The end effector according to claim 16, wherein each stiffener plate of the pair of spaced apart stiffener plates is substantially flat and is bendable in one direction.

18. The end effector according to claim 15, wherein the neck assembly is articulatable in a direction out of the plane defined by a respective one of the pair of spaced apart stiffener plates.

19. The end effector according to claim 15, wherein the tool assembly defines suture needle receiving recess formed in a tissue contacting surface of the tool assembly.

* * * * *